(12) United States Patent
D'Hondt et al.

(10) Patent No.: US 12,134,662 B2
(45) Date of Patent: Nov. 5, 2024

(54) SYNTHETIC PROTEINS AND THERAPEUTIC USES THEREOF

(71) Applicant: IN3BIO LTD., Hamilton (BM)

(72) Inventors: Erik D'Hondt, Bazel (BE); Keith Alan Charlton, Aberdeenshire (GB)

(73) Assignee: In3Bio Ltd., Hamilton (BM)

( * ) Notice: Subject to any disclaimer, the term of this patent is extended or adjusted under 35 U.S.C. 154(b) by 542 days.

(21) Appl. No.: 16/631,690

(22) PCT Filed: Jul. 18, 2018

(86) PCT No.: PCT/IB2018/000898
§ 371 (c)(1),
(2) Date: Jan. 16, 2020

(87) PCT Pub. No.: WO2019/016597
PCT Pub. Date: Jan. 24, 2019

(65) Prior Publication Data
US 2021/0009716 A1    Jan. 14, 2021

Related U.S. Application Data

(60) Provisional application No. 62/533,901, filed on Jul. 18, 2017.

(51) Int. Cl.
| | | |
|---|---|---|
| *C07K 19/00* | (2006.01) | |
| *A61K 38/18* | (2006.01) | |
| *C07K 14/28* | (2006.01) | |
| *C07K 14/485* | (2006.01) | |
| *C07K 14/495* | (2006.01) | |

(52) U.S. Cl.
CPC .......... *C07K 19/00* (2013.01); *A61K 38/1883* (2013.01); *C07K 14/28* (2013.01); *C07K 14/485* (2013.01); *C07K 14/495* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,894,018 A | 4/1999 | Bienvenido et al. | |
| 9,902,760 B2* | 2/2018 | Charlton | A61P 37/04 |
| 11,198,716 B2* | 12/2021 | Charlton | A61P 43/00 |
| 2005/0246087 A1 | 11/2005 | Hommi et al. | |
| 2008/0249008 A1 | 10/2008 | Cochran et al. | |
| 2016/0333087 A1 | 11/2016 | D'Hondt et al. | |

FOREIGN PATENT DOCUMENTS

| | | |
|---|---|---|
| CN | 104066447 A | 9/2014 |
| JP | 2014-534258 A | 12/2014 |
| JP | 2016-517402 A | 6/2016 |
| KR | 10-2014-0108235 A | 9/2014 |
| WO | 2013/076580 A2 | 5/2013 |
| WO | 2014/140894 A2 | 9/2014 |

OTHER PUBLICATIONS

International Search Report for International Application No. PCT/IB2018/000898 dated Mar. 18, 2019.
Van de Poll ML et al., Non-linear antigenic regions in epidermal growth factor (EGF) and transforming growth factor α (TGFα) studied by EGF-TGFα chimaeras, Biochemical Journal, 2000, vol. 349 No. 1.
Office Action in corresponding Japanese application No. 2020-502422 dated May 31, 2022.
Larsen J.N. et al.: "Allergy immunotherapy: the future of allergy treatment", Drug Discovery Today, 2016, v. 21 (1): 26-37.
Pfeiffer A.H. et al.: "The Treatment of Type 2 Diabetes", Dtsch Arztebl Int., 2014, v. 111(5): 69-82.
Office Action in corresponding Chinese application No. 201880053878.8 dated Jan. 18, 2023.
Office Action in corresponding KR application No. 10-2020-7004272 dated Nov. 28, 2023.
Examination Report in corresponding AU application No. 2018304957 dated May 21, 2024.

* cited by examiner

*Primary Examiner* — Christine J Saoud
*Assistant Examiner* — Jon M Lockard
(74) *Attorney, Agent, or Firm* — Withers Bergman LLP; John C. Serio

(57) ABSTRACT

The present disclosure relates to compositions and methods for treating disease. More particularly, the disclosure relates to synthetic proteins and their use for treating cancer.

19 Claims, 19 Drawing Sheets

Specification includes a Sequence Listing.

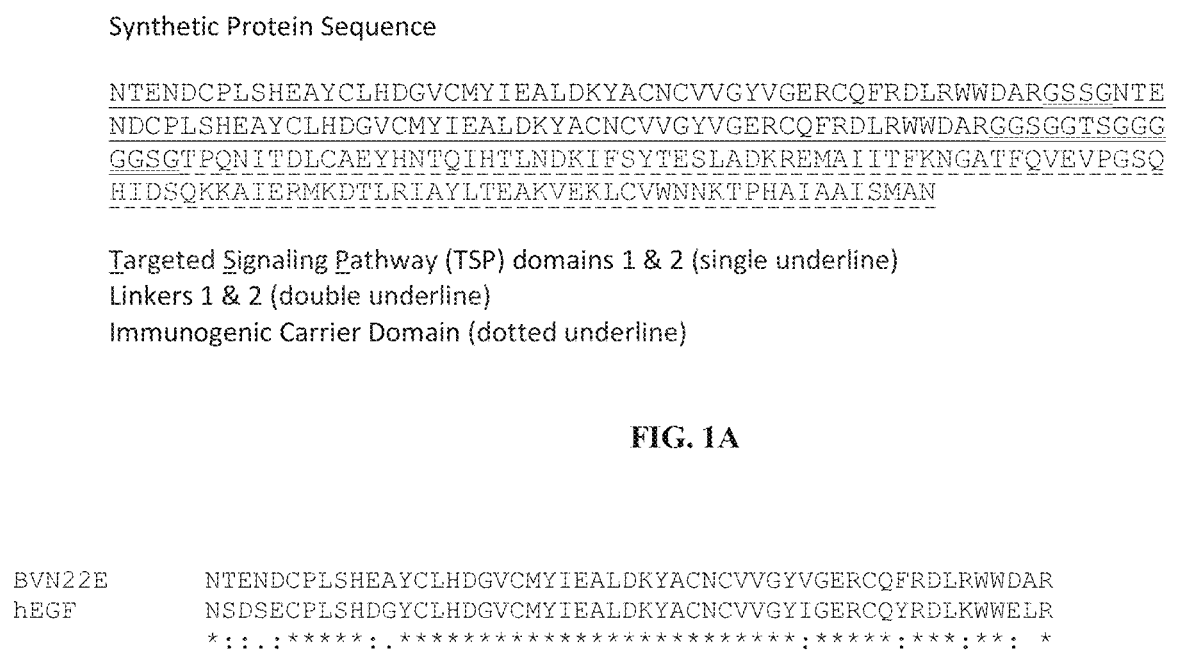

Synthetic Protein Sequence

```
NTENDCPLSHEAYCLHDGVCMYIEALDKYACNCVVGYVGERCQFRDLRWWDARGSSGNTE
NDCPLSHEAYCLHDGVCMYIEALDKYACNCVVGYVGERCQFRDLRWWDARGGSGGTSGGG
GGSGTPQNITDLCAEYHNTQIHTLNDKIFSYTESLADKREMAIITFKNGATFQVEVPGSQ
HIDSQKKAIERMKDTLRIAYLTEAKVEKLCVWNNKTPHAIAAISMAN
```

Targeted Signaling Pathway (TSP) domains 1 & 2 (single underline)
Linkers 1 & 2 (double underline)
Immunogenic Carrier Domain (dotted underline)

FIG. 1A

```
BVN22E       NTENDCPLSHEAYCLHDGVCMYIEALDKYACNCVVGYVGERCQFRDLRWWDAR
hEGF         NSDSECPLSHDGYCLHDGVCMYIEALDKYACNCVVGYIGERCQYRDLKWWELR
             *::.:*****:.*************************:*****:***:**: *
```

Total EGF-R
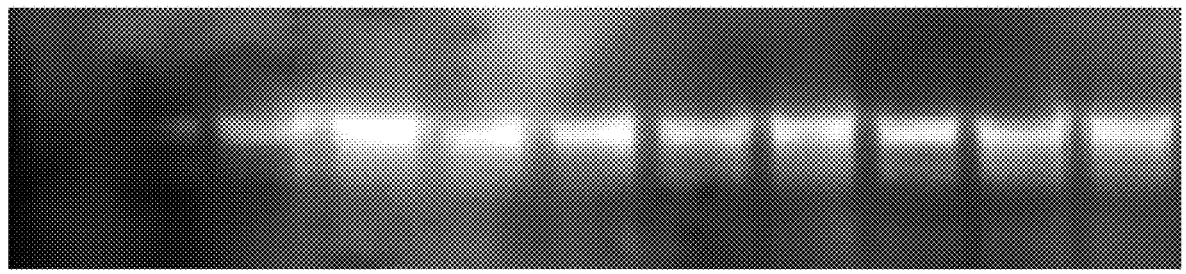
Phosphorylated EGF-R
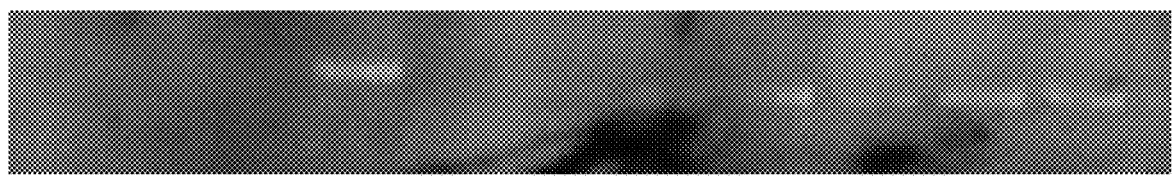
Lane:  M  marker
1  Cell only control (no activation)
2  +ve control (activated with 30 ng/ml rhEGF)
3  -ve control (rhEGF + neutralizing mAb)
4  30 ng/ml rhEGF + BVN22E sera @1/10
5  30 ng/ml rhEGF + BVN22E sera @1/100
6  30 ng/ml rhEGF + BVN22E sera @1/1000
7  30 ng/ml rhEGF + EGF immunogen sera @1/10
8  30 ng/ml rhEGF + EGF immunogen sera @1/100
9  30 ng/ml rhEGF + EGF immunogen sera @1/1000
FIG. 9

SEQUENCE LISTING

<160> NUMBER OF SEQ ID NOS: 35

<210> SEQ ID NO 1
<211> LENGTH: 681
<212> TYPE: DNA
<213> ORGANISM: Artificial
<220> FEATURE:
<223> OTHER INFORMATION: Synthetic

<400> SEQUENCE: 1

```
ataccgaaa  acgattgccc  tctgtctcat  gaagcgtatt  gtctgcacga  cggcgtgtgt      60
atgtacattg  aagccctgga  caaatatgca  tgtaactgtg  tcgtgggcta  cgtggggag    120 cgatgtcagt  ttcgagacct  gcgttggtgg  gatgcgcgcg  gctcgagcgg  taataccgaa    180
aacgattgcc  ctctgtctca  tgaagcgtat  tgtctgcacg  acggcgtgtg  tatgtacatt    240
gaagccctgg  acaaatatgc  atgtaactgt  gtcgtgggct  acgtggggga  gcgatgtcag    300
tttcgagacc  tgcgttggtg  gatgcgcgc  ggcgggtctg  gaggtactag  tggcggcggt    360
ggagggtcgg  gtacccgca  gaacatcacc  gacctgtgcg  ccgagtacca  caacacccag    420
```

```
atccacaccc tgaacgacaa gatcttctcg tacaccgaga gcctggccga taagcgtgaa    480
atggccatca tcaccttcaa gaacggtgcg accttccagg tggaggtccc gggtagccag    540
cacatcgatt cacagaagaa ggccatcgag cgtatgaagg acaccctgcg tatcgcctac    600
ctgaccgaag ccaaggtgga aaagctgtgc gtctggaaca acaagacgcc gcacgccatc    660
gccgccatca gcatggccaa t                                              681
```

```
<210> SEQ ID NO 2
<211> LENGTH: 227
<212> TYPE: PRT
<213> ORGANISM: Artificial
<220> FEATURE:
<223> OTHER INFORMATION: Synthetic

<400> SEQUENCE: 2

Asn Thr Glu Asn Asp Cys Pro Leu Ser His Glu Ala Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Val Gly Glu Arg Cys Gln Phe Arg Asp Leu Arg
        35                  40                  45

Trp Trp Asp Ala Arg Gly Ser Ser Gly Asn Thr Glu Asn Asp Cys Pro
    50                  55                  60

Leu Ser His Glu Ala Tyr Cys Leu His Asp Gly Val Cys Met Tyr Ile
65                  70                  75                  80

Glu Ala Leu Asp Lys Tyr Ala Cys Asn Cys Val Val Gly Tyr Val Gly
                85                  90                  95

Glu Arg Cys Gln Phe Arg Asp Leu Arg Trp Trp Asp Ala Arg Gly Gly
            100                 105                 110

Ser Gly Gly Thr Ser Gly Gly Gly Gly Ser Gly Thr Pro Gln Asn
        115                 120                 125

Ile Thr Asp Leu Cys Ala Glu Tyr His Asn Thr Gln Ile His Thr Leu
    130                 135                 140

Asn Asp Lys Ile Phe Ser Tyr Thr Glu Ser Leu Ala Asp Lys Arg Glu
145                 150                 155                 160

Met Ala Ile Ile Thr Phe Lys Asn Gly Ala Thr Phe Gln Val Glu Val
                165                 170                 175

Pro Gly Ser Gln His Ile Asp Ser Gln Lys Lys Ala Ile Glu Arg Met
            180                 185                 190

Lys Asp Thr Leu Arg Ile Ala Tyr Leu Thr Glu Ala Lys Val Glu Lys
        195                 200                 205

Leu Cys Val Trp Asn Asn Lys Thr Pro His Ala Ile Ala Ala Ile Ser
    210                 215                 220

Met Ala Asn
225
```

```
<210> SEQ ID NO 3
<211> LENGTH: 6369
<212> TYPE: DNA
<213> ORGANISM: Artificial
<220> FEATURE:
<223> OTHER INFORMATION: Synthetic

<400> SEQUENCE: 3
gtccgggcag cccccggcgc agcgcggccg cagcagcctc cgccccccgc acggtgtgag     60
cgcccgacgc ggccgaggcg gccggagtcc cgagctagcc ccggcggccg ccgccgccca    120
```

```
gaccggacga caggccacct cgtcggcgtc cgcccgagtc cccgcctcgc cgccaacgcc    180
acaaccaccg cgcacggccc cctgactccg tccagtattg atcgggagag ccggagcgag    240
ctcttcgggg agcagcgatg cgaccctccg ggacggccgg ggcagcgctc ctggcgctgc    300
tggctgcgct ctgcccggcg agtcgggctc tggaggaaaa gaaagtttgc caaggcacga    360
gtaacaagct cacgcagttg ggcacttttg aagatcattt tctcagcctc cagaggatgt    420
tcaataactg tgaggtggtc cttgggaatt tggaaattac ctatgtgcag aggaattatg    480
atctttcctt cttaaagacc atccaggagg tggctggtta tgtcctcatt gccctcaaca    540
cagtggagcg aattcctttg gaaaacctgc agatcatcag aggaaatatg tactacgaaa    600
attcctatgc cttagcagtc ttatctaact atgatgcaaa taaaaccgga ctgaaggagc    660
tgcccatgag aaatttacag gaaatcctgc atggcgccgt gcggttcagc aacaaccctg    720
ccctgtgcaa cgtggagagc atccagtggc gggacatagt cagcagtgac tttctcagca    780
acatgtcgat ggacttccag aaccacctgg gcagctgcca aaagtgtgat ccaagctgtc    840
ccaatgggag ctgctggggt gcaggagagg agaactgcca gaaactgacc aaaatcatct    900
gtgcccagca gtgctccggg cgctgccgtg gcaagtcccc cagtgactgc tgccacaacc    960
agtgtgctgc aggctgcaca ggcccccggg agagcgactg cctggtctgc cgcaaattcc   1020
gagacgaagc cacgtgcaag gacacctgcc ccccactcat gctctacaac cccaccacgt   1080
accagatgga tgtgaacccc gagggcaaat acagctttgg tgccacctgc gtgaagaagt   1140
gtccccgtaa ttatgtggtg acagatcacg gctcgtgcgt ccgagcctgt ggggccgaca   1200
gctatgagat ggaggaagac ggcgtccgca agtgtaagaa gtgcgaaggg ccttgccgca   1260
aagtgtgtaa cggaataggt attggtgaat ttaaagactc actctccata aatgctacga   1320
atattaaaca cttcaaaaac tgcacctcca tcagtggcga tctccacatc ctgccggtgg   1380
catttagggg tgactccttc acacatactc ctcctctgga tccacaggaa ctggatattc   1440
tgaaaaccgt aaaggaaatc acagggtttt tgctgattca ggcttggcct gaaaacagga   1500
cggacctcca tgcctttgag aacctagaaa tcatacgcgg caggaccaag caacatggtc   1560
agttttctct tgcagtcgtc agcctgaaca taacatcctt gggattacgc tccctcaagg   1620
agataagtga tggagatgtg ataatttcag gaaacaaaaa tttgtgctat gcaaatacaa   1680
taaactggaa aaaactgttt gggacctccg gtcagaaaac caaaattata agcaacagag   1740
gtgaaaacag ctgcaaggcc acaggccagg tctgccatgc cttgtgctcc cccgagggct   1800
gctgggcccc ggagcccagg gactgcgtct cttgccggaa tgtcagccga gcagggaat   1860 gcgtggacaa gtgcaacctt ctggagggtg agccaaggga gtttgtggag aactctgagt   1920
gcatacagtg ccacccagag tgcctgcctc aggccatgaa catcacctgc acaggacggg   1980
gaccagacaa ctgtatccag tgtgcccact acattgacgg cccccactgc gtcaagacct   2040
gcccggcagg agtcatggga gaaaacaaca cctggtctg gaagtacgca gacgccggcc   2100
atgtgtgcca cctgtgccat ccaaactgca cctacggatg cactgggcca ggtcttgaag   2160
gctgtccaac gaatgggcct aagatcccgt ccatcgccac tgggatggtg ggggccctcc   2220
tcttgctgct ggtggtggcc ctgggatcg gcctcttcat gcgaaggcgc cacatcgttc   2280
ggaagcgcac gctgcggagg ctgctgcagg agagggagct tgtggagcct cttacaccca   2340
gtggagaagc tcccaaccaa gctctcttga ggatcttgaa ggaaactgaa ttcaaaaaga   2400
tcaaagtgct gggctccggt gcgttcggca cggtgtataa gggactctgg atcccagaag   2460
```

```
gtgagaaagt taaaattccc gtcgctatca aggaattaag agaagcaaca tctccgaaag    2520
ccaacaagga atcctcgat gaagcctacg tgatggccag cgtggacaac ccccacgtgt    2580
gccgcctgct gggcatctgc ctcacctcca ccgtgcagct catcacgcag ctcatgccct    2640
tcggctgcct cctggactat gtccgggaac acaaagacaa tattggctcc cagtacctgc    2700
tcaactggtg tgtgcagatc gcaaagggca tgaactactt ggaggaccgt cgcttggtgc    2760
accgcgacct ggcagccagg aacgtactgg tgaaaacacc gcagcatgtc aagatcacag    2820
attttgggct ggccaaactg ctgggtgcgg aagagaaaga ataccatgca gaaggaggca    2880
aagtgcctat caagtggatg gcattggaat caattttaca cagaatctat acccaccaga    2940
gtgatgtctg gagctacggg gtgactgttt gggagttgat gacctttgga tccaagccat    3000
atgacggaat ccctgccagc gagatctcct ccatcctgga gaaggagaa cgcctcccct    3060 agccacccat atgtaccatc gatgtctaca tgatcatggt caagtgctgg atgatagacg    3120
cagatagtcg cccaaagttc cgtgagttga tcatcgaatt ctccaaaatg gcccgagacc    3180
cccagcgcta ccttgtcatt cagggggatg aaagaatgca tttgccaagt cctacagact    3240
ccaacttcta ccgtgccctg atggatgaag aagacatgga cgacgtggtg gatgccgacg    3300
agtacctcat cccacagcag ggcttcttca gcagcccctc cacgtcacgg actccctcc    3360 tgagctctct gagtgcaacc agcaacaatt ccaccgtggc ttgcattgat agaaatgggc    3420
tgcaaagctg tccatcaag gaagacagct tcttgcagcg atacagctca gcccccacag    3480
gcgccttgac tgaggacagc atagacgaca ccttcctccc agtgcctgaa tacataaacc    3540
agtccgttcc caaaaggccc gctggctctg tgcagaatcc tgtctatcac aatcagcctc    3600
tgaaccccgc gcccagcaga gacccacact accaggaccc ccacagcact gcagtgggca    3660
accccgagta tctcaacact gtccagccca ctgtgtcaa cagcacattc gacagccctg    3720
cccactgggc ccagaaaggc agccaccaaa ttagcctgga caaccctgac taccagcagg    3780
acttctttcc caaggaagcc aagccaaatg gcatctttaa gggctccaca gctgaaaatg    3840
cagaatacct aagggtcgcg ccacaaagca gtgaatttat tggagcatga ccacggagga    3900
tagtatgagc cctaaaaatc cagactcttt cgatacccag gaccaagcca cagcaggtcc    3960
tccatcccaa cagccatgcc cgcattagct cttagaccca cagactggtt ttgcaacgtt    4020
tacaccgact agccaggaag tacttccacc tcgggcacat tttgggaagt tgcattcctt    4080
tgtcttcaaa ctgtgaagca tttacagaaa cgcatccagc aagaatattg tccctttgag    4140
cagaaattta tcttcaaag aggtatattt gaaaaaaaaa aaagtatat gtgaggattt    4200 ttattgattg gggatcttgg agtttttcat tgtcgctatt gattttact tcaatgggct    4260 cttccaacaa ggaagaagct tgctggtagc acttgctacc ctgagttcat ccaggcccaa    4320
ctgtgagcaa ggagcacaag ccacaagtct tccagaggat gcttgattcc agtggttctg    4380
cttcaaggct tccactgcaa aacactaaag atccaagaag gccttcatgg ccccagcagg    4440
ccggatcggt actgtatcaa gtcatggcag gtacagtagg ataagccact ctgtcccttc    4500
ctgggcaaag aagaaacgga ggggatggaa ttcttcctta gacttacttt tgtaaaaatg    4560
tccccacggt acttactccc cactgatgga ccagtggttt ccagtcatga gcgttagact    4620
gacttgtttg tcttccattc cattgttttg aaactcagta tgctgcccct gtcttgctgt    4680
catgaaatca gcaagagagg atgacacatc aaataataac tcggattcca gcccacattg    4740
gattcatcag catttggacc aatagcccac agctgagaat gtggaatacc taaggatagc    4800
accgcttttg ttctcgcaaa aacgtatctc ctaatttgag gctcagatga aatgcatcag    4860
```

```
gtcctttggg gcatagatca gaagactaca aaaatgaagc tgctctgaaa tctccttag    4920
ccatcacccc aaccccccaa aattagtttg tgttacttat ggaagatagt tttctccttt    4980
tacttcactt caaaagcttt ttactcaaag agtatatgtt ccctccaggt cagctgcccc    5040
caaacccct ccttacgctt tgtcacacaa aaagtgtctc tgccttgagt catctattca     5100
agcacttaca gctctggcca acagggca ttttacaggt gcgaatgaca gtagcattat      5160
gagtagtgtg gaattcaggt agtaaatatg aaactagggt ttgaaattga taatgctttc    5220
acaacatttg cagatgtttt agaaggaaaa aagttccttc ctaaaataat ttctctacaa    5280
ttggaagatt ggaagattca gctagttagg agcccacctt ttttcctaat ctgtgtgtgc    5340
cctgtaacct gactggttaa cagcagtcct ttgtaaacag tgtttaaac tctcctagtc     5400
aatatccacc ccatccaatt tatcaaggaa gaaatggttc agaaaatatt ttcagcctac    5460
agttatgttc agtcacacac acatacaaaa tgttccttt gcttttaaag taattttga     5520
ctcccagatc agtcagagcc cctacagcat tgttaagaaa gtatttgatt tttgtctcaa    5580
tgaaaataaa actatattca tttccactct attatgctct caaataccc taagcatcta    5640
tactagcctg gtatgggtat gaagataca aagataaata aaacatagtc cctgattcta    5700
agaaattcac aatttagcaa aggaaatgga ctcatagatg ctaaccttaa aacaacgtga    5760
caaatgccag acaggaccca tcagccaggc actgtgagag cacagagcag ggaggttggg    5820
tcctgcctga ggagacctgg aagggaggcc tcacaggagg atgaccaggt ctcagtcagc    5880
ggggaggtgg aaagtgcagg tgcatcaggg gcaccctgac cgaggaaaca gctgccagag    5940
gcctccactg ctaaagtcca cataaggctg aggtcagtca ccctaaacaa cctgctccct    6000
ctaagccagg ggatgagctt ggagcatccc acaagttccc taaagttgc agccccagg      6060
gggattttga gctatcatct ctgcacatgc ttagtgagaa gactacacaa catttctaag    6120
aatctgagat tttatattgt cagttaacca ctttcattat tcattcacct caggacatgc    6180
agaaatattt cagtcagaac tgggaaacag aaggacctac attctgctgt cacttatgtg    6240
tcaagaagca gatgatcgat gaggcaggtc agttgtaagt gagtcacatt gtagcattaa    6300
attctagtat ttttgtagtt tgaaacagta acttaataaa agagcaaaag ctaaaaaaaa    6360
aaaaaaaaa                                                            6369
```

<210> SEQ ID NO 4
<211> LENGTH: 1210
<212> TYPE: PRT
<213> ORGANISM: Artificial
<220> FEATURE:
<223> OTHER INFORMATION: Synthetic

<400> SEQUENCE: 4

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
```

```
                85                  90                  95
Glu Arg Ile Pro Leu Glu Asn Leu Gln Ile Ile Arg Gly Asn Met Tyr
                100                 105                 110
Tyr Glu Asn Ser Tyr Ala Leu Ala Val Leu Ser Asn Tyr Asp Ala Asn
                115                 120                 125
Lys Thr Gly Leu Lys Glu Leu Pro Met Arg Asn Leu Gln Glu Ile Leu
                130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
                180                 185                 190
Ser Cys Pro Asn Gly Ser Cys Trp Gly Ala Gly Glu Glu Asn Cys Gln
                195                 200                 205
Lys Leu Thr Lys Ile Ile Cys Ala Gln Gln Cys Ser Gly Arg Cys Arg
                210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
                260                 265                 270
Thr Thr Tyr Gln Met Asp Val Asn Pro Glu Gly Lys Tyr Ser Phe Gly
                275                 280                 285
Ala Thr Cys Val Lys Lys Cys Pro Arg Asn Tyr Val Val Thr Asp His
                290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
                370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
                435                 440                 445
Gly Leu Arg Ser Leu Lys Glu Ile Ser Asp Gly Asp Val Ile Ile Ser
                450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
```

```
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
                610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
                675                 680                 685
Val Glu Pro Leu Thr Pro Ser Gly Glu Ala Pro Asn Gln Ala Leu Leu
                690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
                755                 760                 765
Val Asp Asn Pro His Val Cys Arg Leu Leu Gly Ile Cys Leu Thr Ser
                770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
                835                 840                 845
Gln His Val Lys Ile Thr Asp Phe Gly Leu Ala Lys Leu Leu Gly Ala
                850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
                915                 920                 925
```

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 5
<211> LENGTH: 5700
<212> TYPE: DNA
<213> ORGANISM: Artificial
<220> FEATURE:
<223> OTHER INFORMATION: Synthetic

<400> SEQUENCE: 5
aaaaagagaa actgttggga gaggaatcgt atctccatat ttcttctttc agccccaatc      60
caagggttgt agctggaact ttccatcagt tcttcctttc ttttttcctct ctaagccttt    120 gccttgctct gtcacagtga agtcagccag agcagggctg ttaaactctg tgaaatttgt    180
cataagggtg tcaggtattt cttactggct tccaaagaaa catagataaa gaaatctttc    240
ctgtggcttc ccttggcagg ctgcattcag aaggtctctc agttgaagaa agagcttgga    300
ggacaacagc acaacaggag agtaaaagat gccccagggc tgaggcctcc gctcaggcag    360

-continued

```
ccgcatctgg ggtcaatcat actcaccttg cccgggccat gctccagcaa aatcaagctg      420
tttctttttg aaagttcaaa ctcatcaaga ttatgctgct cactcttatc attctgttgc      480
cagtagtttc aaaatttagt tttgttagtc tctcagcacc gcagcactgg agctgtcctg      540
aaggtactct cgcaggaaat gggaattcta cttgtgtggg tcctgcaccc ttcttaattt      600
tctcccatgg aaatagtatc tttaggattg acacagaagg aaccaattat gagcaattgg      660
tggtggatgc tggtgtctca gtgatcatgg attttcatta taatgagaaa agaatctatt      720
gggtggattt agaaagacaa cttttgcaaa gagttttttct gaatgggtca aggcaagaga     780
gagtatgtaa tatagagaaa aatgtttctg gaatggcaat aaattggata aatgaagaag      840
ttatttggtc aaatcaacag gaaggaatca ttacagtaac agatatgaaa ggaaataatt      900
cccacattct tttaagtgct ttaaaatatc ctgcaaatgt agcagttgat ccagtagaaa      960
ggtttatatt ttggtcttca gaggtggctg gaagccttta tagagcagat ctcgatggtg     1020
tgggagtgaa ggctctgttg gagacatcag agaaaataac agctgtgtca ttggatgtgc     1080
ttgataagcg gctgttttgg attcagtaca acagagaagg aagcaattct cttatttgct     1140
cctgtgatta tgatggaggt tctgtccaca ttagtaaaca tccaacacag cataatttgt     1200
ttgcaatgtc cctttttggt gaccgtatct tctattcaac atggaaaatg aagacaattt     1260
ggatagccaa caaacacact ggaaaggaca tggttagaat taacctccat tcatcatttg     1320
taccacttgg tgaactgaaa gtagtgcatc cacttgcaca acccaaggca gaagatgaca     1380
cttgggagcc tgagcagaaa ctttgcaaat tgaggaaagg aaactgcagc agcactgtgt     1440
gtgggcaaga cctccagtca cacttgtgca tgtgtgcaga gggatacgcc ctaagtcgag     1500
accggaagta ctgtgaagat gttaatgaat gtgcttttttg gaatcatggc tgtactcttg     1560
ggtgtaaaaa cacccctgga tcctattact gcacgtgccc tgtaggattt gttctgcttc     1620
ctgatgggaa acgatgtcat caacttgttt cctgtccacg caatgtgtct gaatgcagcc     1680
atgactgtgt tctgacatca gaaggtcccct tatgtttctg tcctgaaggc tcagtgcttg     1740
agagagatgg gaaaacatgt agcggttgtt cctcacccga taatggtgga tgtagccagc     1800
tctgcgttcc tctagcccca gtatcctggg aatgtgattg cttttcctggg tatgacctac     1860 aactggatga aaaaagctgt gcagcttcag gaccacaacc atttttgctg tttgccaatt     1920
ctcaagatat tcgacacatg cattttgatg aacagactca tggaactctg ctcagccagc     1980
agatgggaat ggtttatgcc ctagatcatg accctgtgga aaataagata tactttgccc     2040 atacagcct gaagtggata gagagagcta atatggatgg ttcccagcga gaaaggcttta   2100 tgaggaagg agtagatgtg ccagaaggtc ttgctgtgga ctggattggc cgtagattct      2160
attggacaga cagagggaaa tctctgattg aaggagtgaa tttaaatggg aaacgttcca     2220
aaataatcac taaggagaac atctctcaac cacgaggaat tgctgttcat ccaatggcca     2280
agagattatt ctggactgat acagggatta atccacgaat tgaaagttct tccctccaag     2340
gccttggccg tctggttata gccagctctg atctaatctg gccagtgga ataacgattg       2400 acttcttaac tgacaagttg tactggtgcg atgccaagca gtctgtgatt gaaatggcca     2460
atctggatgg ttcaaaacgc cgaagactta cccagaatga tgtaggtcac ccatttgctg     2520
tagcagtgtt tgaggattat gtgtggttct cagattgggc tatgccatca gtaatgagag     2580
taaacaagag gactggcaaa gatagagtac gtctccaagg cagcatgctg aagccctcat     2640
cactggttgt ggttcatcca ttggcaaaac caggagcaga tccctgctta tatcaaaacg     2700
gaggctgtga acatatttgc aaaaagaggc ttggaactgc ttggtgttcg tgtcgtgaag     2760
```

```
gttttatgaa agcctcagat gggaaaacgt gtctggctct ggatggtcat cagctgttgg    2820
caggtggtga agttgatcta aagaaccaag taacaccatt ggacatcttg tccaagacta    2880
gagtgtcaga agataacatt acagaatctc aacacatgct agtggctgaa atcatggtgt    2940
cagatcaaga tgactgtgct cctgtgggat gcagcatgta tgctcggtgt atttcagagg    3000
gagaggatgc cacatgtcag tgtttgaaag gatttgctgg ggatggaaaa ctatgttctg    3060
atatagatga atgtgagatg ggtgtcccag tgtgcccccc tgcctcctcc aagtgcatca    3120
acaccgaagg tggttatgtc tgccggtgct cagaaggcta ccaaggagat gggattcact    3180
gtcttgatat tgatgagtgc caactggggg agcacagctg tggagagaat gccagctgca    3240
caaatacaga gggaggctat acctgcatgt gtgctggacg cctgtctgaa ccaggactga    3300
tttgccctga ctctactcca cccctcacc tcagggaaga tgaccaccac tattccgtaa    3360
gaaatagtga ctctgaatgt cccctgtccc acgatgggta ctgcctccat gatggtgtgt    3420
gcatgtatat tgaagcattg acaagtatg catgcaactg tgttgttggc tacatcgggg    3480
agcgatgtca gtaccgagac ctgaagtggt gggaactgcg ccacgctggc cacgggcagc    3540
agcagaaggt catcgtggtg gctgtctgcg tggtggtgct tgtcatgctg ctcctcctga    3600
gcctgtgggg ggcccactac tacaggactc agaagctgct atcgaaaaac ccaaagaatc    3660
cttatgagga gtcgagcaga gatgtgagga gtcgcaggcc tgctgacact gaggatggga    3720
tgtcctcttg ccctcaacct tggtttgtgg ttataaaaga caccaagac ctcaagaatg    3780 ggggtcaacc agtggctggt gaggatggcc aggcagcaga tgggtcaatg caaccaactt    3840
catggaggca ggagcccag ttatgtggaa tgggcacaga gcaaggctgc tggattccag    3900
tatccagtga taagggctcc tgtccccagg taatggagcg aagctttcat atgccctcct    3960
atgggacaca gaccccttgaa gggggtgtcg agaagcccca ttctctccta tcagctaacc    4020
cattatggca caaagggcc ctggaccac cacaccaaat ggagctgact cagtgaaaac    4080
tggaattaaa aggaaagtca agaagaatga actatgtcga tgcacagtat cttttctttc    4140
aaaagtagag caaaactata ggttttggtt ccacaatctc tacgactaat cacctactca    4200
atgcctggag acagatacgt agttgtgctt ttgtttgctc ttttaagcag tctcactgca    4260
gtcttatttc caagtaagag tactgggaga atcactaggt aacttattag aaacccaaat    4320
tgggacaaca gtgctttgta aattgtgttg tcttcagcag tcaatacaaa tagattttg    4380 ttttttgttgt tcctgcagcc ccagaagaaa ttagggggtta aagcagacag tcacactggt    4440
ttggtcagtt acaaagtaat ttctttgatc tggacagaac atttatatca gtttcatgaa    4500
atgattggaa tattacaata ccgttaagat acagtgtagg catttaactc ctcattggcg    4560
tggtccatgc tgatgatttt gcaaaatgag ttgtgatgaa tcaatgaaaa atgtaattta    4620
gaaactgatt tcttcagaat tagatggctt attttttaaa atatttgaat gaaaacattt    4680
tatttttaaa atattacaca ggaggcttcg gagtttctta gtcattactg tccttttccc    4740
ctacagaatt ttccctcttg gtgtgattgc acagaatttg tatgtatttt cagttacaag    4800
attgtaagta aattgcctga tttgttttca ttatagacaa cgatgaattt cttctaatta    4860
tttaaataaa atcaccaaaa acataaacat tttattgtat gcctgattaa gtagttaatt    4920
atagtctaag gcagtactag agttgaacca aaatgatttg tcaagcttgc tgatgtttct    4980 gttttttcgtt tttttttttt ttccggagag aggataggag ctcactctgt tatccaggct    5040
ggagtgtgca atggcacaat catagctcag tgcagcctca aactcctggg ctcaagcaat    5100
```

-continued

| | |
|---|---|
| cctcctgcct cagcctcccg agtaactagg accacaggca caggccacca tgcctggcta | 5160 |
| aggtttttat tttttatttt tgtagacatg gggatcacac aatgttgccc aggctggtct | 5220 |
| tgaactcctg gcctcaagca aggtcgtgct ggtaattttg caaaatgaat tgtgattgac | 5280 |
| tttcagcctc ccaacgtatt agattatagg cattagccat ggtgcccagc cttgtaactt | 5340 |
| ttaaaaaaat tttttaatct acaactctgt agattaaaat ttcacatggt gttctaatta | 5400 |
| aatattttc ttgcagccaa gatattgtta ctacagataa cacaacctga tatggtaact | 5460 |
| ttaaattttg ggggctttga atcattcagt ttatgcatta actagtccct ttgtttatct | 5520 |
| ttcatttctc aacccccttgt actttggtga taccagacat cagaataaaa agaaattgaa | 5580 |
| gtacctgttt tcaaatggat actttatagg aattttggta aagatttggt gatgggagga | 5640 |
| tgacttgagg tttgtggata ttagttaatt attcagtatg atacctcacc cagctaattt | 5700 |

<210> SEQ ID NO 6
<211> LENGTH: 1207
<212> TYPE: PRT
<213> ORGANISM: Artificial
<220> FEATURE:
<223> OTHER INFORMATION: Synthetic

<400> SEQUENCE: 6

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala

```
                260                 265                 270
Asn Lys His Thr Gly Lys Asp Met Val Arg Ile Asn Leu His Ser Ser
            275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
    355                 360                 365

Leu Gly Cys Lys Asn Thr Pro Gly Ser Tyr Tyr Cys Thr Cys Pro Val
370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
    435                 440                 445

Gln Leu Cys Val Pro Leu Ser Pro Val Ser Trp Glu Cys Asp Cys Phe
450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
    515                 520                 525

Ala His Thr Ala Leu Lys Trp Ile Glu Arg Ala Asn Met Asp Gly Ser
530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
    595                 600                 605

Ala Lys Arg Leu Phe Trp Thr Asp Thr Gly Ile Asn Pro Arg Ile Glu
610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Arg Leu Thr Gln Asn Asp Val Gly His Pro Phe
    675                 680                 685
```

```
Ala Val Ala Val Phe Glu Asp Tyr Val Trp Phe Ser Asp Trp Ala Met
    690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val His Pro
                725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
    770                 775                 780

Gly His Gln Leu Leu Ala Gly Gly Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
        835                 840                 845

Glu Gly Glu Asp Ala Thr Cys Gln Cys Leu Lys Gly Phe Ala Gly Asp
    850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Glu His Ser Cys Gly Glu Asn Ala Ser
        915                 920                 925

Cys Thr Asn Thr Glu Gly Gly Tyr Thr Cys Met Cys Ala Gly Arg Leu
    930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg
    1010                1015                1020

His Ala Gly His Gly Gln Gln Lys Val Ile Val Ala Val
    1025                1030                1035

Cys Val Val Leu Val Met Leu Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095
```

| | | | | | | | | | | | | |
|---|---|---|---|---|---|---|---|---|---|---|---|---|
|Val|Val|Ile|Lys|Glu|His|Gln|Asp|Leu|Lys|Asn|Gly|Gly|Gln|Pro|
| |1100| | | | |1105| | | | |1110| | | |

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

```
<210> SEQ ID NO 7
<211> LENGTH: 2106
<212> TYPE: DNA
<213> ORGANISM: Artificial
<220> FEATURE:
<223> OTHER INFORMATION: Synthetic

<400> SEQUENCE: 7
gagcccttgg accaaactcg cctgcgccga gagccgtccg cgtagagcgc tccgtctccg    60
gcgagatgtc cgagcgcaaa gaaggcagag gcaaagggaa gggcaagaag aaggagcgag   120
gctccggcaa gaagccggag tccgcggcgg gcagccagag cccagccttg cctccccaat   180
tgaaagagat gaaaagccag gaatcggctg caggttccaa actagtcctt cggtgtgaaa   240
ccagttctga atactcctct ctcagattca gtggttcaa gaatgggaat gaattgaatc    300
gaaaaaacaa accacaaaat atcaagatac aaaaaaagcc agggaagtca gaacttcgca    360
ttaacaaagc atcactggct gattctggag agtatatgtg caaagtgatc agcaaattag   420
gaaatgacag tgcctctgcc aatatcacca tcgtggaatc aaacgagatc atcactggta   480
tgccagcctc aactgaagga gcatatgtgt cttcagagtc tcccattaga atatcagtat   540
ccacagaagg agcaaatact tcttcatcta catctacatc caccactggg acaagccatc   600
ttgtaaaatg tgcggagaag gagaaaactt tctgtgtgaa tggaggggag tgcttcatgg   660
tgaaagacct ttcaaacccc tcagatact tgtgcaagtg ccaacctgga ttcactggag   720
caagatgtac tgagaatgtg cccatgaaag tccaaaacca agaaaaggcg gaggagctgt   780
accagaagag agtgctgacc ataaccggca tctgcatcgc cctccttgtg gtcggcatca   840 tgtgttttggt ggcctactgc aaaaccaaga acagcggaa aaagctgcat gaccgtcttc    900
ggcagagcct tcggtctgaa cgaaacaata tgatgaacat tgccaatggg cctcaccatc   960
ctaacccacc cccgagaat gtccagctgg tgaatcaata cgtatctaaa aacgtcatct    1020
ccagtgagca tattgttgag agagaagcag agacatcctt ttccaccagt cactatactt   1080
ccacagccca tcactccact actgtcaccc agactcctag ccacagctgg agcaacggac   1140
acactgaaag catcctttcc gaaagccact ctgtaatcgt gatgtcatcc gtagaaaaca   1200
gtaggcacag cagcccaact gggggcccaa gaggacgtct taatggcaca ggaggccctc   1260
gtgaatgtaa cagcttcctc aggcatgcca gagaaacccc tgattcctac cgagactctc   1320
ctcatagtga aggtatgtg tcagccatga ccaccccggc tcgtatgtca cctgtagatt    1380
```

```
tccacacgcc aagctccccc aaatcgcccc cttcggaaat gtctccaccc gtgtccagca   1440
tgacggtgtc catgccttcc atggcggtca gccccttcat ggaagaagag agacctctac   1500
ttctcgtgac accaccaagg ctgcgggaga agaagtttga ccatcaccct cagcagttca   1560
gctccttcca ccacaacccc gcgcatgaca gtaacagcct ccctgctagc cccttgagga   1620
tagtggagga tgaggagtat gaaacgaccc aagagtacga gccagcccaa gagcctgtta   1680
agaaactcgc caatagccgg cgggccaaaa gaaccaagcc caatggccac attgctaaca   1740
gattggaagt ggacagcaac acaagctccc agagcagtaa ctcagagagt gaaacagaag   1800
atgaaagagt aggtgaagat acgccttttcc tgggcataca gaaccccctg gcagccagtc   1860
ttgaggcaac acctgccttc cgcctggctg acagcaggac taacccagca ggccgcttct   1920
cgacacagga gaaatccag gccaggctgt ctagtgtaat tgctaaccaa gaccctattg   1980
ctgtataaaa cctaaataaa cacatagatt cacctgtaaa actttatttt atataataaa   2040
gtattccacc ttaaattaaa caatttattt tattttagca gttctgcaaa tagaaaacag   2100
gaaaaa                                                              2106
```

<210> SEQ ID NO 8
<211> LENGTH: 640
<212> TYPE: PRT
<213> ORGANISM: Artificial
<220> FEATURE:
<223> OTHER INFORMATION: Synthetic

<400> SEQUENCE: 8

```
Met Ser Glu Arg Lys Glu Gly Arg Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Gln Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Gln Pro Gly Phe Thr Gly Ala Arg Cys Thr Glu Asn
    210                 215                 220
```

```
Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
            245                 250                 255

Gly Ile Met Cys Leu Val Ala Tyr Cys Lys Thr Lys Lys Gln Arg Lys
        260                 265                 270

Lys Leu His Asp Arg Leu Arg Gln Ser Leu Arg Ser Glu Arg Asn Asn
    275                 280                 285

Met Met Asn Ile Ala Asn Gly Pro His His Pro Asn Pro Pro Pro Glu
290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
            340                 345                 350

His Ser Trp Ser Asn Gly His Thr Glu Ser Ile Leu Ser Glu Ser His
        355                 360                 365

Ser Val Ile Val Met Ser Ser Val Glu Asn Ser Arg His Ser Ser Pro
370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415

Asp Ser Pro His Ser Glu Arg Tyr Val Ser Ala Met Thr Thr Pro Ala
            420                 425                 430

Arg Met Ser Pro Val Asp Phe His Thr Pro Ser Ser Pro Lys Ser Pro
        435                 440                 445

Pro Ser Glu Met Ser Pro Pro Val Ser Ser Met Thr Val Ser Met Pro
    450                 455                 460

Ser Met Ala Val Ser Pro Phe Met Glu Glu Arg Pro Leu Leu Leu
465                 470                 475                 480

Val Thr Pro Pro Arg Leu Arg Glu Lys Lys Phe Asp His His Pro Gln
                485                 490                 495

Gln Phe Ser Ser Phe His His Asn Pro Ala His Asp Ser Asn Ser Leu
            500                 505                 510

Pro Ala Ser Pro Leu Arg Ile Val Glu Asp Glu Glu Tyr Glu Thr Thr
        515                 520                 525

Gln Glu Tyr Glu Pro Ala Gln Glu Pro Val Lys Lys Leu Ala Asn Ser
    530                 535                 540

Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
            580                 585                 590

Asn Pro Leu Ala Ala Ser Leu Glu Ala Thr Pro Ala Phe Arg Leu Ala
        595                 600                 605

Asp Ser Arg Thr Asn Pro Ala Gly Arg Phe Ser Thr Gln Glu Glu Ile
    610                 615                 620

Gln Ala Arg Leu Ser Ser Val Ile Ala Asn Gln Asp Pro Ile Ala Val
625                 630                 635                 640
```

<210> SEQ ID NO 9
<211> LENGTH: 6661
<212> TYPE: DNA
<213> ORGANISM: Artificial
<220> FEATURE:
<223> OTHER INFORMATION: Synthetic

<400> SEQUENCE: 9

| | | | | | |
|---|---|---|---|---|---|
| ggcttaactg | atgcctgcct | gcctctcttt | gatttgatgg | cctttattcc | ttctaattgg | 60 |
| ataaaatagg | aagtcactgg | cagtcctgtg | tggctgggga | tactgatttt | actcagacca | 120 |
| gcctgcagct | ctagagtgtg | ggtagagagc | ggggagtggg | ggttgggaga | gggggaggaa | 180 |
| agagagagag | gagagaggac | gggcttggat | gaagaaggga | agaaagaga | aagagactga | 240 |
| agcagagaag | agccgcagag | gaagaaagtg | aatgagcact | caagaaggac | aaagaggagt | 300 |
| agtcgggggt | ggggtggagg | cagggcgggg | aagggagtga | ccgcccctcc | tggctgcact | 360 |
| cttgcctccg | gagccctctg | atcctgtttg | cagtgatgct | ccgagggcag | gcacctgctg | 420 |
| ctctgtaatg | attcagcccc | tttcagccgt | cgtcgcgtta | acacaacagg | atgctgttgc | 480 |
| tattgtcact | actgcctctc | ctgccgccgc | tgctgctgcc | gccgccgcca | ccgccgctgg | 540 |
| tcctccttct | gcttttactt | ctcctgcatg | acagttgttt | tcttcatctg | agcagacacc | 600 |
| agcttcagat | gctcgaggtg | agaaacatgc | ctttcagttt | gggctactgg | tttacttaat | 660 |
| taatcagccg | gcagctccgt | cgatctattt | tcgtccctgt | cctcttgacg | agcccgggat | 720 |
| ggtttggagt | agcatttaaa | agaactagaa | aagtggccca | gaaacagcag | cttaaagaat | 780 |
| tattacgata | tactttgatt | ttgtagttgc | taggagcttt | tcttcccccc | ttgcatcttt | 840 |
| ctgaactctt | cttgatttta | ataatggcct | tggacttgga | cgatttatcg | atttcccct | 900 |
| gtaagatgct | gtatcatttg | gttgggggg | cctctgcgtg | gtaatggacc | gtgagagcgg | 960 |
| ccaggccttc | ttctggaggt | gagccgatgg | agatttattc | cccagacatg | tctgaggtcg | 1020 |
| ccgccgagag | gtcctccagc | ccctccactc | agctgagtgc | agaccatct | cttgatgggc | 1080 |
| ttccggcagc | agaagacatg | ccagagcccc | agactgaaga | tgggagaacc | cctggactcg | 1140 |
| tgggcctggc | cgtgccctgc | tgtgcgtgcc | tagaagctga | gcgcctgaga | ggttgcctca | 1200 |
| actcagagaa | aatctgcatt | gtccccatcc | tggcttgcct | ggtcagcctc | tgcctctgca | 1260 |
| tcgccggcct | caagtgggta | tttgtggaca | agatctttga | atatgactct | cctactcacc | 1320 |
| ttgaccctgg | ggggttaggc | caggacccta | ttatttctct | ggacgcaact | gctgcctcag | 1380 |
| ctgtgtgggt | gtcgtctgag | gcatacactt | cacctgtctc | tagggctcaa | tctgaaagtg | 1440 |
| aggttcaagt | tacagtgcaa | ggtgacaagg | ctgttgtctc | ctttgaacca | tcagcggcac | 1500 |
| cgacaccgaa | gaatcgtatt | tttgcctttt | ctttcttgcc | gtccactgcg | ccatccttcc | 1560 |
| cttcacccac | ccggaaccct | gaggtgagaa | cgcccaagtc | agcaactcag | ccacaaacaa | 1620 |
| cagaaactaa | tctccaaact | gctcctaaac | tttctacatc | tacatccacc | actgggacaa | 1680 |
| gccatcttgt | aaaatgtgcg | gagaaggaga | aactttctg | tgtgaatgga | ggggagtgct | 1740 |
| tcatggtgaa | agacctttca | aaccccctcga | gatacttgtg | caagtgccca | aatgagttta | 1800 |
| ctggtgatcg | ctgccaaaac | tacgtaatgg | ccagcttcta | caagcatctt | gggattgaat | 1860 |
| ttatggaggc | ggaggagctg | taccagaaga | gagtgctgac | cataaccggc | atctgcatcg | 1920 |
| ccctccttgt | ggtcggcatc | atgtgtgtgg | tggcctactg | caaaaccaag | aaacagcgga | 1980 |
| aaaagctgca | tgaccgtctt | cggcagagcc | ttcggtctga | acgaaacaat | atgatgaaca | 2040 |
| ttgccaatgg | gcctcaccat | cctaacccac | cccccgagaa | tgtccagctg | gtgaatcaat | 2100 |

```
acgtatctaa aaacgtcatc tccagtgagc atattgttga gagagaagca gagacatcct   2160
tttccaccag tcactatact tccacagccc atcactccac tactgtcacc cagactccta   2220
gccacagctg gagcaacgga cacactgaaa gcatcctttc cgaaagccac tctgtaatcg   2280
tgatgtcatc cgtagaaaac agtaggcaca gcagcccaac tggggcccca agaggacgtc   2340
ttaatggcac aggaggccct cgtgaatgta acagcttcct caggcatgcc agagaaaccc   2400
ctgattccta ccgagactct cctcatagtg aaaggtatgt gtcagccatg accaccccgg   2460
ctcgtatgtc acctgtagat ttccacacgc caagctcccc caaatcgccc ccttcggaaa   2520
tgtctccacc cgtgtccagc atgacggtgt ccatgccttc catggcggtc agccccttca   2580
tggaagaaga gagacctcta cttctcgtga caccaccaag gctgcgggag aagaagtttg   2640
accatcaccc tcagcagttc agctccttcc accacaaccc cgcgcatgac agtaacagcc   2700
tccctgctag ccccttgagg atagtggagg atgaggagta tgaaacgacc caagagtacg   2760
agccagccca agagcctgtt aagaaactcg ccaatagccg gcgggccaaa agaaccaagc   2820
ccaatggcca cattgctaac agattggaag tggacagcaa cacaagctcc cagagcagta   2880
actcagagag tgaaacagaa gatgaaagag taggtgaaga tacgcctttc ctgggcatac   2940
agaaccccct ggcagccagt cttgaggcaa cacctgcctt ccgcctggct gacagcagga   3000
ctaacccagc aggccgcttc tcgacacagg aagaaatcca ggccaggctg tctagtgtaa   3060
ttgctaacca agaccctatt gctgtataaa acctaaataa acacatagat tcacctgtaa   3120
aactttattt tatataataa agtattccac cttaaattaa acaatttatt ttattttagc   3180
agttctgcaa atagaaaaca ggaaaaaaac ttttataaat taaatatatg tatgtaaaaa   3240
tgtgttatgt gccatatgta gcaattttttt acagtatttc aaaacgagaa agatatcaat   3300
ggtgcccttta tgttatgtta tgtcgagagc aagttttgta cagttacagt gattgctttt   3360
ccacagtatt tctgcaaaac ctctcataga ttcagttttt gctggcttct tgtgcattgc   3420
attatgatgt tgactggatg tatgatttgc aagacttgca actgtccctc tgtttgcttg   3480
tagtagcacc cgatcagtat gtcttgtaat ggcacatcca tccagatatg cctctcttgt   3540
gtatgaagtt ttcctttgctt tcagaatatg aaatgagttg tgtctactct gccagccaaa   3600
ggtttgcctc attgggctct gagataatag tagatccaac agcatgctac tattaaatac   3660
agcaagaaac tgcattaagt aatgttaaat attaggaaga aagtaatact gtgatttaaa   3720
aaaaactata ttattaatca gaagacagct tgctcttact aaaaggagct ctcatttact   3780
ttatttgatt ttattttttct tgacaaaaag caacagtttt agggatagct tagaaaatgg   3840
gttctggctt gctatcaggg taaatctaac accttacaag aggactgagt gtcactttct   3900
ctctggggga atgatccagc agcttatcta gttgacaatc aaaacacggc tgataaaggt   3960
gcaatcattt ctgacatgta ttttcactg attttgaagc tagtgattgg ttgtgtcttc   4020
ttggctcaaa aagaagcata ttacggcaca aaaagcccag cccagacagc acatgcagca   4080
ttttgtctga aatacttcta gagtcaaacg tgcctgctgt acatagcgat gacttgtcat   4140
cataggggaag tatttccatc gtagagtgtt cagaaggagt gactgtatag gtggagagaa   4200
gcttagtgac tccgttgaaa ttttaaaatg tggatgacca ccccttttctc cccttattt    4260
ttcttttatc tttccatgtt gccttgatca ggtcataact atgcatgaac attttttatc   4320
aggaatggcc gatgtgtatg tgatttgtaa tcacaagtaa tgattcatca ggaaatgtca   4380
atcctgttgg aaagattgca cctttacttg cagaagtgac ccccacctgt gtcctgacct   4440
ctccatttac aggctctctc acccatttcc cccacctcct ttaattttttg ctttactgtc   4500
```

```
ataaagtagg actaagattg gtctaagcat tgcatgttct tttgtgatgg taaatccaaa    4560
ggaaggccta taagtattaa catttgaaat aactgctaat tcaggaaaat ggaagaaaaa    4620
aaattatttg aaacacagaa cccatttcat ggcctgcctg atatctgtga atcagggct    4680 ggagctttac ttaggattca catggcctcc taggaaccat gggacaaatg ggaaacaggt    4740
tatcggggga ttcatgaagt cagtgagagt aattgcttct tttttgcggg tgaactgaat    4800
gtatttcttc accaaatctt gatgttaaca attaaaaaga agaaatgaca tgcaagtagg    4860
tcttagcaga aaaatgcagg ctgggcatga gtcatgttgt taccctccca catgctccta    4920
caatccacag atgcctgt ctgcaggttc ttgaagttat tgttagtatt tggtatctca    4980 aattttcgt cactgttcac atgccacttt ctctgtgcac agtggtatcc tcatttgctt    5040
tttaacctac actgaggagt ctttgtcagg ttgcactgat tttccaattc tgcagtaatg    5100
agtaagctca cggcatgggg aagaagacag tcagtccaat gaagttctct aaattatttt    5160
aacattgcct ttgaaggcct tgactcatcc ttagctattt caatgaagaa attcctacca    5220
tgaatttaaa accctaaaaa ttctgtttca aattctttgg gcattggggt actcagatat    5280
cccattgtgg aagaattta agaataaata gaagtttctg ttgagaacca tgagcaacat    5340
gtttcttaca atgagaattg ctatgcattt taaaattgca aatatatatg aaaattgaag    5400
acaagaggaa attgtatttc taacttgatt ctgatcactc acagaggtgg catattatta    5460
tagttgggac atcctttgca cccttcataa aaaaggccag ctgactgctc agcatcacct    5520
gccaaggcca ctagatttgt gtttacaggg gtatctctgt gatgcttgtc acatcactct    5580
tgaccacctc tgttaataaa ttccgacagt gcagtggcga tcggagtgtg aacttatgtt    5640
cccagcatat ggaaagctat cttaggtttt aaggtagtag aaattgccca ggagtttgac    5700
agcaactttg tttcccgggt ctaaaatcgt atcccactga ggtgtatgca gtggagcata    5760
atacatgcaa atacatgcaa aactccttt gtttcaccta agattcactt tctatcttac    5820
tttcccttcc tgcctagtgt gacttttgcc cccaagagtg cctggacagc attctagttt    5880
ctacaaaatg gtcctctgtg taggtgaatg tgtcccaaac ctgctatcac tttcttgttt    5940
cagtgtgact gtcttgttag aggtgaagtt tatccagggt aacttgctca ctaactattc    6000 cttttatgg cctggggtta aagggcgcat ggctcacact ggtgaaaata aggaaggcct    6060
ggtcttatct tgtattaata atactggctg cattccacca gccagagatt tctatctgcg    6120
aagacctatg aaacactgaa gagaaatgta ggcagaagga aatggccaca tatcacaagt    6180
tctattatat attcttttgt aaatacatat tgtatattac ttggatgttt tcttatatca    6240
tttactgtct ttttgagtta atgtcagttt ttactctctc aacttactat gtaacattgt    6300
aaataacata atgtccttta ttatttatat ttaagcatct aacatataga gttgttttca    6360
tataagttta agataaatgt caaaatata tgttcttttg tttttctttg ctttaaaatt    6420
atgtatcttt tccttttctt tttttaaga ataatttatt gttcaggaga agaatgtat    6480 atgtaactga aactatctga agaatgcaca ttgaaggccg tgaggtactg ataaactaaa    6540
gaatttatta ttcaaaatac taagcaataa gtaattgtga tttatttaaa gttttgtcca    6600
ttttccatga aagacatact gcaataaaaa tgctactctg tggaaaaaaa aaaaaaaaa    6660 a                                                                   6661
```

<210> SEQ ID NO 10
<211> LENGTH: 700
<212> TYPE: PRT

<213> ORGANISM: Artificial
<220> FEATURE:
<223> OTHER INFORMATION: Synthetic

<400> SEQUENCE: 10

Met Glu Ile Tyr Ser Pro Asp Met Ser Glu Val Ala Ala Glu Arg Ser
1               5                   10                  15

Ser Ser Pro Ser Thr Gln Leu Ser Ala Asp Pro Ser Leu Asp Gly Leu
            20                  25                  30

Pro Ala Ala Glu Asp Met Pro Glu Pro Gln Thr Glu Asp Gly Arg Thr
        35                  40                  45

Pro Gly Leu Val Gly Leu Ala Val Pro Cys Cys Ala Cys Leu Glu Ala
50                  55                  60

Glu Arg Leu Arg Gly Cys Leu Asn Ser Glu Lys Ile Cys Ile Val Pro
65                  70                  75                  80

Ile Leu Ala Cys Leu Val Ser Leu Cys Leu Cys Ile Ala Gly Leu Lys
                85                  90                  95

Trp Val Phe Val Asp Lys Ile Phe Glu Tyr Asp Ser Pro Thr His Leu
            100                 105                 110

Asp Pro Gly Gly Leu Gly Gln Asp Pro Ile Ile Ser Leu Asp Ala Thr
        115                 120                 125

Ala Ala Ser Ala Val Trp Val Ser Ser Glu Ala Tyr Thr Ser Pro Val
130                 135                 140

Ser Arg Ala Gln Ser Glu Ser Glu Val Gln Val Thr Val Gln Gly Asp
145                 150                 155                 160

Lys Ala Val Val Ser Phe Glu Pro Ser Ala Ala Pro Thr Pro Lys Asn
                165                 170                 175

Arg Ile Phe Ala Phe Ser Phe Leu Pro Ser Thr Ala Pro Ser Phe Pro
            180                 185                 190

Ser Pro Thr Arg Asn Pro Glu Val Arg Thr Pro Lys Ser Ala Thr Gln
        195                 200                 205

Pro Gln Thr Thr Glu Thr Asn Leu Gln Thr Ala Pro Lys Leu Ser Thr
        210                 215                 220

Ser Thr Ser Thr Thr Gly Thr Ser His Leu Val Lys Cys Ala Glu Lys
225                 230                 235                 240

Glu Lys Thr Phe Cys Val Asn Gly Gly Glu Cys Phe Met Val Lys Asp
                245                 250                 255

Leu Ser Asn Pro Ser Arg Tyr Leu Cys Lys Cys Pro Asn Glu Phe Thr
            260                 265                 270

Gly Asp Arg Cys Gln Asn Tyr Val Met Ala Ser Phe Tyr Lys His Leu
        275                 280                 285

Gly Ile Glu Phe Met Glu Ala Glu Glu Leu Tyr Gln Lys Arg Val Leu
        290                 295                 300

Thr Ile Thr Gly Ile Cys Ile Ala Leu Leu Val Val Gly Ile Met Cys
305                 310                 315                 320

Val Val Ala Tyr Cys Lys Thr Lys Lys Gln Arg Lys Lys Leu His Asp
                325                 330                 335

Arg Leu Arg Gln Ser Leu Arg Ser Glu Arg Asn Asn Met Met Asn Ile
            340                 345                 350

Ala Asn Gly Pro His His Pro Asn Pro Pro Glu Asn Val Gln Leu
        355                 360                 365

Val Asn Gln Tyr Val Ser Lys Asn Val Ile Ser Ser Glu His Ile Val
        370                 375                 380

Glu Arg Glu Ala Glu Thr Ser Phe Ser Thr Ser His Tyr Thr Ser Thr

```
                385                 390                 395                 400
Ala His His Ser Thr Thr Val Thr Gln Thr Pro Ser His Ser Trp Ser
                    405                 410                 415

Asn Gly His Thr Glu Ser Ile Leu Ser Glu Ser His Ser Val Ile Val
                420                 425                 430

Met Ser Ser Val Glu Asn Ser Arg His Ser Ser Pro Thr Gly Gly Pro
            435                 440                 445

Arg Gly Arg Leu Asn Gly Thr Gly Gly Pro Arg Glu Cys Asn Ser Phe
        450                 455                 460

Leu Arg His Ala Arg Glu Thr Pro Asp Ser Tyr Arg Asp Ser Pro His
465                 470                 475                 480

Ser Glu Arg Tyr Val Ser Ala Met Thr Thr Pro Ala Arg Met Ser Pro
                    485                 490                 495

Val Asp Phe His Thr Pro Ser Ser Pro Lys Ser Pro Pro Ser Glu Met
                500                 505                 510

Ser Pro Pro Val Ser Ser Met Thr Val Ser Met Pro Ser Met Ala Val
            515                 520                 525

Ser Pro Phe Met Glu Glu Glu Arg Pro Leu Leu Leu Val Thr Pro Pro
        530                 535                 540

Arg Leu Arg Glu Lys Lys Phe Asp His His Pro Gln Gln Phe Ser Ser
545                 550                 555                 560

Phe His His Asn Pro Ala His Asp Ser Asn Ser Leu Pro Ala Ser Pro
                    565                 570                 575

Leu Arg Ile Val Glu Asp Glu Glu Tyr Glu Thr Thr Gln Glu Tyr Glu
                580                 585                 590

Pro Ala Gln Glu Pro Val Lys Lys Leu Ala Asn Ser Arg Arg Ala Lys
            595                 600                 605

Arg Thr Lys Pro Asn Gly His Ile Ala Asn Arg Leu Glu Val Asp Ser
        610                 615                 620

Asn Thr Ser Ser Gln Ser Ser Asn Ser Glu Ser Glu Thr Glu Asp Glu
625                 630                 635                 640

Arg Val Gly Glu Asp Thr Pro Phe Leu Gly Ile Gln Asn Pro Leu Ala
                    645                 650                 655

Ala Ser Leu Glu Ala Thr Pro Ala Phe Arg Leu Ala Asp Ser Arg Thr
                660                 665                 670

Asn Pro Ala Gly Arg Phe Ser Thr Gln Glu Glu Ile Gln Ala Arg Leu
            675                 680                 685

Ser Ser Val Ile Ala Asn Gln Asp Pro Ile Ala Val
        690                 695                 700

<210> SEQ ID NO 11
<211> LENGTH: 55
<212> TYPE: PRT
<213> ORGANISM: Artificial
<220> FEATURE:
<223> OTHER INFORMATION: Synthetic

<400> SEQUENCE: 11

Gly Thr Ser His Leu Val Lys Cys Pro Leu Ser His Glu Ala Tyr Cys
1               5                   10                  15

Val Asn Gly Gly Glu Cys Phe Met Val Lys Asp Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Met Ala Ser Phe
    50                  55
```

-continued

```
                50                  55

<210> SEQ ID NO 12
<211> LENGTH: 53
<212> TYPE: PRT
<213> ORGANISM: Artificial
<220> FEATURE:
<223> OTHER INFORMATION: Synthetic

<400> SEQUENCE: 12

Asn Thr Glu Asn Asp Cys Pro Leu Ser His Glu Ala Tyr Cys Leu His
1               5                   10                  15

Asp Gly Val Cys Arg Phe Leu Val Gln Glu Asp Lys Pro Ala Cys Val
            20                  25                  30

Cys Val Val Gly Tyr Val Gly Glu Arg Cys Gln Phe Arg Asp Leu Arg
        35                  40                  45

Trp Trp Asp Ala Arg
    50

<210> SEQ ID NO 13
<211> LENGTH: 3
<212> TYPE: PRT
<213> ORGANISM: Artificial
<220> FEATURE:
<223> OTHER INFORMATION: Synthetic

<400> SEQUENCE: 13

Ser Ser Gly
1

<210> SEQ ID NO 14
<211> LENGTH: 4
<212> TYPE: PRT
<213> ORGANISM: Artificial
<220> FEATURE:
<223> OTHER INFORMATION: Synthetic

<400> SEQUENCE: 14

Gly Ser Ser Gly
1

<210> SEQ ID NO 15
<211> LENGTH: 5
<212> TYPE: PRT
<213> ORGANISM: Artificial
<220> FEATURE:
<223> OTHER INFORMATION: Synthetic

<400> SEQUENCE: 15

Ser Ser Gly Gly Gly
1               5

<210> SEQ ID NO 16
<211> LENGTH: 3
<212> TYPE: PRT
<213> ORGANISM: Artificial
<220> FEATURE:
<223> OTHER INFORMATION: Synthetic

<400> SEQUENCE: 16

Ser Gly Gly
1

<210> SEQ ID NO 17
<211> LENGTH: 5
```

```
<212> TYPE: PRT
<213> ORGANISM: Artificial
<220> FEATURE:
<223> OTHER INFORMATION: Synthetic

<400> SEQUENCE: 17

Gly Gly Ser Gly Gly
1               5

<210> SEQ ID NO 18
<211> LENGTH: 5
<212> TYPE: PRT
<213> ORGANISM: Artificial
<220> FEATURE:
<223> OTHER INFORMATION: Synthetic

<400> SEQUENCE: 18

Gly Gly Gly Gly Ser
1               5

<210> SEQ ID NO 19
<211> LENGTH: 8
<212> TYPE: PRT
<213> ORGANISM: Artificial
<220> FEATURE:
<223> OTHER INFORMATION: Synthetic

<400> SEQUENCE: 19

Ser Ser Gly Gly Gly Ser Gly Gly
1               5

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Ser Ser Gly Gly Gly Gly Ser Gly Gly Gly
1               5                   10

<210> SEQ ID NO 21
<211> LENGTH: 7
<212> TYPE: PRT
<213> ORGANISM: Artificial
<220> FEATURE:
<223> OTHER INFORMATION: Synthetic

<400> SEQUENCE: 21

Thr Ser Gly Gly Gly Ser Gly
1               5

<210> SEQ ID NO 22
<211> LENGTH: 9
<212> TYPE: PRT
<213> ORGANISM: Artificial
<220> FEATURE:
<223> OTHER INFORMATION: Synthetic

<400> SEQUENCE: 22

Thr Ser Gly Gly Gly Gly Ser Gly Gly
1               5

<210> SEQ ID NO 23
<211> LENGTH: 11
<212> TYPE: PRT
```

```
<213> ORGANISM: Artificial
<220> FEATURE:
<223> OTHER INFORMATION: Synthetic

<400> SEQUENCE: 23

Ser Ser Gly Gly Gly Ser Gly Gly Ser Ser Gly
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic

<400> SEQUENCE: 24

Gly Gly Ser Gly Gly Thr Ser Gly Gly Gly Ser Gly
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

Ser Gly Gly Thr Ser Gly Gly Gly Gly Ser Gly Gly
1               5                   10

<210> SEQ ID NO 26
<211> LENGTH: 14
<212> TYPE: PRT
<213> ORGANISM: Artificial
<220> FEATURE:
<223> OTHER INFORMATION: Synthetic

<400> SEQUENCE: 26

Gly Gly Ser Gly Gly Thr Ser Gly Gly Gly Ser Gly Gly
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic

<400> SEQUENCE: 27

Ser Ser Gly Gly Gly Gly Ser Gly Gly Gly Ser Ser Gly
1               5                   10

<210> SEQ ID NO 28
<211> LENGTH: 13
<212> TYPE: PRT
<213> ORGANISM: Artificial
<220> FEATURE:
<223> OTHER INFORMATION: Synthetic

<400> SEQUENCE: 28

Ser Ser Gly Gly Gly Ser Gly Gly Ser Ser Gly Gly Gly
1               5                   10

<210> SEQ ID NO 29
<211> LENGTH: 15
<212> TYPE: PRT
<213> ORGANISM: Artificial
```

<220> FEATURE:
<223> OTHER INFORMATION: Synthetic

<400> SEQUENCE: 29

Ser Ser Gly Gly Gly Ser Gly Gly Ser Ser Gly Gly Gly
1               5                   10                  15

<210> SEQ ID NO 30
<211> LENGTH: 14
<212> TYPE: PRT
<213> ORGANISM: Artificial
<220> FEATURE:
<223> OTHER INFORMATION: Synthetic

<400> SEQUENCE: 30

Gly Gly Ser Gly Gly Thr Ser Gly Gly Gly Gly Ser Gly
1               5                   10

<210> SEQ ID NO 31
<211> LENGTH: 227
<212> TYPE: PRT
<213> ORGANISM: Artificial
<220> FEATURE:
<223> OTHER INFORMATION: Synthetic

<400> SEQUENCE: 31

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Ile Gly Glu Arg Cys Gln Tyr Arg Asp Leu Lys
            35                  40                  45

Trp Trp Glu Leu Arg Gly Ser Ser Gly Asn Ser Asp Ser Glu Cys Pro
    50                  55                  60

Leu Ser His Asp Gly Tyr Cys Leu His Asp Gly Val Cys Met Tyr Ile
65                  70                  75                  80

Glu Ala Leu Asp Lys Tyr Ala Cys Asn Cys Val Val Gly Tyr Ile Gly
                85                  90                  95

Glu Arg Cys Gln Tyr Arg Asp Leu Lys Trp Trp Glu Leu Arg Gly Gly
            100                 105                 110

Ser Gly Gly Thr Ser Gly Gly Gly Gly Ser Gly Thr Pro Gln Asn
            115                 120                 125

Ile Thr Asp Leu Cys Ala Glu Tyr His Asn Thr Gln Ile His Thr Leu
130                 135                 140

Asn Asp Lys Ile Phe Ser Tyr Thr Glu Ser Leu Ala Asp Lys Arg Glu
145                 150                 155                 160

Met Ala Ile Ile Thr Phe Lys Asn Gly Ala Thr Phe Gln Val Glu Val
                165                 170                 175

Pro Gly Ser Gln His Ile Asp Ser Gln Lys Lys Ala Ile Glu Arg Met
            180                 185                 190

Lys Asp Thr Leu Arg Ile Ala Tyr Leu Thr Glu Ala Lys Val Glu Lys
            195                 200                 205

Leu Cys Val Trp Asn Asn Lys Thr Pro His Ala Ile Ala Ala Ile Ser
    210                 215                 220

Met Ala Asn
225

<210> SEQ ID NO 32
<211> LENGTH: 55

```
<212> TYPE: PRT
<213> ORGANISM: Artificial
<220> FEATURE:
<223> OTHER INFORMATION: Synthetic

<400> SEQUENCE: 32

Gly Thr Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Met Ala Ser Phe
    50                  55

<210> SEQ ID NO 33
<211> LENGTH: 53
<212> TYPE: PRT
<213> ORGANISM: Artificial
<220> FEATURE:
<223> OTHER INFORMATION: Synthetic

<400> SEQUENCE: 33

Asn Thr Glu Asn Asp Cys Pro Leu Ser His Glu Ala Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Val Gly Glu Arg Cys Gln Phe Arg Asp Leu Arg
        35                  40                  45

Trp Trp Asp Ala Arg
    50

<210> SEQ ID NO 34
<211> LENGTH: 11
<212> TYPE: PRT
<213> ORGANISM: Artificial
<220> FEATURE:
<223> OTHER INFORMATION: Synthetic

<400> SEQUENCE: 34

Phe Leu Val Gln Glu Asp Lys Pro Ala Cys Val
1               5                   10

<210> SEQ ID NO 35
<211> LENGTH: 53
<212> TYPE: PRT
<213> ORGANISM: Artificial
<220> FEATURE:
<223> OTHER INFORMATION: Synthetic

<400> SEQUENCE: 35

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

SYNTHETIC PROTEINS AND THERAPEUTIC USES THEREOF

CROSS REFERENCE TO RELATED APPLICATIONS

This patent application is a national stage application, filed under 35 U.S.C. § 371 of International Application No. PCT/IB2018/000898, filed Jul. 18, 2018, which claims the benefit of priority of U.S. Provisional Patent Application No. 62/533,901, filed Jul. 18, 2017, the entire contents of which are hereby incorporated by reference.

FIELD OF THE DISCLOSURE

The disclosure relates to compositions and methods for treating disease. More particularly, the disclosure relates to synthetic proteins and their use for treating cancer.

SEQUENCE LISTING

The instant application contains a modified sequence listing which has been filed electronically in ASCII format and is hereby incorporated by reference in its entirety. Said ASCII copy, created on Feb. 7, 2020, is named 48199_103_SequenceListing_Text.txt and is 71,690 bytes in size.

BACKGROUND OF THE DISCLOSURE

According to the World Health Organization, neoplasia (e.g., cancer) is one of the leading causes of death worldwide and was responsible for 8.8 million deaths in 2015. The frequency of cancer in the global human population is significant: accounting for nearly 1 in 6 deaths. In 2015, the most common cancer deaths occurred from the following types of cancer: lung cancer (about 1.7 million deaths), liver cancer (about 800,000 deaths), colorectal cancer (about 800,000 deaths), stomach cancer (about 800,000 deaths), and breast cancer (about 600,000 deaths).

Cancer is typically treated by any of a variety of methods such as, for example, surgery, chemotherapy, radiation therapy, cancer immunotherapy, and the like. Unfortunately, many of these methods have toxic/undesirable side effects. For example, standard cancer chemotherapies were developed based on their ability to kill rapidly dividing cells, and many have toxic properties that cause undesirable side effects such as, for example, immunosuppression, nausea, hair loss, and the like. A central goal of cancer research over the past two decades has been to identify new therapies with greater efficacy and fewer side effects.

One such therapy is encompassed by cancer immunology, which is the study of interactions between an immune system and cancer cells such as tumors or malignancies. The initiation of an immune response, such as recognition of cancer-specific antigens that are expressed by human tumors and not expressed in normal tissues, is of particular interest. Generally, methods to control the division and proliferation of the malignant cells have focused on isolating these antigens and presenting them so that they are recognized by the immune system as non-self antigens to induce a specific immune response (e.g., cancer vaccines). Disadvantageously, such cancer vaccines exhibit a number of significant limitations, which arise primarily from the method of manufacture and the potential lack of uniformity, activity, and homology of the protein product. For example, cancer vaccines generally comprise a mixture of a recombinant carrier protein and polypeptides of human origin that are chemically conjugated using glutaraldehyde. Unfortunately, this reactive reagent has the undesirable tendency to form covalent cross-linking bonds between varieties of chemical groups, and generally leads to a highly heterogeneous product. Thus, the resulting vaccines may comprise not only carrier protein molecules with varying numbers of the target human polypeptide attached (e.g., 0, 1, 2, 3, etc.), but the human polypeptides can each be attached to the carrier via different atoms and therefore be present in different positions and in different orientations. Furthermore, both the target polypeptide and carrier protein molecules may be conjugated to themselves, resulting in various homo-multimers that may have no clinical efficacy and may not contribute to an anti-cancer patient immune response. Accordingly, there is an urgent need for new cancer vaccines that overcome these significant existing limitations in the field of cancer immunotherapy.

SUMMARY OF THE DISCLOSURE

The present disclosure is directed towards synthetic proteins/molecules and their respective methods of manufacturing; the characterization of the synthetic proteins/molecules and therapeutic methods of using the synthetic proteins/molecules to treat chronic diseases, such as, for example, lung, breast, bladder, prostate, ovarian, vulva, colonic, colorectal, intestinal, pulmonary, brain, esophageal, other cancers, and other diseases.

The present disclosure provides synthetic proteins that may be used as therapeutic modalities to treat diseases such as, for example, cancer. In an illustrative embodiment, the present disclosure provides a synthetic protein/molecule including one or more protein domains from a synthetic growth factor, one or more linker regions, and one or more immunogenic domains.

In one aspect, the present disclosure provides a synthetic protein that includes a synthetic growth factor sequence; at least one linker, and a polypeptide sequence.

In an illustrative embodiment, the polypeptide sequence includes an immunogenic polypeptide sequence. In an illustrative embodiment, the polypeptide sequence includes a cholera toxin (CT-B) protein.

In an illustrative embodiment, the at least one linker includes a first linker that separates the synthetic growth factor from the polypeptide sequence. In an illustrative embodiment, the first linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29). In an illustrative embodiment, the first linker is GGSGGTSGGGGSG (SEQ ID NO: 30).

In an illustrative embodiment, the synthetic growth factor sequence includes a synthetic epidermal growth factor (sEGF) sequence. In an illustrative embodiment, the synthetic growth factor sequence includes at least one synthetic targeted signaling pathway (sTSP) domain of a human epidermal growth factor (hEGF) TSP (hTSP) domain in which the at least one sTSP differs from the hTSP by 6, 7, 8, 9, 10, or more amino acids. In an illustrative embodiment, the synthetic growth factor sequence includes a first TSP domain and a second TSP domain.

In an illustrative embodiment, the at least one linker includes a second linker that separates the first TSP domain and the second TSP domain. In an illustrative embodiment, the second linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29). In an illustrative embodiment, the second linker is GSSG (SEQ ID NO: 14). In an illustrative embodiment, the synthetic protein has the amino acid sequence of SEQ ID NO:2. In an illustrative embodiment, the synthetic protein is encoded by the nucleic acid sequence of SEQ ID NO:1.

In an illustrative embodiment, a portion of the synthetic growth factor includes a full length or neutralizing domain of at least two different growth factors present in said synthetic protein.

In one aspect, the present disclosure provides an immunogenic composition, comprising a synthetic protein that includes a synthetic growth factor sequence, at least one linker, and a polypeptide sequence.

In an illustrative embodiment, the polypeptide sequence includes an immunogenic polypeptide sequence. In an illustrative embodiment, the polypeptide sequence includes a cholera toxin B (CT-B) protein.

In an illustrative embodiment, the at least one linker includes a first linker that separates the synthetic growth factor from the polypeptide sequence. In an illustrative embodiment, the first linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29). In an illustrative embodiment, the first linker is GGSGGTSGGGGSG (SEQ ID NO: 30).

In an illustrative embodiment, the synthetic growth factor sequence includes a synthetic epidermal growth factor (sEGF) sequence. In an illustrative embodiment, the synthetic growth factor sequence includes at least one synthetic targeted signaling pathway (sTSP) domain of a human epidermal growth factor (hEGF) TSP (hTSP) domain in which the at least one sTSP differs from the hTSP by 6, 7, 8, 9, 10, or more amino acids. In an illustrative embodiment, the synthetic growth factor sequence includes a first TSP domain and a second TSP domain.

In an illustrative embodiment, the at least one linker includes a second linker that separates the first TSP domain and the second TSP domain. In an illustrative embodiment, the second linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29). In an illustrative embodiment, the second linker is GSSG (SEQ ID NO: 14). In an illustrative embodiment, the synthetic protein has the amino acid sequence of SEQ ID NO:2.

In an illustrative embodiment, the synthetic protein is encoded by the nucleic acid sequence of SEQ ID NO: 1.

In an illustrative embodiment, a portion of the synthetic growth factor includes a full length or neutralizing domain of at least two different growth factors present in said synthetic protein. In an illustrative embodiment, the composition further comprises an adjuvant.

In one aspect, the preset disclosure provides a method of treating a patient that includes the steps of administering to the patient an immunogenic composition that includes a synthetic protein having a synthetic growth factor sequence, at least one linker, and a polypeptide sequence in the same day or in alternate days or times during a vaccination period.

Definitions

By "BVN22E nucleic acid molecule" is meant a polynucleotide encoding a BVN22E polypeptide. An exemplary BVN22E nucleic acid molecule is reproduced below (SEQ ID NO:1):

```
>BVN22E
AATACCGAAAACGATTGCCCTCTGTCTCATGAAGCGTATTGTCTGCACG

ACGGCGTGTGTATGTACATTGAAGCCCTGGACAAATATGCATGTAACTG

TGTCGTGGGCTACGTGGGGAGCGATGTCAGTTTCGAGACCTGCGTTGG

TGGGATGCGCGCGGCTCGAGCGGTAATACCGAAAACGATTGCCCTCTGT

CTCATGAAGCGTATTGTCTGCACGACGGCGTGTGTATGTACATTGAAGC

CCTGGACAAATATGCATGTAACTGTGTCGTGGGCTACGTGGGGGAGCGA

TGTCAGTTTCGAGACCTGCGTTGGTGGGATGCGCGCGGCGGGTCTGGAG

GTACTAGTGGCGGCGGTGGAGGGTCGGGTACCCCGCAGAACATCACCGA

CCTGTGCGCCGAGTACCACAACACCCAGATCCACACCCTGAACGACAAG

ATCTTCTCGTACACCGAGAGCCTGGCCGATAAGCGTGAAATGGCCATCA

TCACCTTCAAGAACGGTGCGACCTTCCAGGTGGAGGTCCCGGGTAGCCA

GCACATCGATTCACAGAAGAAGGCCATCGAGCGTATGAAGGACACCCTG

CGTATCGCCTACCTGACCGAAGCCAAGGTGGAAAAGCTGTGCGTCTGGA

ACAACAAGACGCCGCACGCCATCGCCGCCATCAGCATGGCCAAT
```

By "BVN22E polypeptide" is meant a polypeptide or fragment thereof having at least about 85%, 90%, 91%, 92%, 93%, 94%, 95%, 96%, 97%, 98%, or 99% amino acid identity (excluding the following amino acid changes: T2S, E3D, N4S, D5E, E11D, A12G, V38I, F44Y, R48K, D51E, and A52L) to the amino acid sequence below (SEQ ID NO:2):

```
>BVN22E
NTENDCPLSHEAYCLHDGVCMYIEALDKYACNCVVGYVGERCQFRDLRW
WDARGSSGNTENDCPLSHEAYCLHDGVCMYIEALDKYACNCVVIGYVGE
RCQFRDLRWWDARGGSGGTSGGGGGSGTPQNITDLCAEYHNTQIHTLND
KIFSYTESLADKREMAIITFKNGATFQVEVPGSQHIDSQKKAIERMKDT
LRIAYLTEAKVEKLCVWNNKTPHAIAAISMAN
```

By "Epidermal Growth Factor Receptor (EGFR) nucleic acid molecule" is meant a polynucleotide encoding an EGFR polypeptide. An exemplary EGFR nucleic acid molecule is provided at NCBI Accession No. NM_005228.4, and reproduced below (SEQ ID NO:3):

```
>NM_005228.4
gtccgggcagccccggcgcagcgcggccgcagcagcctccgccccccgc
acggtgtgagcgcccgacgcggccgaggcggccggagtcccgagctagcc
ccggcggccgccgcgcccagaccggacgacaggccacctcgtcggcgtc
cgcccgagtccccgcctcgccgccaacgccacaaccaccgcgcacggccc
cctgactccgtccagtattgatcgggagagccggagcgagctcttcgggg
agcagcgatgcgaccctccgggacggccggggcagcgctcctggcgctgc
tggctgcgctctgcccggcgagtcgggctctggaggaaaagaaagtttgc
caaggcacgagtaacaagctcacgcagttgggcacttttgaagatcattt
tctcagcctccagaggatgttcaataactgtgaggtggtccttgggaatt
tggaaattacctatgtgcagaggaattatgatctttccttcttaaagacc
atccaggaggtggctggttatgtcctcattgccctcaacacagtggagcg
aattcctttggaaaacctgcagatcatcagaggaaatatgtactacgaaa
attcctatgccttagcagtcttatctaactatgatgcaaataaaaccgga
ctgaaggagctgcccatgagaaatttacaggaaatcctgcatggcgccgt
gcggttcagcaacaaccctgccctgtgcaacgtggagagcatccagtggc
gggacatagtcagcagtgactttctcagcaacatgtcgatggacttccag
aaccacctgggcagctgccaaaagtgtgatccaagctgtcccaatgggag
ctgctggggtgcaggagaggagaactgccagaaactgaccaaaatcatct
gtgcccagcagtgctccggggcgctgccgtggcaagtccccagtgactgc
tgccacaaccagtgtgctgcaggctgcacaggccccgggagagcgactg
cctggtctgccgcaaattccgagacgaagccacgtgcaaggacacctgcc
ccccactcatgctctacaacccaccacgtaccagatggatgtgaacccc
gagggcaaatacagctttggtgccacctgcgtgaagaagtgtccccgtaa
ttatgtggtgacagatcacggctcgtgcgtccgagcctgtggggccgaca
gctatgagatggaggaagacgcgtccgcaagtgtaagaagtgcgaaggg
ccttgccgcaaagtgtgtaacggaataggtattggtgaatttaaagactc
actctccataaatgctacgaatattaaacacttcaaaaactgcacctcca
tcagtggcgatctccacatcctgccggtggcatttaggggtgactccttc
acacatactcctcctggatccacaggaactggatattctgaaaaccgt
aaaggaaatcacaggggttttgctgattcaggcttggcctgaaaacagga
cggacctccatgcctttgagaacctagaaatcatacgcggcaggaccaag
caacatggtcagttttctcttgcagtcgtcagcctgaacataacatcctt
gggattacgctccctcaaggagataagtgatggagatgtgataatttcag
gaaacaaaaatttgtgctatgcaaatacaataaactggaaaaaactgttt
gggacctccggtcagaaaaccaaaattataagcaacagaggtgaaaacag
ctgcaaggccacaggccaggtctgccatgccttgtgctcccccgagggct
gctggggcccggagcccagggactgcgtctcttgccggaatgtcagccga
ggcaggaatgcgtggacaagtgcaaccttctggagggtgagccaaggga
gtttgtggagaactctgagtgcatacagtgccacccagagtgcctgcctc
aggccatgaacatcacctgcacaggacggggaccagacaactgtatccag
tgtgcccactacattgacggcccccactgcgtcaagacctgcccggcagg
agtcatgggagaaaacaaccacccctggtctggaagtacgcagacgccggcc
atgtgtgccacctgtgccatccaaactgcacctacggatgcactgggcca
ggtcttgaaggctgtccaacgaatgggcctaagatcccgtccatcgccac
tgggatggtgggggccctcctcttgctgctggtggtggccctggggatcg
gcctcttcatgcgaaggcgccacatcgttcggaagcgcacgctgcggagg
ctgctgcaggagagggagcttgtggagcctcttacacccagtggagaagc
tcccaaccaagctctcttgaggatcttgaaggaaactgaattcaaaaaga
tcaaagtgctgggctccggtgcgttcggcacggtgtataagggactctgg
atcccagaaggtgagaaagttaaaattcccgtcgctatcaaggaattaag
agaagcaacatctccgaaagccaacaaggaaatcctcgatgaagcctacg
tgatggccagcgtggacaaccccacgtgtgccgcctgctgggcatctgc
ctcacctccaccgtgcagctcatcacgcagctcatgcccttcggctgcct
cctggactatgtccgggaacacaaagacaatattggctcccagtacctgc
tcaactggtgtgtgcagatcgcaaagggcatgaactacttggaggaccgt
cgcttggtgcaccgcgacctggcagccaggaacgtactggtgaaaacacc
gcagcatgtcaagatcacagattttgggctggccaaactgctgggtgcgg
aagagaaagaataccatgcagaaggaggcaaagtgcctatcaagtggatg
gcattggaatcaattttacacagaatctatacccaccagagtgatgtctg
gagctacggggtgactgtttgggagttgatgacctttggatccaagccat
atgacggaatcctgccagcgagatctcctccatcctggagaaaggagaa
cgcctccctcagccacccatatgtaccatcgatgtctacatgatcatggt
caagtgctggatgatagacgcagatagtcgcccaaagttccgtgagttga
tcatcgaattctccaaaatggcccgagaccccagcgctaccttgtcatt
caggggatgaaagaatgcatttgccaagtcctacagactccaacttcta
ccgtgccctgatgatgaagaagacatggacgacgtggtggatgccgacg
agtacctcatcccacagcagggcttcttcagcagccctccacgtcacgg
actcccctcctgagctctctgagtgcaaccagcaacaattccaccgtggc
ttgcattgatagaaatgggctgcaaagctgtcccatcaaggaagacagct
tcttgcagcgatacagctcagaccccacaggcgccttgactgaggacagc
atagacgacaccttcctcccagtgcctgaatacataaaccagtccgttcc
```

-continued

```
caaaaggcccgctggctctgtgcagaatcctgtctatcacaatcagcctc tgaacccgcgcccagcagagacccacactaccaggaccccacagcact gcagtgggcaaccccgagtatctcaacactgtccagcccacctgtgtcaa cagcacattcgacagccctgcccactgggcccagaaaggcagccaccaa ttagcctggacaaccctgactaccagcaggacttctttcccaaggaagcc aagccaaatggcatctttaagggctccacagctgaaaatgcagaatacct aagggtcgcgccacaaagcagtgaatttattggagcatgaccacggagga tagtatgagccctaaaaatccagactcttttcgatacccaggaccaagcca cagcaggtcctccatcccaacagccatgcccgcattagctcttagaccca cagactggttttgcaacgtttacaccgactagccaggaagtacttccacc tcgggcacattttgggaagttgcattcctttgtcttcaaactgtgaagca tttacagaaacgcatccagcaagaatattgtcccttgagcagaaattta tctttcaaagaggtatatttgaaaaaaaaaaaagtatatgtgaggatt ttattgattggggatcttggagttttttcattgtcgctattgatttttact tcaatgggctcttccaacaaggaagaagcttgctggtagcacttgctacc ctgagttcatccaggcccaactgtgagcaaggagcacaagccacaagtct tccagaggatgcttgattccagtggttctgcttcaaggcttccactgcaa aacactaaagatccaagaaggccttcatggcccccagcaggccggatcggt actgtatcaagtcatggcaggtacagtaggataagccactctgtcccttc ctgggcaaagaagaaacggaggggatggaattcttccttagacttacttt tgtaaaaatgtcccacggtacttactccccactgatggaccagtggttt ccagtcatgagcgttagactgacttgtttgtcttccattccattgttttg aaactcagtatgctgccctgtcttgctgtcatgaaatcagcaagagagg atgacacatcaaataataactcggattccagcccacattggattcatcag catttggaccaatagccacagctgagaatgtggaatacctaaggatagc accgcttttgttctcgcaaaaacgtatctcctaatttgaggctcagatga aatgcatcaggtcctttggggcatagatcagaagactacaaaaatgaagc tgctctgaaatctcctttagccatcaccccaaccccccaaaattagtttg tgttacttatggaagatagttttctccttttacttcacttcaaaagcttt ttactcaaagagtatatgttccctccaggtcagctgcccccaaaccccct ccttacgctttgtcacacaaaagtgtctctgccttgagtcatctattca agcacttacagctctggccacaacagggcattttacaggtgcgaatgaca gtagcattatgagtagtgtggaattcaggtagtaaatatgaaactaggt ttgaaattgataatgctttcacaacatttgcagatgttttagaaggaaaa aagttccttcctaaaataatttctctacaattggaagattggaagattca gctagttaggagcccacctttttttcctaatctgtgtgtgccctgtaacct gactggttaacagcagtcctttgtaaacagtgttttaaactctcctagtc aatatccaccccatccaatttatcaaggaagaaatggttcagaaaatatt ttcagcctacagttatgttcagtcacacacacatacaaaatgttccttttt gcttttaaagtaattttttgactcccagatcagtcagagccctacagcat tgttaagaaagtatttgattttttgtctcaatgaaaataaaactatattca tttccactctattatgctctcaaatacccctaagcatctatactagcctg gtatgggtatgaaagatacaaagataaataaaacatagtccctgattcta agaaattcacaatttagcaaaggaaatggactcatagatgctaaccttaa aacaacgtgacaaatgccagacaggacccatcagccaggcactgtgagag cacagagcagggaggttgggtcctgcctgaggagacctggaagggaggcc tcacaggaggatgaccaggtctcagtcagcgggaggtggaaagtgcagg tgcatcaggggcaccctgaccgaggaaacagctgccagaggcctccactg ctaaagtccacataaggctgaggtcagtcaccctaaacaacctgctccct ctaagccagggatgagcttggagcatcccacaagttccctaaaagttgc agccccaggggattttgagctatcatctctgcacatgcttagtgagaa gactacacaacatttctaagaatctgagatttatattgtcagttaacca cttttcattattcattcacctcaggacatgcagaaatattcagtcagaac tgggaaacagaaggacctacattctgctgtcacttatgtgtcaagaagca gatgatcgatgaggcaggtcagttgtaagtgagtcacattgtagcattaa attctagtattttgtagtttgaaacagtaacttaataaaagagcaaaag ctaaaaaaaaaaaaaaaaa
```

By "Epidermal Growth Factor Receptor (EGFR) polypeptide" is meant a polypeptide or fragment thereof having at least about 85% amino acid identity to NCBI Accession No. NP_005219.2 and having Epidermal Growth Factor (EGF) binding activity, as reproduced below (SEQ ID NO:4):

```
>NP_005219.2
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLROLKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
```

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA

By "Epidermal Growth Factor (EGF) nucleic acid molecule" is meant a polynucleotide encoding an EGF polypeptide. An exemplary EGF nucleic acid molecule is provided at NCBI Accession No. NM_001963.5, and reproduced below (SEQ ID NO:5):

```
>NM_001963.5
aaaaagagaaactgttgggagaggaatcgtatctccatatttcttctttc
agccccaatccaagggttgtagctggaacttttccatcagttcttcctttc
tttttcctctctaagcctttgccttgctctgtcacagtgaagtcagccag
agcagggctgttaaactctgtgaaatttgtcataagggtgtcaggtattt
cttactggcttccaaagaaacatagataaagaaatctttcctgtggcttc
ccttggcaggctgcattcagaaggtctctcagttgaagaaagagcttgga
ggacaacagcacaacaggagagtaaaagatgcccagggctgaggcctcc
gctcaggcagccgcatctgggtcaatcatactccaccttgcccgggccat
gctccagcaaaatcaagctgttttcttttgaaagttcaaactcatcaaga
ttatgctgctcactcttatcattctgttgccagtagtttcaaaatttagt
tttgttagtctctcagcaccgcagcactgtgagctgtcctgaaggtactct
cgcaggaaatgggaattctacttgtgtgggtcctgcacccttcttaattt
tctcccatggaaatagtatctttaggattgacacagaaggaaccaattat
gagcaattggtggtggatgctggtgtctcagtgatcatggattttcatta
taatgagaaagaatctattgggtggatttagaaagacaacttttgcaaa
gagttttctgaatgggtcaaggcaagagagagtatgtaatatagagaaa
aatgtttctggaatggcaataaattggataaatgaagaagttatttggtc
aaatcaacaggaaggaatcattacagtaacagatatgaaaggaaataatt
cccacattcttttaagtgctttaaaatatcctgcaaatgtagcagttgat
ccagtagaaaggtttatattttggtcttcagaggtggctggaagcctttta
tagagcagatctcgatggtgtgggagtgaaggctctgttggagacatcag
agaaaataacagctgtgtcattggatgtgcttgataagcggctgttttgg
attcagtacaacagagaaggaagcaattctcttatttgctcctgtgatta
tgatggaggttctgtccacattagtaaacatccaacacagcataatttgt
ttgcaatgtcccttttggtgaccgtatcttctattcaacatggaaatg
aagacaatttggatagccaacaaacacactggaaggacatggttagaat
taacctccattcatcatttgtaccacttggtgaactgaaagtagtgcatc
cacttgcacaacccaaggcagaagatgacacttgggagcctgagcagaaa
ctttgcaaattgaggaaaggaaactgcagcagcactgtgtgtgggcaaga
cctccagtcacacttgtgcatgtgtgcagagggatacgccctaagtcgag
accggaagtactgtgaagatgttaatgaatgtgcttttggaatcatggc
tgtactcttgggtgtaaaaacaccctggatcctattactgcacgtgccc
tgtaggatttgttctgcttcctgatgggaaacgatgtcatcaacttgttt
cctgtccacgcaatgtgtctgaatgcagccatgactgtgttctgacatca
gaaggtcccttatgtttctgtcctgaaggctcagtgcttgagagagatgg
gaaaacatgtagcggttgttcctcacccgataatggtggatgtagccagc
tctgcgttcctcttagcccagtatcctgggaatgtgattgcttttcctggg
tatgacctacaactggatgaaaaaagctgtgcagcttcaggaccacaacc
attttttgctgtttgccaattctcaagatattcgacacatgcattttgatg
gaacagactatggaactctgctcagccagcagatgggaatggtttatgcc
ctagatcatgaccctgtgaaaataagatatactttgcccatacagccct
gaagtggatagagagagctaatatggatggtcccagcgagaaaggctta
ttgaggaaggagtagatgtgccagaaggtcttgctgtggactggattggc
cgtagattctattggacagacagagggaaatctctgattggaaggagtga
tttaaatgggaaacgttccaaaataatcactaaggagaacatctctcaac
cacgaggaattgctgttcatccaatggccaagagattattctggactgat
acagggattaatccacgaattgaaagttcttccctccaaggccttggccg
tctggttatagccagctctgatctaatctggcccagtggaataacgattg
acttcttaactgacaagttgtactggtgcgatgccaagcagtctgtgatt
gaaatggccaatctggatggttcaaaacgccgaagacttacccagaatga
tgtaggtcacccatttgctgtagcagtgtttgaggattatgtgtggttct
cagattgggctatgccatcagtaatgagagtaaacaagaggactggcaaa
gatagagtacgtctccaaggcagcatgctgaagccctcatcactggttgt
ggttcatccattggcaaaaccaggagcagatccctgcttatatcaaaacg
gaggctgtgaacatatttgcaaaagaggcttggaactgcttggtgttcg
tgtcgtgaaggttttatgaaagcctcagatgggaaacgtgtctggctct
ggatggtcatcagctgttggcaggtggtgaagttgatctaaagaaccaag
taacaccattggacatcttgtccaagactagagtgtcagaagataacatt
acagaatctcaacacatgctagtggctgaaatcatggtgtcagatcaaga
tgactgtgctcctgtgggatgcagcatgtatgctcggtgtatttcagagg
gagaggatgccacatgtcagtgtttgaaaggatttgctggggatggaaaa
ctatgttctgatatagatgaatgtgagatgggtgtcccagtgtgcccccc
tgcctcctccaagtgcatcaacaccgaaggtggttatgtctgccggtgct
cagaaggctaccaaggagatgggattcactgtcttgatattgatgagtgc
caactggggagcacagctgtggagagaatgccagctgcacaaatacaga
gggaggctatacctgcatgtgtgctggacgcctgtctgaaccaggactga
tttgccctgactctactccaccccctcacctcagggaagatgaccaccac
tattccgtaagaaatagtgactctgaatgtccctgtcccacgatgggta
ctgcctccatgatggtgtgtgcatgtatattgaagcattggacaagtatg
```

```
catgcaactgtgttgttggctacatcggggagcgatgtcagtaccgagac
ctgaagtggtgggaactgcgccacgctggccacgggcagcagcagaaggt
catcgtggtggctgtctgcgtggtggtgcttgtcatgctgctcctcctga
gcctgtgggggggcccactactacaggactcagaagctgctatcgaaaaac
ccaaagaatccttatgaggagtcgagcagagatgtgaggagtcgcaggcc
tgctgacactgaggatgggatgtcctcttgccctcaaccttggtttgtgg
ttataaaagaacaccaagacctcaagaatgggggtcaaccagtggctggt
gaggatggccaggcagcagatgggtcaatgcaaccaacttcatggaggca
ggagcccagttatgtggaatgggcacagagcaaggctgctggattccag
tatccagtgataagggctcctgtcccaggtaatggagcgaagctttcat
atgccctcctatgggacacagacccttgaaggggggtgtcgagaagcccca
ttctctcctatcagctaacccattatggcaacaaagggccctggacccac
cacaccaaatggagctgactcagtgaaaactggaattaaaaggaaagtca
agaagaatgaactatgtcgatgcacagtatctttctctttcaaaagtagag
caaaactataggttttggttccacaatctctacgactaatcacctactca
atgcctggagacagatacgtagttgtgcttttgtttgctcttttaagcag
tctcactgcagtcttatttccaagtaagagtactgggagaatcactaggt
aacttattagaaacccaaattgggacaacagtgctttgtaaattgtgttg
tcttcagcagtcaatacaaatagattttgttttgttgttcctgcagcc
ccagaagaaattaggggttaaagcagacagtcacactggtttggtcagtt
acaaagtaatttctttgatctggacagaacatttatatcagtttcatgaa
atgattggaatattacaataccgttaagatacagtgtaggcatttaactc
ctcattggcgtggtccatgctgatgattttgcaaaatgagttgtgatgaa
tcaatgaaaaatgtaatttagaaactgattcttcagaattagatggctt
atttttttaaaatatttgaatgaaaacatttttattttaaaatattacaca
ggaggcttcggagtttcttagtcattactgtccttttcccctacagaatt
ttccctcttggtgtgattgcacagaatttgtatgtatttcagttacaag
attgtaagtaaattgcctgatttgttttcattatagacaacgatgaattt
cttctaattatttaaataaaatcaccaaaaacataaacattttattgtat
gcctgattaagtagttaattatagtctaaggcagtactagagttgaacca
aaatgatttgtcaagcttgctgatgtttctgttttcgttttttttttt
ttccggagagaggataggatctcactctgttatccaggctggagtgtgca
atggcacaatcatagctcagtgcagcctcaaactcctgggctcaagcaat
cctcctgcctcagcctcccgagtaactaggaccacaggcacaggccacca
tgcctggctaaggttttatttttattttttgtagacatggggatcacac
aatgttgcccaggctggtcttgaactcctggcctcaagcaaggtcgtgct
ggtaattttgcaaaatgaattgtgattgactttcagcctccaacgtatt
agattataggcattagccatggtgcccagccttgtaacttttaaaaaat
tttttaatctacaactctgtagattaaaatttcacatggtgttctaatta
aatattttcttgcagccaagatattgttactacagataacacaacctga
tatggtaactttaaattttgggggctttgaatcattcagttatgcatta
actagtcccctttgtttatctttcatttctcaacccccttgtactttggtga
taccagacatcagaataaaaagaaattgaagtacctgttttcaaatggat
actttataggaattttggtaaagatttggtgatgggaggatgacttgagg
tttgtggatattagttaattattcagtatgatacctcacccagctaattt
```

By "Epidermal Growth Factor (EGF) polypeptide" is meant a polypeptide or fragment thereof having at least about 85% amino acid identity to NCBI Accession No. NP_001954.2 and corresponding to a pre-pro-protein form of EGF that is processed to produce a 53 amino acid EGF molecule (shown in bold) and having EGFR binding activity, as reproduced below (SEQ ID NO:6):

```
>NP_001954.2
MLLTLIILLPVVSKFSFVSLSAPQHWSCPEGTLAGNGNSTCVGPAPFLIF
SHGNSIFRIDTEGTNYEQLVVDAGVSVIMDFHYNEKRIYWVDLERQLLQR
VFLNGSRQERVCNIEKNVSGMAINWINEEVIWSNQQEGIITVTDMKGNNS
HILLSALKYPANVAVDPVERFIFWSSEVAGSLYRADLDGVGVKALLETSE
KITAVSLDVLDKRLFWIQYNREGSNSLICSCDYDGGSVHISKHPTQHNLF
AMSLFGDRIFYSTWKMKTIWIANKHTGKDMVRINLHSSFVPLGELKVVHP
LAQPKAEDDTWEPEQKLCKLRKGNCSSTVCGQDLQSHLCMCAEGYALSRD
RKYCEDVNECAFWNHGCTLGCKNTPGSYYCTCPVGFVLLPDGKRCHQLVS
CPRNVSECSHDCVLTSEGPLCFCPEGSVLERDGKTCSGCSSPDNGGCSQL
CVPLSPVSWECDCFPGYDLQLDEKSCAASGPQPFLLFANSQDIRHMHFDG
TDYGTLLSQQMGMVYALDHDPVENKIYFAHTALKWIERANMDGSQRERLI
EEGVDVPEGLAVDWIGRRFYWTDRGKSLIGRSDLNGKRSKIITKENISQP
RGIAVHPMAKRLFWTDTGINPRIESSSLQGLGRLVIASSDLIWPSGITID
FLTDKLYWCDAKQSVIEMANLDGSKRRRLTQNDVGHPFAVAVFEDYVWFS
DWAMPSVMRVNKRTGKDRVRLQGSMLKPSSLVVVHPLAKPGADPCLYQNG
GCEHICKKRLGTAWCSCREGFMKASDGKTCLALDGHQLLAGGEVDLKNQV
TPLDILSKTRVSEDNITESQHMLVAEIMVSDQDDCAPVGCSMYARCISEG
EDATCQCLKGFAGDGKLCSDIDECEMGVPVCPPASSKCINTEGGYVCRCS
EGYQGDGIHCLDIDECQLGEHSCGENASCTNTEGGYTCMCAGRLSEPGLI
CPDSTPPPHLREDDHHYSVRNSDSECPLSHDGYCLHDGVCMYIEALDKYA
CNCVVGYIGERCQYRDLKWWELRHAGHGQQQKVIVVAVCVVVLVMLLLS
LWGAHYYRTQKLLSKNPKNPYEESSRDVRSRRPADTEDGMSSCPQPWFVV
IKEHQDLKNGGQPVAGEDGQAADGSMQPTSWRQEPQLCGMGTEQGCWIPV
SSDKGSCPQVMERSFHMPSYGTQTLEGGVEKPHSLLSANPLWQQRALDPP
HQMELTQ
```

By "Neuregulin 1 (NRG1) nucleic acid molecule" is meant a polynucleotide encoding an NRG1 polypeptide. An exemplary NRG1 nucleic acid molecule is provided at NCBI Accession No. BC150609.1, and reproduced below (SEQ ID NO:7):

>BC150609.1
gagcccttggaccaaactcgcctgcgccgagagccgtccgcgtagagcgc
tccgtctccggcgagatgtccgagcgcaaagaaggcagaggcaaagggaa
gggcaagaagaaggagcgaggctccggcaagaagccggagtccgcggcgg
gcagccagagcccagccttgcctcccccaattgaaagagatgaaaagccag
gaatcggctgcaggttccaaactagtccttcggtgtgaaaccagttctga
atactcctctctcagattcaagtggttcaagaatgggaatgaattgaatc
gaaaaaacaaaccacaaaatatcaagatacaaaaaaagccagggaagtca
gaacttcgcattaacaaagcatcactggctgattctggagagtatatgtg
caaagtgatcagcaaattaggaaatgacagtgcctctgccaatatcacca
tcgtggaatcaaacgagatcatcactggtatgccagcctcaactgaagga
gcatatgtgtcttcagagtctcccattagaatatcagtatccacagaagg
agcaaatacttcttcatctacatctacatccaccactgggacaagccatc
ttgtaaaatgtgcggagaaggagaaaactttctgtgtgaatggaggggag
tgcttcatggtgaaagacctttcaaaccccctcgagatacttgtgcaagtg
ccaacctggattcactggagcaagatgtactgagaatgtgcccatgaaag
tccaaaaccaagaaaaggcggaggagctgtaccagaagagagtgctgacc
ataaccggcatctgcatcgccctccttgtggtcggcatcatgtgtttggt
ggcctactgcaaaaccaagaaacagcggaaaaagctgcatgaccgtcttc
ggcagagccttcggtctgaacgaaacaatatgatgaacattgccaatggg
cctcaccatcctaacccaccccccgagaatgtccagctggtgaatcaata
cgtatctaaaaacgtcatctccagtgagcatattgttgagagagaagcag
agacatccttttccaccagtcactatacttccacagcccatcactccact
actgtcacccagactcctagccacagctggagcaacggacacactgaaag
catcctttccgaaagccactctgtaatcgtgatgtcatccgtagaaaaca
gtaggcacagcagcccaactgggggcccaagaggacgtcttaatggcaca
ggaggccctcgtgaatgtaacagcttcctcaggcatgccagagaaacccc
tgattcctaccgagactctcctcatagtgaaaggtatgtgtcagccatga
ccacccggctcgtatgtcacctgtagatttccacacgccaagctccccc
aaatcgcccccttcggaaatgtctccaccccgtgtccagcatgacggtgtc
catgccttccatggcggtcagccccttcatggaagaagagagacctctac
ttctcgtgacaccaccaaggctgcgggagaagaagtttgaccatcaccct
cagcagttcagctccttccaccacaaccccgcgcatgacagtaacagcct
ccctgctagccccttgaggatagtggaggatgaggagtatgaaacgaccc
aagagtacgagccagcccaagagcctgttaagaaactcgccaatagccgg
cgggccaaaagaaccaagcccaatggccacattgctaacagattggaagt
ggacagcaacacaagctcccagagcagtaactcagagagtgaaacagaag
atgaaagagtaggtgaagatacgccttcctgggcatacagaaccccctg
gcagccagtcttgaggcaacacctgccttccgcctggctgacagcaggac
taacccagcaggccgcttctcgacacaggaagaaatccaggccaggctgt
ctagtgtaattgctaaccaagcccctattgctgtataaaacctaaataaa
cacatagattcacctgtaaaactttattttatataataaagtattccacc
ttaaattaaacaatttattttattttagcagttctgcaaatagaaaacag
gaaaaa By "Neuregulin 1 (NRG1) polypeptide" is meant a polypeptide or fragment thereof having at least about 85% amino acid identity to NCBI Accession No. AAI50610.1 and having Neuregulin 1 (NRG1) binding activity, as reproduced below (SEQ ID NO:8):

>AAI50610.1
MSERKEGRGKGKGKKKERGSGKKPESAAGSQSPALPPQLKEMKSQESAAG
SKLVLRCETSSEYSSLRFKWFKNGNELNRKNKPQNIKIQKKPGKSELRIN
KADLADSGEYMCKVISKLGNDSASANITIVESNEIITGMPASTEGAYVSS
ESPIRISVSTEGANTSSSTSTSTTGTSHLVKCAEKEKTFCVNGGECFMVK
DLSNPSRYLCKCQPGFTGARCTENVPMKVQNQEKAEELYQKRVLTITGIC
IALLVVGIMCLVAYCKTKKQRKKLHDRLRQSLRSERNNMMNIANGPHHPN
PPPENVQLVNQYVSKNVISSEHIVEREAETSFSTSHYTSTAHHSTTVTQT
PSHSWSNGHTESILSESHSVIVMSSVENSRHSSPTGGPRGRLNGTGGPRE
CNSFLRHARETPDSYRDSPHSERYVSAMTTPARMSPVDFHTPSSPKSPPS
EMSPPVSSMTVSMPSMAVSPFMEEERPLLLVTPPRLREKKFDHHPQQFSS
FHHNPAHDSNSLPASPLRIVEDEEYETTQEYEPAQEPVKKLANSRRAKRT
KPNGHIANRLEVDSNTSSQSSNSESETEDERVGEDTPFLGIQNPLAASLE
ATPAFRLADSRTNPAGRFSTQEEIQARLSSVIANQDPIAV

By "Neuregulin 1β (NRG1β) nucleic acid molecule" is meant a polynucleotide encoding an NRG1 polypeptide. An exemplary NRG1β nucleic acid molecule is provided at NCBI Accession No. NM_001322205.1 and reproduced below (SEQ ID NO:9):

>NM_001322205.1
ggcttaactgatgcctgcctgcctctctttgatttgatggcctttattcc
ttctaattggataaaataggaagtcactggcagtcctgtgtggctgggga
tactgattttactcagaccagcctgcagctctagagtgtgggtagagagc
ggggagtggggtgggagaggggagggaaagagagagaggagagaggac
gggcttggatgaagaagggaaagaaagagaaagagactgaagcagagaag
agccgcagaggaagaaagtgaatgagcactcaagaaggacaaagaggagt
agtcggggtggggtggaggcagggcgggaagggagtgaccgcccctcc
tggctgcactcttgcctccggagccctctgatcctgtttgcagtgatgct
ccgagggcaggcacctgctgctctgtaatgattcagccccttcagccgt
cgtcgcgttaacaacaggatgctgttgctattgtcactactgcctctc
ctgccgccgctgctgctgccgccgccgccaccgccgctggtcctccttct
gcttttacttctcctgcatgacagttgttttcttcatctgagcagacacc
agcttcagatgctcgaggtgagaaacatgcctttcagtttgggctactgg
tttacttaattaatcagccggcagctccgtcgatctattttcgtccctgt
cctcttgacgagcccgggatggtttggagtagcatttaaaagaactagaa -continued

```
aagtggcccagaaacagcagcttaaagaattattacgatatactttgatt
ttgtagttgctaggagcttttcttccccccttgcatctttctgaactctt
cttgattttaataatggccttggacttggacgatttatcgatttccccct
gtaagatgctgtatcatttggttgggggggcctctgcgtggtaatggacc
gtgagagcggccaggccttcttctggaggtgagccgatggagatttattc
cccagacatgtctgaggtcgccgccgagaggtcctccagcccctccactc
agctgagtgcagaccatctcttgatgggcttccggcagcagaagacatg
ccagagcccagactgaagatgggagaaccccctggactcgtgggcctggc
cgtgccctgctgtgcgtgcctagaagctgagcgcctgagaggttgcctca
actcagagaaatctgcattgtccccatcctggcttgcctggtcagcctc
tgcctctgcatcgccggcctcaagtgggtatttgtggacaagatctttga
atatgactctcctactcaccttgaccctggggggttaggccaggaccta
ttatttctctggacgcaactgctgcctcagctgtgtgggtgtcgtctgag
gcatacacttcacctgtctctagggctcaatctgaaagtgaggttcaagt
tacagtgcaaggtgacaaggctgttgtctcctttgaaccatcagcggcac
cgacaccgaagaatcgtattttttgccttttctttcttgccgtccactgcg
ccatccttcccttcacccaccggaaccctgaggtgagaacgcccaagtc
agcaactcagccacaaacaacagaaactaatctccaaactgctcctaaac
tttctacatctacatccaccactgggacaagccatcttgtaaaatgtgcg
gagaaggagaaaactttctgtgtgaatggaggggagtgcttcatggtgaa
agaccttcaaaccctcgagatacttgtgcaagtgcccaaatgagttta
ctggtgatcgctgccaaaactacgtaatggccagcttctacaagcatctt
gggattgaatttatggaggcggaggagctgtaccagaagagagtgctgac
cataaccggcatctgcatcgccctccttgtggtcggcatcatgtgtgtgg
tggcctactgcaaaaccaagaaacagcggaaaaagctgcatgaccgtctt
cggcagagccttcggtctgaacgaaacaatatgatgaacattgccaatgg
gcctcaccatcctaacccaccccccgagaatgtccagctggtgaatcaat
acgtatctaaaaacgtcatctccagtgagcatattgttgagagagaagca
gagacatccttttccaccagtcactatacttccacagcccatcactccac
tactgtcacccagactcctagccacagctggagcaacggacacactgaaa
gcatcctttccgaaagccactctgtaatcgtgatgtcatccgtagaaaac
agtaggcacagcagcccaactgggggcccaagaggacgtcttaatggcac
aggaggccctcgtgaatgtaacagcttcctcaggcatgccagagaaaccc
ctgattcctaccgagactctcctcatagtgaaaggtatgtgtcagccatg
accaccccggctcgtatgtcacctgtagatttccacacgccaagctcccc
caaatcgccccttcggaaatgtctccacccgtgtccagcatgacggtgt
ccatgccttccatggcggtcagcccttcatggaagaagagagacctcta
cttctcgtgacaccaccaaggctgcgggagaagaagtttgaccatcaccc
tcagcagttcagctccttccaccacaaccccgcgcatgacagtaacagcc
tccctgctagccccttgaggatagtggaggatgaggagtatgaaacgacc
caagagtacgagccagcccaagagcctgttaagaaactcgccaatagccg
```

-continued

```
gcgggccaaaagaaccaagcccaatggccacattgctaacagattggaag
tggacagcaacacaagctcccagagcagtaactcagagagtgaaacagaa
gatgaaagagtaggtgaagatacgcctttcctgggcatacagaaccccct
ggcagcagtcttgaggcaacacctgccttccgcctggctgacagcagga
ctaacccagcaggccgcttctcgacacaggaagaaatccaggccaggctg
tctagtgtaattgctaaccaagacccctattgctgtataaaaacctaaataa
acacatagattcacctgtaaaactttattttatataataaagtattccac
cttaaattaaacaatttattttattttagcagttctgcaaatagaaaaca
ggaaaaaaacttttataaattaaatatatgtatgtaaaaatgtgttatgt
gccatatgtagcaattttttacagtattttcaaaacgagaaagatatcaat
ggtgcctttatgttatgttatgtcgagagcaagttttgtacagttacagt
gattgcttttccacagtatttctgcaaaacctctcatagattcagttttt
gctggcttcttgtgcattgcattatgatgttgactggatgtatgatttgc
aagacttgcaactgtccctctgtttgcttgtagtagcacccgatcagtat
gtcttgtaatggcacatccatccagatatgcctctcttgtatgaagtt
ttctttgctttcagaatatgaaatgagttgtgtctactctgccagccaaa
ggtttgcctcattgggctctgagataatagtagatccaacagcatgctac
tattaaatacagcaagaaactgcattaagtaatgttaaatattaggaaga
aagtaatactgtgatttaaaaaaaactatattattaatcagaagacagct
tgctcttactaaaaggagctctcatttacttttatttgattttatttttct
tgacaaaaagcaacagttttagggatagcttagaaaatgggttctggctt
gctatcagggtaaatctaacaccttacaagaggactgagtgtcactttct
ctctgggggaatgatccagcagcttatctagttgacaatcaaaacacggc
tgataaaggtgcaatcatttctgacatgtattttttcactgattttgaagc
tagtgattggttgtgtcttcttggctcaaaaagaagcatattacggcaca
aaaagcccagcccagacagcacatgcagcattttgtctgaaatacttcta
gagtcaaacgtgcctgctgtatacagcgatgacttgtcatcataggaag
tatttccatcgtagagtgttcagaaggagtgactgtataggtggagagaa
gcttagtgactccgttgaaattttaaaatgtggatgaccacccctttctc
cccttatttttctttatctttccatgttgccttgatcaggtcataact
atgcatgaacatttttatcaggaatggccgatgtgtatgtgatttgtaa
tcacaagtaatgattcatcaggaaatgtcaatcctgttggaaagattgca
ccttttacttgcagaagtgaccccacctgtgtcctgacctctccatttac
aggctctcacccatttcccccacctccttttaattttgctttactgtc
ataaagtaggactaagattggtctaagcattgcatgttcttttgtgatgg
taaatccaaaggaaggcctataagtattaacatttgaaataactgctaat
tcaggaaaatggaagaaaaaaaatttatttgaaacacagaacccatttcat
ggcctgcctgatatctgtgaaatcagggctggagctttacttaggattca
catggcctcctaggaaccatgggacaaatggggaaacaggttatcggggga
ttcatgaagtcagtgagagtaattgcttctttttttgcgggtgaactgaat
```

-continued
```
gtatttcttcaccaaatcttgatgttaacaattaaaaagaagaaatgaca tgcaagtaggtcttagcagaaaaatgcaggctgggcatgagtcatgttgt taccctcccacatgctcctacaatccacagagatgcctgtctgcaggttc ttgaagttattgttagtatttggtatctcaaattttttcgtcactgttcac atgccactttctctgtgcacagtggtatcctcatttgcttttttaacctac actgaggagtctttgtcaggttgcactgattttccaattctgcagtaatg agtaagctcacggcatggggaagaagacagtcagtccaatgaagttctct aaattattttaacattgcctttgaaggccttgactcatccttagctattt caatgaagaaattcctaccatgaatttaaaacccctaaaaattctgtttca aattctttgggcattggggtactcagatatcccattgtggaagaatttta agaataaatagaagtttctgttgagaaccatgagcaacatgtttcttaca atgagaattgctatgcatttaaaattgcaaatatatgaaaattgaag acaagaggaaattgtatttctaacttgattctgatcactcacagaggtgg catattattatagttgggacatcctttgcacccttcataaaaaaggccag ctgactgctcagcatcacctgccaaggccactagatttgtgtttacaggg gtatctctgtgatgcttgtcacatcactcttgaccacctctgttaataaa ttccgacagtgcagtggcgatcggagtgtgaacttatgttcccagcatat ggaaagctatcttaggttttaaggtagtagaaattgcccaggagtttgac agcaactttgtttcccgggtctaaaatcgtatcccactgaggtgtatgca gtggagcataatacatgcaaatacatgcaaaactccttttgtttcaccta agattcactttctatcttactttccctttcctgccagtgtgacttttgcc cccaagagtgcctggacagcattctagtttctacaaaatggtcctctgtg taggtaatgtgtcccaaacctgctatcacttttcttgtttcagtgtgact gtcttgttagaggtgaagtttatccagggtaacttgctcactaactattc ctttttatggcctggggttaaagggcgcatggctcacactggtgaaaata aggaaggcctggtcttatcttgtattaataatactggctgcattccacca gccagagatttctatctgcgaagacctatgaaacactgaagagaaatgta ggcagaaggaaatggccacatatcacaagttctattatatattcttttgt aaatacatattgtatattacttggatgttttcttatatcatttactgtct ttttgagttaatgtcagttttttactctctcaacttactatgtaacattgt aaataacataatgtcctttattatttatatttaagcatctaacatataga gttgttttcatataagtttaagataaatgtcaaaaatatatgttcttttg tttttctttgctttaaaattatgtatcttttcctttctttttttttaaga ataatttattgttcaggagaaagaatgtatatgtaactgaaactatctga agaatgcacattgaaggccgtgaggtactgataaactaaagaatttatta ttcaaaatactaagcaataagtaattgtgatttattaaagttttgtcca ttttccatgaaagacatactgcaataaaaatgctactctgtggaaaaaaa aaaaaaaaaaa
```

By "Neuregulin 1β (NRG1β) polypeptide" is meant a polypeptide or fragment thereof having at least about 85% amino acid identity to NCBI Accession No. NP_001309134.1 and having Neuregulin 1 (NRG1) binding activity, as reproduced below (SEQ ID NO:10):

```
>NP_001309134.1
MEIYSPDMSEVAAERSSSPSTQLSADPSLDGLPAAEDMPEPQTEDGRTPG

LVGLAVPCCALCEAERLRGCLNSEKICIVPILACLVSLCLCIAGLKWVFV

DKIFEYDSPTHLDPGGLGQDPIISLDATAASAVWVSSEAYTSPVSRAQSE

SEVQVTVQGDKAVVSFEPSAAPTPKNRIFAFSFLPSTAPSFPSPTRNPEV

RTPKSATQPQTTETNLQTAPKLSTSTSTTGTSHLVKCAEKEKTFCVNGGE

CFMVKDLSNPSRYLCKCPNEFTGDRCQNYVMASFYKHLGIEFMEAEELYQ

KRVLTITGICIALLVVGIMCVVAYCKTKKQRKKLHDRLRQSLRSERNNMM

NIANGPHHPNPPPENVQLVNQYVSKNVISSEHIVEREAETSFSTSHYTST

AHHSTTVTQTPSHSWSNGHTESILSESHSVIVMSSVENSRHSSPTGGPRG

RLNGTGGPRECNSFLRHARETPDSYRDSPHSERYVSAMTTPARMSPVDFH

TPSSPKSPPSEMSPPVSSMTVSMPSMAVSPFMEEERPLLLVTPPRLREKK

FDHHPQQFSSFHHNPAHDSNSLPASPLRIVEDEEYETTQEYEPAQEPVKK

LANSRRAKRTKPNGHIANRLEVDSNTSSQSSNSESETEDERVGEDTPFLG

IQNPLAASLEATPAFRLADSRTNPAGRFSTQEEIQARLSSVIANQDPIAV
```

By "NRG-BVN hybrid polypeptide" is meant a polypeptide or fragment thereof having at least about 85%, 90%, 91%, 92%, 93%, 94%, 95%, 96%, 97%, 98%, or 99% amino acid identity to the amino acid sequence below (SEQ ID NO:11):

```
>NRG-BVN-hybrid
GTSHLVKCPLSHEAYCVNGGECFMVKDLSNPSRYLCKCPNEFTGDRCQNY

VMASF
```

By "TGFα hybrid polypeptide" is meant a polypeptide or fragment thereof having at least about 85%, 90%, 91%, 92%, 93%, 94%, 95%, 96%, 97%, 98%, or 99% amino acid identity to the amino acid sequence below (SEQ ID NO:12):

```
>TGF-BVN-hybrid
NTENDCPLSHEAYCLHDGVCRFLVQEDKPACVCVVGYVGERCQFRDLRWW
DAR
```

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following detailed description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIGS. 1A-1B depict domains and features for a synthetic protein according to an exemplary embodiment of the disclosure. FIG. 1A depicts the amino acid sequence of BVN22E (SEQ ID NO: 2), including Targeted Signaling Pathway (TSP) domains 1 & 2 shown in single underline, two linker sequences shown in double underline, and an Immunogenic Carrier Domain shown in dotted underline. FIG. 1B shows a Clustal Omega alignment of the synthetic Epidermal Growth Factor (sEGF) regions of BVN22E (SEQ ID NO: 33) aligned with the corresponding regions of human EGF (hEGF) (SEQ ID NO: 35);

FIG. 4A shows a Western blot illustrating that BVN22E is able to stimulate phosphorylation of the Epidermal Growth Factor Receptor (EGFR) of A431 cells to the same extent as a similar molecule containing native human EGF domains, in a concentration-dependent manner. FIG. 4B shows the results of another assay without comparison with an EGF-based molecule;

FIG. 9 depicts a Western blot showing inhibition of the EGF signaling pathway by pooled sera (n=10) derived from mice immunized with either BVN22E or an immunogen containing chemically conjugated native human EGF (hEGF). Lanes 4-6 demonstrate that BVN22E immunization generated greater EGF-neutralizing capacity than an immunogen based upon native hEGF.

FIG. 13A shows a Coomassie stained SDS gel. FIG. 13B is a Western blot of the SDS gel in FIG. 13A, which has been stained with anti-TGFα antibodies to show that the synthetic TGFα molecule is recognized by two different neutralizing anti-TGFα antibodies. FIG. 13C is a Western blot of the SDS gel in FIG. 13A, which is been stained with anti-EGF antibodies to show that two different anti-EGF antibodies do not recognize the synthetic TGFα molecule.

DETAILED DESCRIPTION OF THE DISCLOSURE

Figure 2:
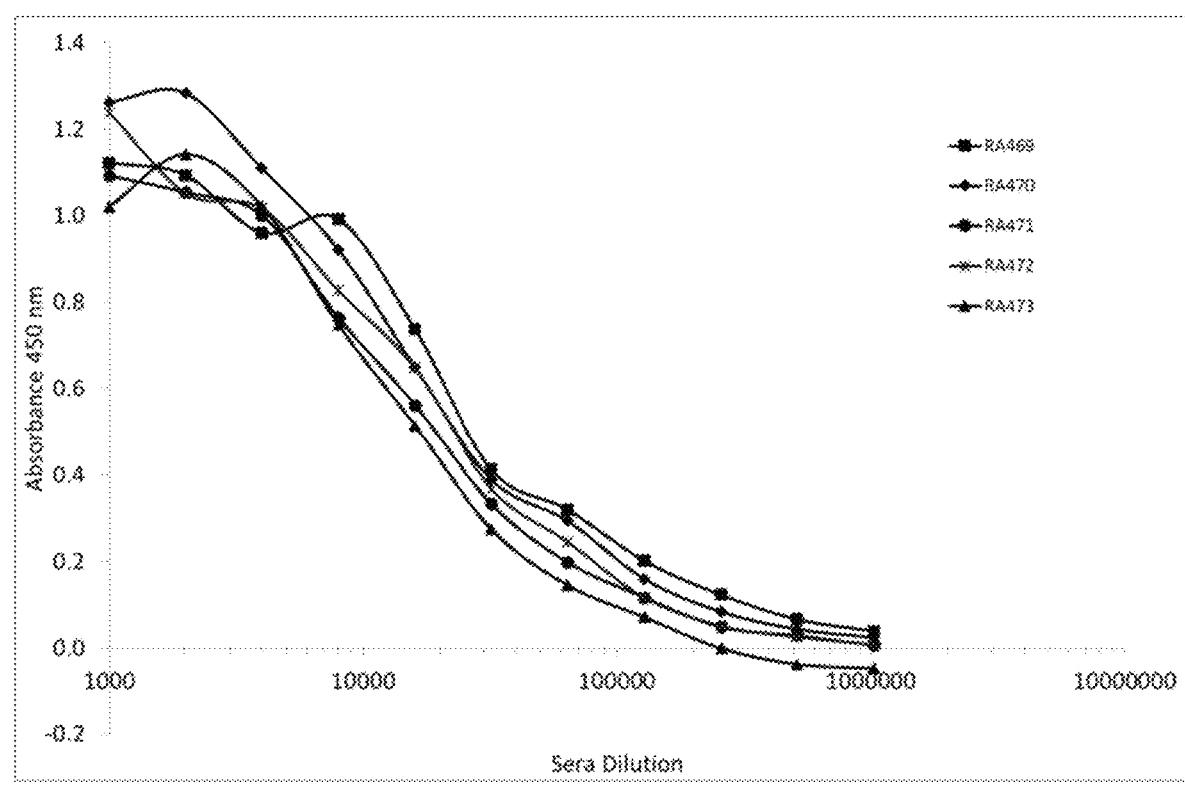
FIG. 2 shows a graph of the titration of purified IgG fraction from 5 rabbits immunized with BVN22E binding to immobilized recombinant human Epidermal Growth Factor (rhEGF) coated at a concentration of 1 μg/ml according to an exemplary embodiment of the disclosure.
Figure 3:
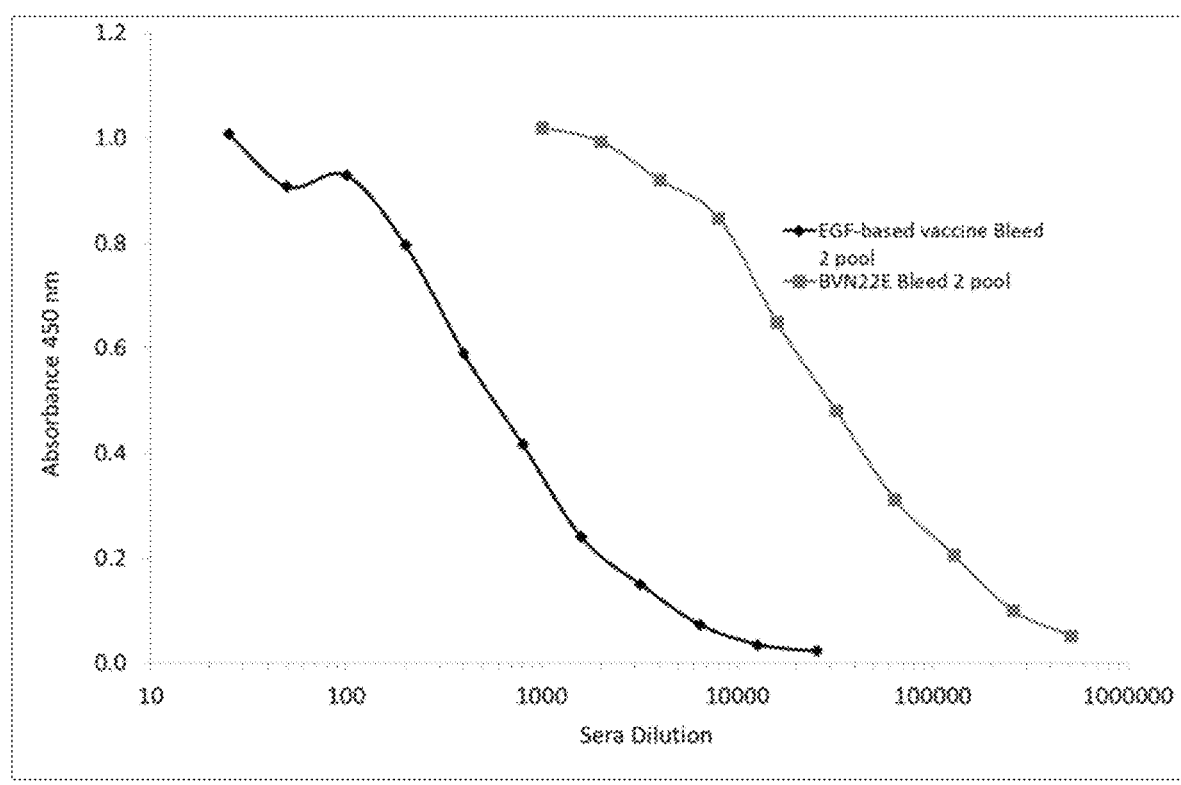
FIG. 3 shows a graph depicting a comparison of pooled IgG fraction from 5 rabbits after immunization with either BVN22E or an equivalent protein containing 2 native Epidermal Growth Factor (EGF) domains according to an exemplary embodiment of the disclosure.

The present disclosure is based, at least in part, on the discovery that synthetic proteins/molecules including one or more protein domains from a synthetic growth factor, one or more linker regions, and one or more immunogenic domains may be used as therapeutic molecules to treat a variety of diseases such as, for example, cancer. The synthetic molecules provide several unexpected advantages over the prior art. For example, unlike prior art human Epidermal Growth Factor (hEGF) molecules (e.g., U.S. Pat. No. 5,984,018 to Davila et al.) that are present in heterogeneous mixtures containing up to 12 different molecular species, the synthetic proteins/molecules described herein may be produced as a single molecule (e.g., a homogenous population of molecules). Additionally, the synthetic proteins/molecules described herein include ten active components per molecule (although the active components may be increased or decreased in multiples of 5, e.g., as part of a pentamer), whereas prior art hEGF molecules (e.g., U.S. Pat. No. 5,984,018 to Davila et al.) are highly variable in the number of active components present per molecule (e.g., the mean number of active components per molecule of Davila is 1.5). Moreover, the synthetic proteins/molecules described herein are much more straightforward to manufacture. For example, prior art hEGF molecules (e.g., U.S. Pat. No. 5,984,018) are made by chemically conjugating rP64k and recombinant human EGF (rhEGF) to produce a final molecule that consists of two molecules chemically conjugated to one another. This is in sharp contrast to the synthetic proteins/molecules described herein, which are a single synthetic molecule. Advantageously, the techniques herein provide novel synthetic proteins that may be used therapeutically to treat diseases such as, for example, cancer (e.g., cancer vaccines) with a higher immunogenic activity level than prior art methods (e.g., U.S. Pat. No. 5,984,018).

Overview

Cancer immunology is the study of interactions between an immune system and cancer cells such as, for example, tumors or malignancies. The initiation of an immune response, such as recognition of cancer-specific antigens that are expressed by human tumors and not expressed in normal tissues, is of particular interest. Generally, methods to control the division and proliferation of the malignant cells have focused on isolating these antigens and presenting them so that they are recognized by the immune system as non-self antigens to induce a specific immune response.

There are a significant number of growth factors identified at present, and most, if not all, have been shown to be important mediators of cell proliferation in various cancers in addition to being implicated in other disease conditions. Generally, growth factors are soluble serum proteins that recognize and bind to a group of growth factor receptors located on cell surfaces. Particular growth factors may be specific for a single receptor, or may bind to more than one closely related receptor with varying affinities. Similarly, some receptors bind to only a single growth factor ligand while others can bind to multiple related growth factors, again usually with differing affinities. Upon binding to its natural receptor, the cytoplasmic domain of the receptor is phosphorylated, and this initiates an intra-cellular signaling cascade that results in modulation of transcription of one or more genes and ultimately to progression through the cell cycle and cell proliferation.

Growth factors and their receptors are essential components of the normal processes of growth, development and repair, and their tissue distribution profiles and expression levels closely regulate cell growth. Numerous studies have shown that growth factors can stimulate proliferation of a variety of cell types both in vitro and in vivo (Cohen S., Carpenter G., PNAS USA 72, 1317, 1975, Witsch E et al: Physiology: 25(2):85-101, (2010)). Moreover, certain growth factors have been shown to stimulate proliferation in some cancer cell lines. For example epidermal growth factor (EGF) can stimulate some non-small cell lung carcinoma cells (Osborne C. K. et al. Can Res. 40, 2. 361 (1980)). Other growth factors such as vascular endothelial growth factor (VEGF), fibroblast growth factor (FGF), and platelet-derived growth factor (PDGF) are important in several oncology diseases, such as non-small cell lung cancer (NSCLC) (Ballas M S, Chachoua A., Onco Targets and Therapy: 4, 43-58 (2011)), prostate cancer, (Cox M E et al; Prostate 69 (1):33-40 (2009)), and breast cancer (Law J et al, Cancer Res; 68, 24: 10238-10346 (2008)).

High levels of various growth factor receptors have been reported in malignant tissues. For example, the epidermal growth factor receptor (EGFR) has been detected at unusually high levels in malignant tumors of epithelial origin, such as lung, breast, bladder, ovarian, vulva, colonic, pulmonary, brain and esophagus cancers. The role played by growth factors and their receptors in regulating tumor growth is unknown, but there are suggestions that growth factor receptor expression in tumor cells provides a mechanism for autocrine growth stimulation which leads to uncontrolled proliferation (Schlessinger J., Schreiber A. B., Levi A., Liberman T., Yarden Y. Crit. Rev. Biochem. 1983, 14 (2) 93-111). Further, Liao Y et al; Hum Pathol 36(11): 1186-1196 (2005) and Cox M E et al; Prostate: 69(1) 33-40 (2009) describe the role of increased Insular receptor and growth factor on metastatic prostate cancer.

One treatment strategy to target growth factor signaling in cancer therapy has been to use a passive immunotherapy (e.g., monoclonal antibodies) against the particular receptor/receptors involved. Such studies have demonstrated that the specific recognition by an antibody of the receptor that is able to inhibit the binding of the ligand can have an inhibitory effect on the mitogenic stimulation of malignant cells (SATO J. D., et al. Methods in Enzymology, vol. 146 pp 63-81, 1987). However, antibodies that are of murine origin will usually produce a human anti-mouse antibody response (HAMA), thus limiting them to a single administration.

Other treatment strategies have been to use an active immunotherapy with vaccines that contain the growth factor of interest to induce an immune response against the molecule to inhibit the proliferation effect of the growth factor on tumors. U.S. Pat. No. 5,984,018, to Davila et al, entitled Vaccine Composition Comprising Autologous Epidermal Growth Factor or a Fragment or a Derivative Thereof having Anti-tumor Activity and use Thereof in the Therapy of Malignant Diseases, discloses, for example, the use of a vaccine that contains a mixture of a growth factor and an immunogenic (i.e. non-human) carrier protein chemically conjugated together using glutaraldehyde. However, without being bound to any particular theory it is thought that chemical conjugation hinders immune responses against the vaccine.

This is a technically challenging approach, as it requires that the host generates an immune response to a 'self antigen', and vertebrate immune systems have evolved to prevent such responses from occurring. Where a strong immune response is generated against a self-antigen, for example, one that includes T-helper cell activation, an auto-immune disease state usually results. For many years it has been hypothesized that some auto-immune disorders, for example, lupus, multiple sclerosis (MS), diabetes etc., might be caused by early exposure to an environmental agent that includes immunogenic epitopes (T-cell epitopes) that closely mimic host self-epitopes. This could lead to the stimulation of T-helper cells that are cross reactive with host epitopes. Subsequent exposure to the environmental agent could then result in an anti-self immune response (Albert, L. J., and Inman, R. D New England Journal of Medicine, December 30th pp 2,068-2074, 1999). It has since been demonstrated that a viral antigen can indeed generate an anti-self immune response against a nerve cell protein (Levin, M. C. et. al, Nature Medicine vol 8 (5) pp 509-513, 2002).

U.S. Publ. No. 2006/0251654, to Casimiro et al, entitled Method for Treatment of Malignant and Infectious Chronic Diseases, (the '654 publication) discloses a method of treating a subject bearing a malignant or infectious chronic disease comprising the method of immunizing the subject with a vaccine containing a self-antigen associated with the malignant or infectious chronic disease that is coupled to a carrier protein; treating the subject with an immune modulator agent; and immunizing the subject again with the vaccine of the step 1, and an appropriate adjuvant selected from aluminum hydroxide and Montanide ISA 51 (Seppic, Paris, France). Unfortunately, the preparation of the vaccine by chemical conjugation is thought to hinder the immune response.

The majority of the vaccines described above exhibit a number of limitations, arising primarily from the method of manufacture and the potential lack of uniformity and homology of the protein product. The vaccines described above generally comprise a mixture of a recombinant carrier protein and polypeptides of human origin that are chemically conjugated using glutaraldehyde. Unfortunately, this reactive reagent can undesirably form covalent cross-linking bonds between varieties of chemical groups, and generally leads to a highly heterogeneous product. Thus, the resulting vaccines may comprise not only carrier protein molecules with varying numbers of the target human polypeptide attached (for example, 0, 1, 2, 3 etc.), but the human polypeptides can each be attached to the carrier via different atoms and so in different positions and in different orientations. Furthermore, both the target polypeptide and carrier protein molecules may be conjugated to themselves, resulting in various homo-multimers that may have no clinical efficacy and may not contribute to an anti-cancer patient immune response.

Synthetic Proteins/Molecules

The present disclosure provides a homogeneous synthetic protein/molecule for improving the presentation of the maximum number of growth factor epitopes, tumor antigen epitopes, and/or receptor binding sites as elements of an immunogenic synthetic protein/molecule. In one illustrative embodiment, a synthetic protein/molecule expressing all or portions of an immunogenic carrier domain (e.g., cholera toxin B (CT-B)), and a synthetic epidermal growth factor (sEGF), a tumor antigen, and/or a receptor is described. In alternative illustrative embodiments, the protein may express other immunogenic synthetic or recombinant proteins/molecules that are modeled based upon known immunogenic proteins. It is contemplated within the scope of the disclosure that such synthetic proteins/molecules may express polypeptides that are highly immunogenic to the human immune system. Preferably, the synthetic proteins/molecules confer additional properties to the chimeric protein such as, for example, high expression yield and ease of manufacture, oral stability and the ability to cross from gut to blood stream, and/or previous safe use in humans.

In an illustrative embodiment, the synthetic proteins/molecules disclosed herein may include or express a high proportion of a protein sequence derived from target self antigens, as a function of total molecular weight. This may be achieved, for example, by using a large protein model containing multiple growth factor epitopes. These growth factor epitopes may be multiple copies of whole or part of a single growth factor, or copies of whole or part of more than one different growth factor. These growth factor epitopes may be naturally occurring or synthetic (e.g., artificial). For example, BVN22E, an illustrative synthetic protein described herein, may have a molecular weight of about 120 kD. In an illustrative embodiment, the growth factor epitopes described herein may correspond to one or more domains within the growth factor (e.g., EGF targeted signaling pathway (TSP) domains). In an illustrative embodiment, an EGF domain may include the region which presents or constrains the β-loop, e.g., the region defined by about cysteine 6 to about cysteine 42, the region defined by about cysteine 6 to about cysteine 31 or the region defined by about cysteine 22 about cysteine 33 or the region defined by about cysteine 22 about cysteine 31 or the region defined by about cysteine 62 about cysteine 14 of the synthetic protein sequence (e.g., FIG. 1A). Without being bound by any particular theory, it is contemplated within the scope of the disclosure that different regions or sub-regions between cysteine 6 and cysteine 42 may have beneficial effects when incorporated into the synthetic proteins/molecules of the disclosure. For example, the following regions may have beneficial effects: the region between cysteine 6 and cysteine 14, the region between cysteine 6 and cysteine 20, the region between cysteine 6 and cysteine 31, the region between cysteine 6 and cysteine 33, and the region between cysteine 6 and cysteine 42. It is also contemplated within scope of the disclosure that the reverse progressive sequence may also be beneficial. For example, the following regions may have beneficial effects: the region between cysteine 42 and cysteine 33, the region between cysteine 42 and cysteine 31, the region between cysteine 42 and cysteine 20, the region between cysteine 42 and cysteine 14, and the region between cysteine 42 and cysteine 6. It is further contemplated within the scope of the invention that specific intervals within the region between cysteine 6 and cysteine 42 may provide beneficial effects when incorporated into the synthetic proteins/molecules of the disclosure (e.g., the region between cysteine 6 and cysteine 14, the region between cysteine 14 and cysteine 20, the region between cysteine 20 and cysteine 31, and the region between cysteine 33 and cysteine 42).

According to the disclosure, the expressions of the growth factor epitopes should be folded allowing their natural conformation to be substantially retained and presented to components of the host immune system in such a way as to elicit a robust host immune response to said epitopes. Examples of suitable natural protein models to model an epitope supporting domain of a synthetic proteins/molecules include, but are not limited to, cholera toxin B sub-unit, *E. coli* heat-labile LT and LT-II enterotoxin B subunits, veratoxin, pertussis toxin, *C. jejuni* enterotoxin, Shiga toxin, *listeria* toxin, tetanus toxoid, diphtheria toxoid, *N. meningitidis* outer membrane protein, bacteriophage coat protein, adenovirus and other viral coat proteins. Alternatively, a non-self component of the protein can be small. At a minimum, the non-self sequence(s) should comprise about 9, 10, 11 or more amino acids in length, and include either entirely or in-part at least one human T-cell epitope. As described herein, non-natural synthetic polypeptides (e.g., BVN22E) may be used that fulfill the requirements of conferring immunogenicity to the whole protein and allowing appropriate presentation of growth factors, receptors, tumor antigens or epitopes thereof to the host immune system.

According to the disclosure, the synthetic proteins/molecules provided herein-whether growth factors or parts thereof, cellular receptors or parts thereof, or tumor antigens or parts thereof—are related to a broad range of cellular pathways involved in chronic disease, growth factor based or receptor based cancers, and/or solid tumors for use as tumor antigens within the said synthetic proteins. The proteins are in the form of a synthetic proteins/molecules and may be useful in treating chronic diseases, for example, breast, lung, bladder, ovarian, vulva, colonic, pulmonary, brain, colorectal, intestinal, head and neck, and esophagus cancers. As different tumor antigens can be expressed and multiple cellular receptors and growth factors over expressed in the said diseases, the proteins described hereunder can contain one or more different tumor antigens, one or more different receptors or growth factors of one or multiple cellular pathways associated with the disease. These proteins are called multivalent.

In an illustrative embodiment, a protein comprised of a homogeneous synthetic proteins/molecules expressing one or more epidermal growth factor (EGF) neutralizing domains (e.g., TSP domains) is disclosed. The protein may be in the form of a synthetic proteins/molecules and may be useful in treating chronic diseases, for example, breast, lung, bladder, ovarian, vulva, colonic, pulmonary, brain, colorectal, head and neck, and esophagus cancers. In an illustrative embodiment, the protein is a synthetic proteins/molecules expressing or including synthetic EGF sequences and CT-B sequences, as shown in FIG. 1A. In an illustrative embodiment, a growth factor component of the synthetic protein sequence may include a sequence that is less than 80% identical to EGF. For example, a growth factor component may include an EGF sequence with 11 amino acid substitutions that may increase the immunogenicity of the growth factor portion of the synthetic protein sequence. Without being bound by theory, it is believed that the region of EGF that 'presents' or constrains the β-loop (e.g., the region defined by Cys6 to Cys31) may be an important to include in the synthetic protein and amenable to target for amino acid modification. In an illustrative embodiment, regions outside of Cys6 to Cys31 may also be targeted for modification (e.g., E11 and A12).

In an illustrative embodiment, the TSP1 and TSP2 domains of hEGF may be modified as shown in FIG. 1B to create synthetic EGF (sEGF) regions to be included in a synthetic protein/molecule herein.

In an illustrative embodiment, the synthetic proteins/molecules disclosed herein may include all, or a portion of, growth factors including without limitation grow factors such as, for example, Neuregulin 1β (NRG1β), Transforming Growth Factor α (TGFα), Vascular endothelial growth factor (VEGF), and the like.

In other illustrative embodiments, the synthetic proteins/molecules described herein may include one or more linkers or spacers. One or more of the embodiments described above include sEGF fused to CT-B such that the sEGF portion of the synthetic molecule is separated from the CT-B portion by a GGSGGTSGGGGGSG linker. These resulting recombinant or chimeric proteins essentially included sEGF fused directly to CT-B. In other illustrative embodiments, the EGF and CT-B components of the chimeric protein are effectively separated by 3 to 14 amino acids, which form a flexible spacer or linker between the two domains. It is contemplated within the scope of the disclosure that the linker may be 3, 4, 5, 6, 7, 8, 9, 10, 11, 12, 13, or 14 amino acids in length. In some cases in which a growth factor has a larger size (e.g., human growth factor), it may be useful to use a longer linker sequence. The following exemplary linkers may be used and include, but are not limited to, the following: SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29). One of skill in the art will appreciate that there are many other sequences/combinations of primarily 'G' and 'S' that would also serve as useful linker sequences.

Without being bound by any particular theory, it is contemplated that the synthetic proteins/molecules disclosed herein provide significant clinical benefits. For example, the synthetic proteins/molecules disclosed herein may be expressed in bacterial systems at commercial scale and purity, while producing stable polypeptides that fold correctly and are functional. Additionally, the synthetic proteins/molecules disclosed herein are able to form a pentamers. Additionally, the synthetic proteins/molecules disclosed herein have the advantageous property of requiring much lower levels of protein for vaccination because the amount of carrier necessary significantly lower than prior art methods (e.g., U.S. Pat. No. 5,984,018 to Davila et al.). In this regard, the synthetic proteins/molecules disclosed herein are able to deliver more growth factor to a patient in a significantly lower volume of vaccine.

Adjuvant

Certain illustrative embodiments as provided herein include synthetic proteins/molecules according to the disclosure within vaccine compositions and immunological adjuvant compositions, including pharmaceutical compositions, that contain, in addition to synthetic proteins/molecules at least one adjuvant, which refers to a component of such compositions that has adjuvant activity. An adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. In certain illustrative embodiments disclosed herein a desired antigen and or antigens contain within a protein carrier, and optionally one or more adjuvants, may so alter, e.g., elicit or enhance, an immune response that is directed against the desired antigen and or antigens which may be administered at the same time or may be separated in time and/or space (e.g., at a different anatomic site) in its administration, but certain illustrative embodiments are not intended to be so limited and thus also contemplate administration of synthetic proteins/molecules in a composition that does not include a specified antigen but which may also include but is not limited to one or more co-adjuvant, an imidazoquinline immune response modifier.

Accordingly and as noted above, adjuvants include compositions that have adjuvant effects, such as saponins and saponin mimetics, including QS21 and QS21 mimetics (see, e.g., U.S. Pat. No. 5,057,540; EP 0 362 279 B1; WO 95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al, 2005 Vaccine 23:5263).

Detergents including saponins are taught in, e.g., U.S. Pat. No. 6,544,518; Lacaille-Dubois, M and Wagner H. (1996 Phytomedicine 2:363-386), U.S. Pat. No. 5,057,540, Kensil, Crit. Rev Ther Drug Carrier Syst, 1996, 12 (1-2): 1-55, and EP 0 362 279 B1. Particulate structures, termed Immune Stimulating Complexes (ISCOMS), comprising fractions of Quil A (saponin) are hemolytic and have been used in the manufacture of vaccines (Morein, B., EP 0 109 942 B 1). These structures have been reported to have adjuvant activity (EP 0 109 942 B 1; WO 96/1 1711). The hemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-hemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/1 1711. Other saponins which have been used in systemic vaccination studies include those derived from other plant species such as *Gypsophila and Saponaria* (Bomford et al, Vaccine, 10(9):572-577, 1992). Escin is another detergent related to the saponins for use in the adjuvant compositions of the embodiments herein disclosed. Escin is described in the Merck index (12.sup.th Ed. entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al, U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al, J. Am. Pharm. Assoc., 1934, 23, 664; and Rubenstroth-Bauer, Physiol. Chem., 1955, 301, 621.

Other adjuvants or co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a vaccine composition or a immunological adjuvant include Pluronic® L121 (BASF Corp., Mount Olive, N.J.; see, e.g., Yeh et al, 1996 Pharm. Res. 13: 1693).

Certain further illustrative embodiments contemplate immunological adjuvants that include but are not limited to an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide monooleate.

Immune response modifiers such as imidazoquinoline immune response modifiers are also known in the art and may also be included as adjuvants or co-adjuvants in certain presently disclosed embodiments.

As also noted above, one type of adjuvant or co-adjuvant for use in a vaccine composition according to the disclosure as described herein may be the aluminum co-adjuvants, which are generally referred to as "alum." Alum co-adjuvants are based on the following: aluminum oxy-hydroxide; aluminum hydroxyphosphoate; or various proprietary salts. Alum co-adjuvants are be advantageous because they have a good safety record, augment antibody responses, stabilize antigens, and are relatively simple for large-scale production. (Edelman 2002 Mol. Biotechnol. 21: 129-148; Edelman, R. 1980 Rev. Infect. Dis. 2:370-383.)

Pharmaceutical Compositions

In certain illustrative embodiments, the pharmaceutical composition is a vaccine composition that comprises both the synthetic proteins/molecules according to the disclosure and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For vaccines comprising synthetic proteins/molecules, about 0.01 µg/kg to about 100 mg/kg body weight will be administered, typically by the intradermal, subcutaneous, intramuscular or intravenous route, or by other routes.

It will be evident to those skilled in the art that the number and frequency of administration will be dependent upon the response of the host. "Pharmaceutically acceptable carriers" for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic sonophoretic, passive transdermal, microneedle administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

In an illustrative embodiment, the epitope or receptor supporting domain of the synthetic protein/molecule, whether derived from a natural or synthetic polypeptide sequence, should have the capacity to self-assemble into oligomeric multimers under appropriate chemical/environmental conditions, or to be reduced to monomers under alternative conditions. Ideally, multimerisation domains will assemble into stable multimers with a discreet number of sub-units, for example dimers, trimers, tetramers, pentamers, etc., such that a product of homogeneous size is generated. Examples of natural polypeptides include, but are not limited to, leucine zippers, lac repressor protein, streptavidin/avidin, cholera toxin B sub-unit, *Pseudomonas* trimerization domain, and viral capsid proteins.

In an illustrative embodiment, a process of preparing a multivalent molecule is disclosed. In this illustrative embodiment, the process includes assembling multimers from monomeric sub-units to form a synthetic protein including one or more tumor antigens, receptors, and/or a growth factors or parts thereof.

In another illustrative embodiment, a process of preparing a vaccine formulation is disclosed. In this illustrative embodiment, the process includes mixing one or more single monovalent multimers together preparing a multivalent vaccine including a synthetic protein/molecule including one or more tumor antigens, receptors, and/or a growth factors or parts thereof.

In yet another illustrative embodiment, a process for treating a patient is disclosed. In this illustrative embodiment, the process includes administering separately to the patient one or more monovalent, one tumor antigen, receptor, and/or growth factor, recombinant proteins in a same day or at alternate days or times during a vaccination period.

While the synthetic protein/molecule is described as including or expressing one or more of all or a portion of at least one sequence of the tumor antigens, the growth factors, and/or the receptors, and the CT-B sequence, the synthetic protein/molecule may include the natural CT-B sequence or a sequence substantially similar to the natural CT-B sequence and/or a synthetic sequence. While the synthetic protein/molecule is described as including or expressing the CT-B sequence, the synthetic protein/molecule may include or express a derivation of the CT-B sequence or a sequence that is substantially similar to the CT-B sequence.

While the homogeneous synthetic proteins/molecules expressing or incorporating one or more tumor antigens, synthetic growth factors, and/or receptors have been described and illustrated in connection with certain embodiments, many variations and modifications will be evident to those skilled in the art and may be made without departing from the spirit and scope of the disclosure. The disclosure is thus not to be limited to the precise details of methodology or construction set forth above as such variations and modification are intended to be included within the scope of the disclosure.

EXAMPLES

The present disclosure is further illustrated by the following examples, which should not be construed as limiting.

The contents of all references, GenBank Accession and Gene numbers, and published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1: BVN22E Immunization Protocol

BVN22E was expressed in the cytoplasm of 500 milliliters (ml) BL21 pLys6 cells as inclusion bodies using standard protocols. Exclusion bodies were isolated by centrifugation, washed, and solubilized in 10 ml 8M Urea 2 mM DTT. One milliliter of the protein solution was re-folded by drop-wise dilution into 100 ml 50 mM Tris-HCl buffer 2 M Urea, 1 mM DTT pH 7.4 containing a redox buffer (GSH/GSSG) over a period of 1 hour. The protein was stored at 4° C. to allow folding to continue.

The largely folded protein was buffer-exchanged into 50 mM Trsi-HCl pH 8.0 by dialysis, and then purified by ion exchange chromatography (IEX) on a 'Hitrap' HP Q column. The fraction equating to eluted BVN22E was isolated by step wise elution, and further purified on a Sephadex 75 size exclusion column to separate the pentameric protein from other oligomeric states. This was then further purified to remove endotoxin using standard methodologies.

The protein was immunized into rabbits (n=5) at 100 μg/injection in Freund's complete (prime injection only) or Freund's incomplete (boost injections) using the following schedule:

| | |
|---|---|
| Day 0 | Pre-bleed |
| Day 0 | Immunization |
| Week 4 | Boost 1 |
| Week 6 | Test bleed 1 |
| Week 8 | Boost 2 |
| Week 9 | Test bleed 2 |
| Week 12 | Boost 3 |
| Week 13 | Final bleed |

Sera from individual rabbits was purified by standard caprylic acid precipitation to isolate the IgG fraction, and purified antibodies were either pooled or assayed individually.

Example 2: Binding ELISA Assay

Plates were coated for 1 hour at room temperature with 100 μl rhEGF at 1 μg/ml, washed ×3 with PBS, and blocked with 200 μl/well 2% BSA for 2 hours. Plates were washed as described, and 200 μl/well of purified IgG was added to the first well. One hundred microliters from the first wells was pipetted into 100 μl PBS in adjacent wells, and serial 2-fold dilutions were made across the plate. The plates were incubated at room temperature for 1 hour and washed as before. HRP-labeled anti-rabbit secondary antibody was added as prescribed and incubated for 1 hour at room temperature before washing with PBS-tween. One hundred microliters/well TMB substrate was added, and incubated until color developed. Reactions were stopped with 50 μl 1 M $H_2SO_4$ and plates read at 450 nm.

As shown in FIG. 2, titration of purified IgG fraction from each of the five immunized rabbits in the rhEGF binding assay was approximately consistent across the 1,000-1,000,000 fold serial dilution range, indicating a strong immune response to BVN22E in each of the immunized rabbits.

To test the specificity and sensitivity of the BVN22E immune response, the purified IgG fractions from each of the five rabbits were pooled and compared in the rhEGF binding assay to purified IgG fractions from a pool of five that has been immunized with an equivalent protein containing two native EGF domains (lower sequence in FIG. 1B).

Example 3: A431 EGFR Phosphorylation (EGF Signaling) Assay

A431 cells were cultured to 50% confluence in T75 culture flasks under standard conditions in DMEM supplemented with 10% FBS. Cells were washed by pipetting-off the media and adding 10 ml of pre-warmed PBS. This was then removed and 2 ml of Trypsin was added. The flask was incubated for 20 minutes (or longer if required) to allow cells to detach from the flask. Ten milliliters of fresh DMEM was added to the flask, and the cells were then transferred to a 50 ml 'Falcon' tube. The cells were pelleted gently at 250×g for 10 minutes, the supernatant decanted to remove the trypsin, and the cells were then resuspended in 10 ml of fresh DMEM.

Two hundred microliters cells were pipetted into each well of 96-well plate, which was then incubated overnight to allow the cells to adhere to the plate. The next day all wells were washed once with PBS, and fresh serum-free media was added. The plates were then incubated for another day/overnight to enable a basal level of EGF-R phosphorylation to become established.

To assay the cells, the media was removed, and one of the following was added:
i) 100 μl fresh serum-free media (basal EGF-R activation);
ii) 100 μl SFM+rhEGF @ 30 ng/ml (EGF-R activation control);
iii) 100 μl SFM+control (neutralizing) antibody at desired concentration (5 μg/ml); or
iv) 100 μl SFM+sample antibody at desired concentration+/−rhEGF @ 30 ng/ml.

For wells requiring rhEGF and antibody (control or sample), 500 μl reaction was prepared in Eppendorf tubes and pre-incubated for 1 hour @ 37° C. One hundred microliters was then applied to A431 cells as above.

In all assays, quadruplicate wells were prepared. The cells were incubated with the reaction media for 60 minutes at 37° C. in 5% $CO_2$.

After incubation time, media was removed by pipetting and 40 μl lysis buffer (6M urea, 50 Mm TrisHCl pH7.9, 2% SDS, 5% Beta-mercaptoethanol) per well added. The plate was incubated for 10 minutes on the bench to lyse cells. Reactions from 4 replicate wells for each sample were pipetted up and down gently, scraping bottom of well to release all lysate, and transferred into a fresh Eppendorf tube. Twenty microliters loading dye was added to each tube, and tubes boiled for 10 minutes followed by centrifugation for 5 minutes top speed.

Samples were either used for Western blots directly or stored at 4° C. until needed.

Westerns blots were performed in duplicate, with one membrane being probed with rabbit anti-EGFR antibody (Abcam ab52894) to normalize receptor expression levels between samples, and the second with phosphorylated EGFR-specific rabbit antibody (Abcam ab32578) to assess receptor activation levels. They were both developed with HRP-labelled anti-rabbit antibody (Abcam ab97051).

Figure 4A:
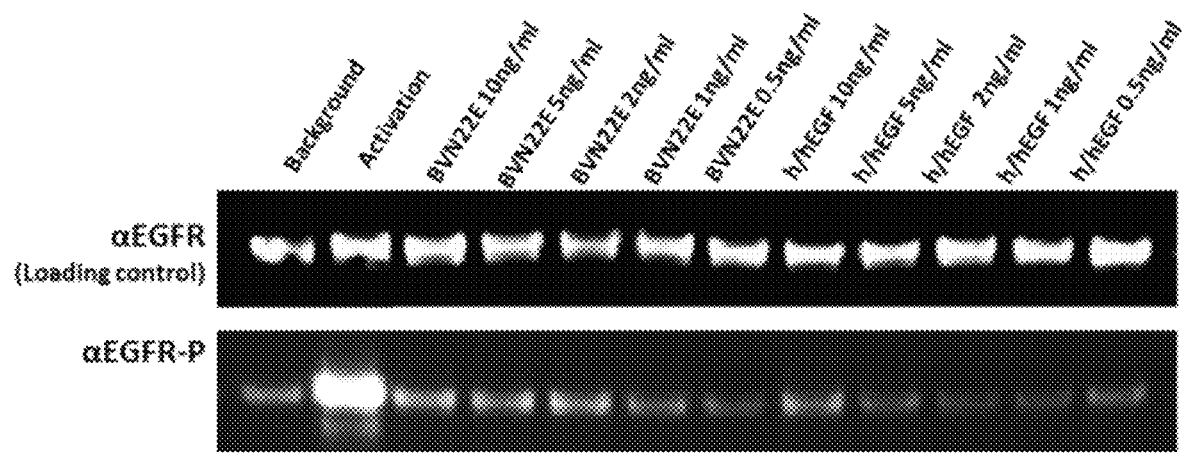
FIGS. 4A-4B show Western blots illustrating the ability of BVN22E to stimulate phosphorylation.
Figure 4B:
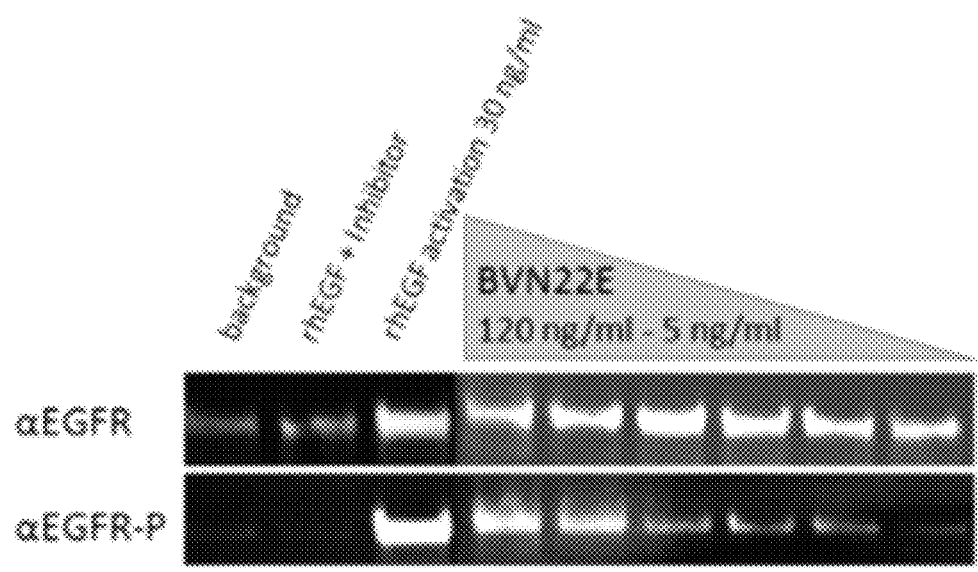

As shown in FIGS. 4A-4B, BVN22E is able to stimulate phosphorylation of EGFR in A431 cells. In particular, FIG. 4A shows a Western blot illustrating that BVN22E is able to stimulate phosphorylation of the EGFR of A431 cells to the same extent as a similar molecule containing native human EGF domains, and that this stimulation occurs in a concentration-dependent manner. FIG. 4B shows the results of a similar assay, but without comparison to an EGF-based molecule.

Figure 5:
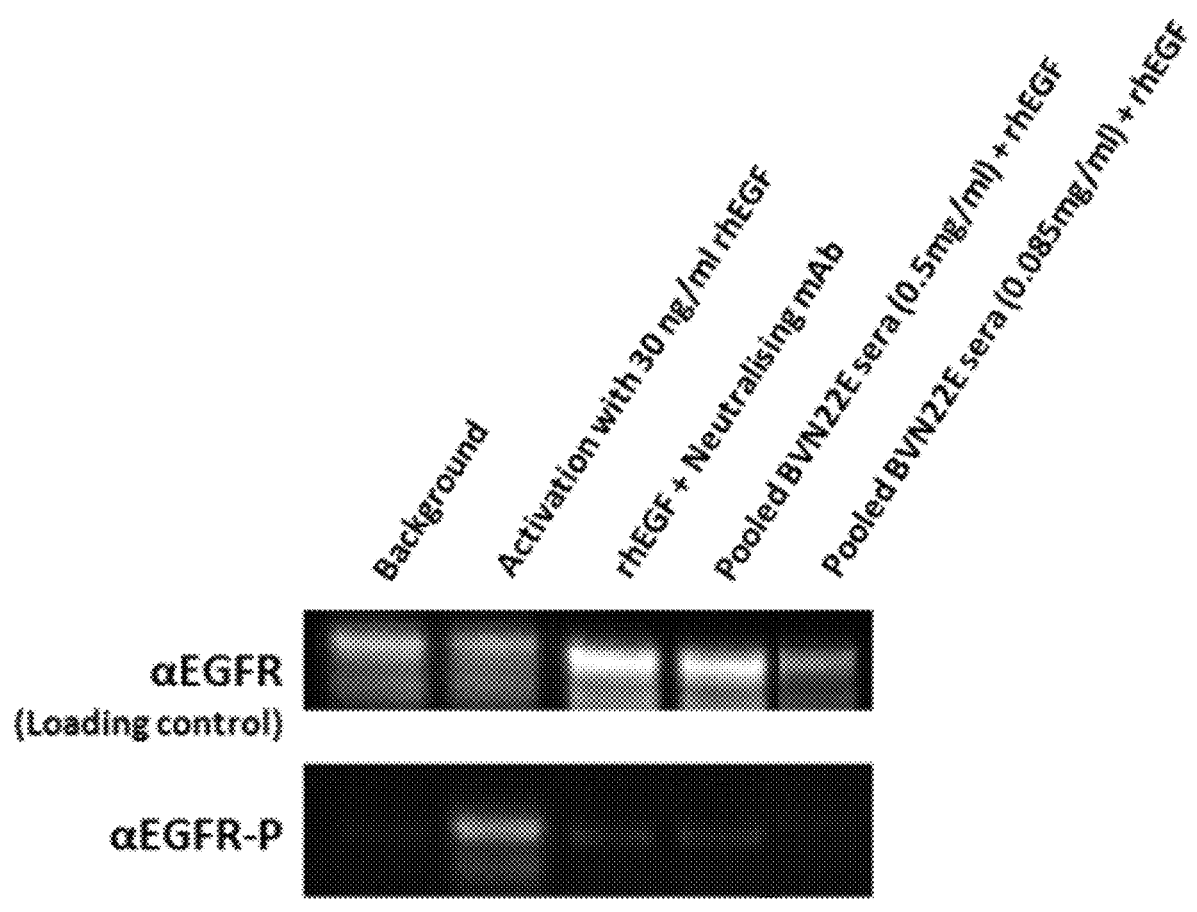
FIG. 5 depicts a Western blot showing purified pooled IgG from 5 rabbits immunized with BVN22E at two concentrations is able to neutralize EGFR-activation of A431 cells by 30 ng/ml rhEGF in a manner similar to a commercially available neutralizing monoclonal antibody.
Figure 6:
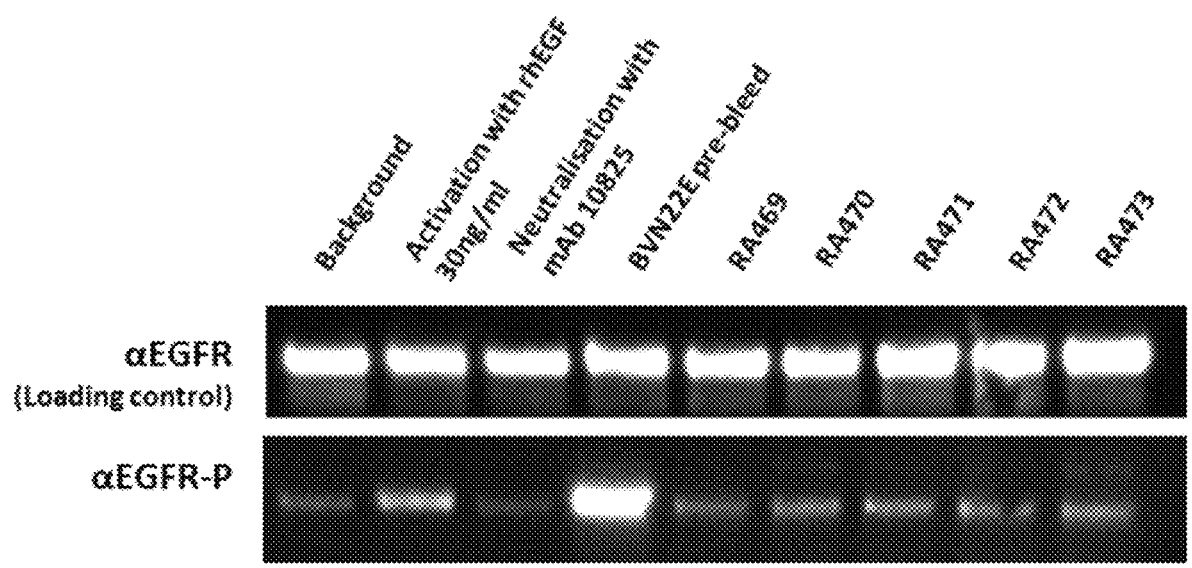
FIG. 6 depicts a Western blot showing that sera from all 5 rabbits immunized with BVN22E is able to neutralize EGFR-activation of A431 cells by 30 ng/ml rhEGF in a manner similar to a commercially available neutralizing monoclonal antibody.

Anti-BVN22E antibodies are able to neutralize EGFR-activation. As shown in FIG. 5, purified pooled IgG from 5 rabbits immunized with BVN22E at two concentrations is able to neutralize EGFR-activation of A431 cells by 30 ng/ml rhEGF in a manner similar to a commercially available neutralizing monoclonal antibody (e.g., R&D Systems monoclonal antibody 10825). FIG. 6 shows that individual sera from each of the 5 rabbits immunized with BVN22E is able to neutralize EGFR-activation of A431 cells by 30 ng/ml rhEGF in a manner similar to a commercially available neutralizing monoclonal antibody.

Figure 7:
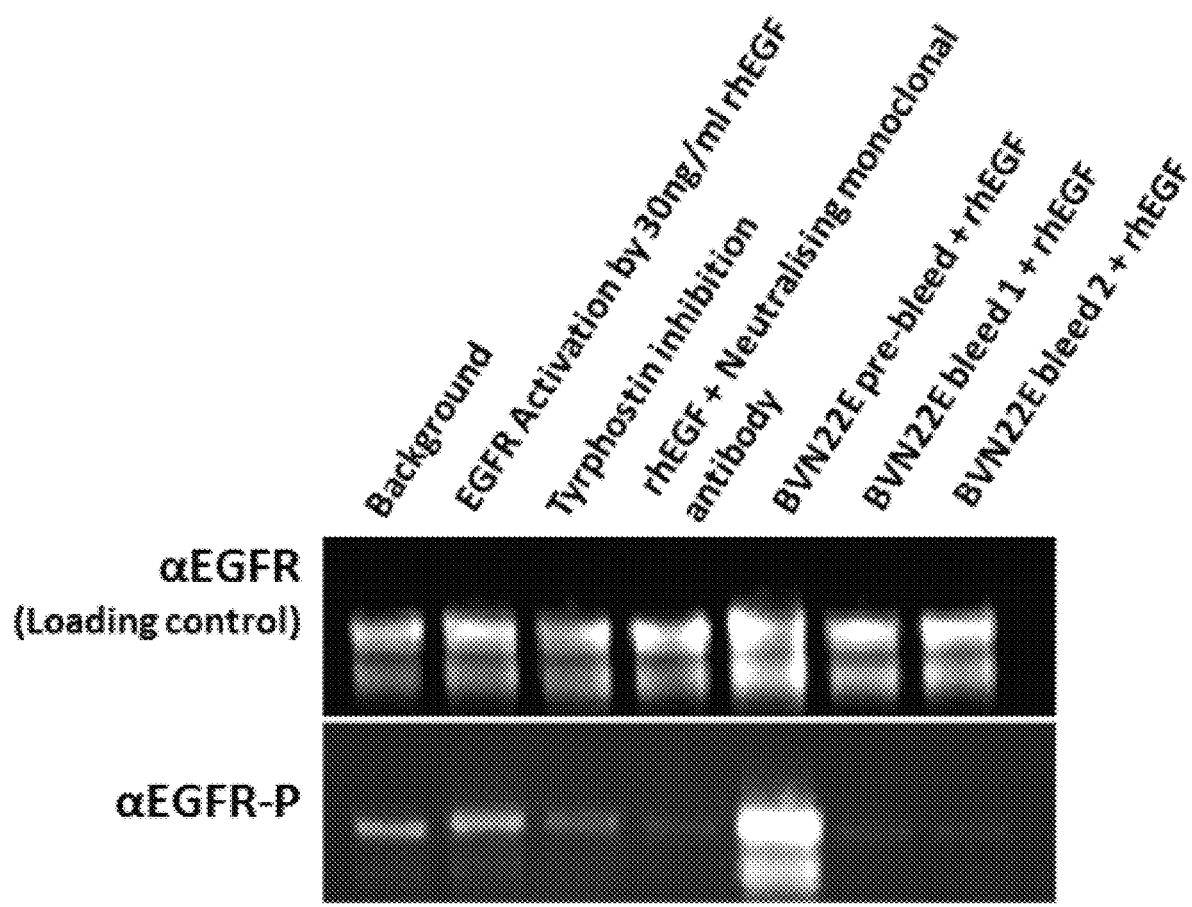
FIG. 7 depicts a Western blot showing that pooled sera from rabbits undergoing immunization with BVN22E is able to neutralize the EGFR signaling from 30 ng/ml rhEGF on A431 cells after just one boost injection (test bleed 1; lane 6) as effectively as a neutralizing monoclonal antibody. Sera from animals prior to immunization has no neutralizing activity (lane 5)

Anti-BVN22E antibodies are able to neutralize EGFR-activation even after only one boost injection. For example, FIG. 7 shows that pooled sera from rabbits undergoing immunization with BVN22E was able to neutralize EGFR signaling from 30 ng/ml rhEGF on A431 cells after only one boost injection (test bleed 1) as effectively as a neutralizing monoclonal antibody (e.g., R&D Systems monoclonal antibody 10825). Sera from animals prior to immunization had no neutralizing activity (lane 5).

Figure 8:
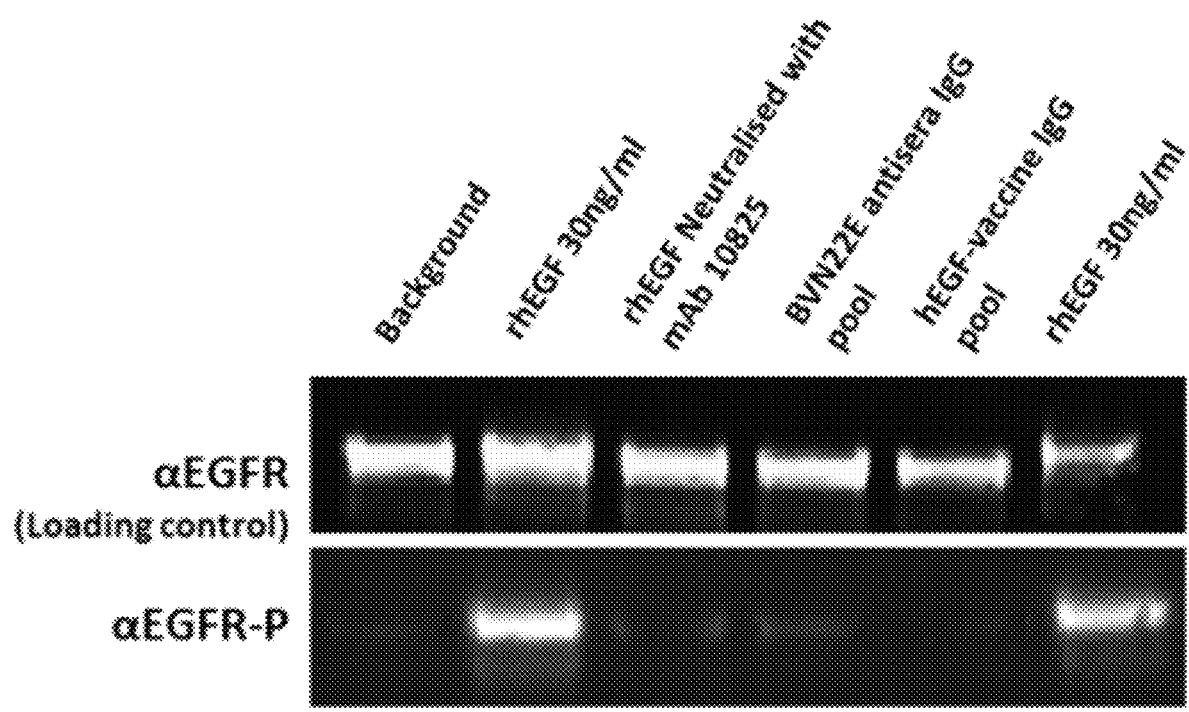
FIG. 8 depicts as Western blot showing that neutralizing activity of IgG purified from sera of rabbits immunized against BVN22E is similar to that from animals immunized with a comparable molecule including only native EGF domains.

Additionally, anti-BVN22E antibodies are quite effective at neutralizing EGFR-activation. For example, FIG. 8 shows that the neutralizing activity of anti-BVN22E IgG is similar to that of IgG purified from animals immunized with a comparable molecule including only native EGF domains and having the following sequence (SEQ ID NO: 31):

NSDSECPLSHDGYCLHDGVCMYIEALDKYACNCVVGYIGERCQYRDLKWW

ELRGSSGNSDSECPLSHDGYCLHDGVCMYIEALDKYACNCVVGYIGERCQ

YRDLKWWELRGGSSGGTSGGGGSGTPQNITDLCAEYHNTQIHTLNDKIFS

YTESLADKREMAIITFKNGATFQVEVPGSQHIDSQKKAIERMKDTLRIAY

LTEAKVEKLCVWNNKTPHAIAAISMAN.

Example 4: Comparison of Potency of BVN22E with Native hEGF-Based Immunogen

BVN22E was expressed and purified as described in Example 1 above. Native EGF-based immunogen was prepared by chemically cross-linking rhEGF with an immunogenic bacterial protein of similar size to CTB pentamers.

The proteins were immunized into mice (n=10) at 30 µg/injection in Freund's complete (prime injection only) or Freund's incomplete (boost injection) using the following schedule:

| | |
|---|---|
| Day 0 | Pre-bleed |
| Day 0 | Immunization |
| Day 14 | Bleed 2 |
| Day 14 | Boost |
| Day 28 | Bleed 3 |

Sera from each group of 10 mice was pooled, and used at three different concentrations to assess the phosphorylation/inhibition of phosphorylation of A431 cells by rhEGF exactly as outlined in Example 3 above.

FIG. 9 shows that the sera generated by both immunogens was able to elicit an immune response that included antibodies able to block the EGF signaling pathway. It can also be seen, when comparing lane 4 with 7, and lane 5 with 8, that the anti-BVN22E sera has a greater neutralizing activity than antisera to the native EGF containing immunogen.

Example 5: Stable Synthetic Neuregulin 1β can be Produced by Bacterial Expression Systems Neuregulin 1β (NRG1β) based molecules have proven very difficult to produce and use. For example, it is very difficult to produce functional NRG1β in *E. coli* because such bacterially generated NRG1β is produced at very low yields, is undesirably glycosylated, and is unable to fold into a functionally active form. Additionally, bacterially produced NRG1β protein is not stable. For example, native wild type Neuregulin is naturally very unstable, and commercially purchased material has a shelf life of only one month at −80° C.

NRG1β includes the following sequence (SEQ ID NO: 32):

GTSHLVKcAEKEKTFcVNGGEcFMVKDLSNPSRYLcKcPNEFTGDRcQNY

VMASF

The equivalent portion of BVN22E includes the following sequence (SEQ ID NO: 33):

NTENDcPLSHEAYcLHDGVcMYIEALDKYAcNcVVGYVGERcQFRDLRWW

DAR

To test whether portions of the BVN22E sequence could exert positive effects on the yield, stability, and function of the NRG1β polypeptide, regions of NRG1β between the cysteine residues (lowercase) were systematically replaced with the equivalent regions from the BVN22E polypeptide. Surprisingly, the portion of BVN22E located between the first and second cysteine (e.g., PLSHEAY) had a beneficial impact when incorporated into the analogous position with NRG1β, while the regions between the remaining cysteine residues did not. This hybrid 'synthetic' polypeptide sequence is referred to as the NRG-BVN hybrid polypeptide, and has the following sequence:

NRG-BVN hybrid polypeptide
(SEQ ID NO: 11)
GTSHLVKcPLSHEAYcVNGGEcFMVKDLSNPSRYLcKcPNEFTGDRcQNY

VMASF

NRG-BVN hybrid polypeptide is able to be expressed in *E. coli* as a folded protein, and purified in a modified (but still very similar) version of the BVN22E purification process as a pentamer. The NRG-BVN sequence can also be expressed in a folded soluble form in an appropriate *E. coli* strain, albeit at lower yield.

Figure 10:
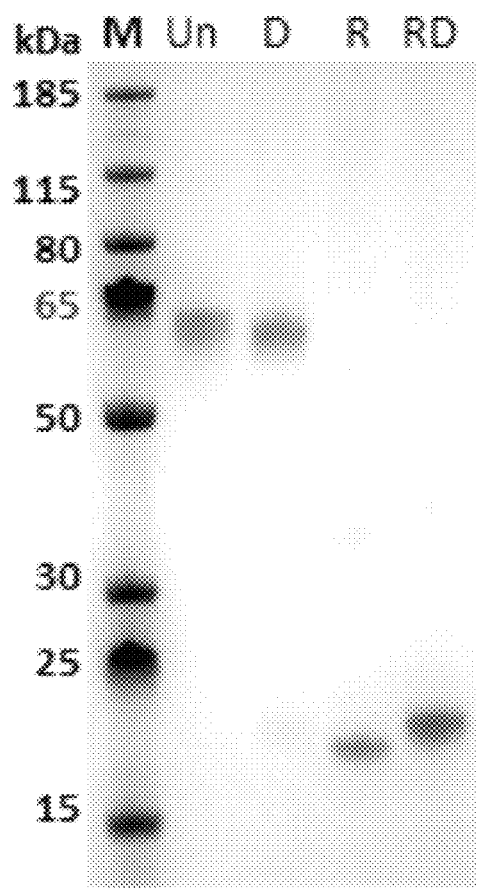
FIG. 10 shows a Coomassie stained SDS gel of a synthetic NRG-CTB molecule in which Un=native, D=heat denatured, R=reduced, RD=reduced and denatured.
Figure 11:
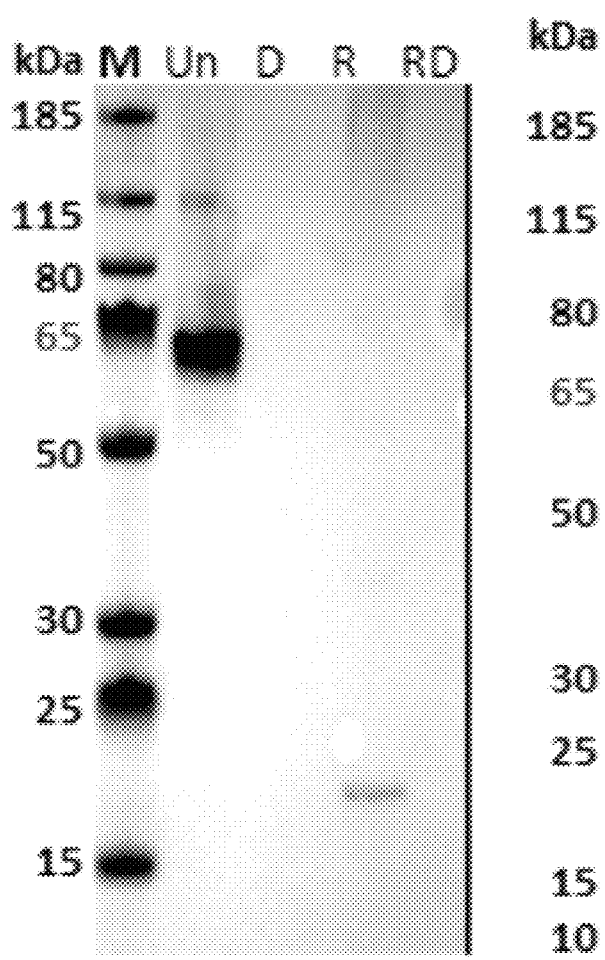
FIG. 11 shows an anti-NRG Western Blot of a synthetic NRG-CTB molecule in which Un=native, D=heat denatured, R=reduced, RD=reduced and denatured.

As shown in FIGS. 10 and 11, bands in a Western Blot reflect the ability of the anti-NRG antibody to recognize various states of protein.

Figure 12:
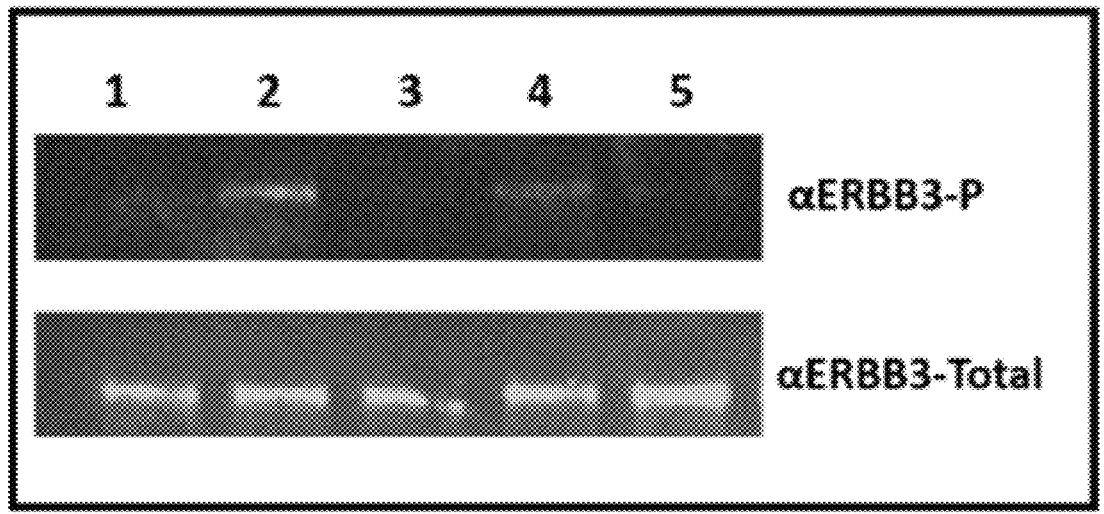
FIG. 12 shows the results of an MCF-7 cell activation assay. The top panel shows activation (e.g., phosphorylation) of the ERB3 Receptor by rhNRG-1β (lane 2), the synthetic NRG-CTB molecule (Lane 4), and the inhibition of both with a neutralizing antibody (Lanes 3 and 5), while the lower panel is a control for ERB3 receptor expression.

FIG. 12 shows a MCF-7 cell activation assay in which the top panel shows activation (e.g., phosphorylation) of the ERB3 Receptor by rhNRG-1β (lane 2), the synthetic NRG-CTB molecule (Lane4), and the inhibition of both with a neutralizing antibody (Lanes 3 and 5). The lower panel is a control for ERB3 receptor expression. This data shows that the synthetic NRG-BVN hybrid polypeptide shows significant stability (e.g., there was no visible degradation after >1 month). Additionally, the NRG-BVN hybrid polypeptide also does not bind to the EGFR (ERB1), the natural receptor for EGF.

Example 6: Stable Synthetic TGFβ can be Produced by Bacterial Expression Systems TGFα-based molecules have also been problematic to produce in bacterial expression systems. For example, a main problem with TGFα-based molecules is that while they can be expressed in bacterial systems to produce a folded protein, the resulting protein is also highly labile and subject to unfolding.

To test whether portions of the BVN22E sequence could exert positive effects on the lability and function of a TGFα-based polypeptide, regions of TGFα between the cysteine residues were systematically replaced with the equivalent regions from the BVN22E polypeptide. Synthetic molecules were designed and made using computer modelling and known structural information to predict/identify important receptor-binding regions. In contrast to the NRG-BVN hybrid polypeptide, the synthetic TGFα molecule contains only the TGFα sequence found from cysteine 3 to 5 (e.g., RFLVQEDKPACV (SEQ ID NO: 34)). This region included the 'B-loop'. This hybrid 'synthetic' polypeptide sequence is referred to as the TGFα hybrid polypeptide, and has the following sequence:

```
TGFα hybrid polypeptide
                                         (SEQ ID NO: 12)
NTENDcPLSHEAYcLHDGVcRFLVQEDKPAcVcVVGYVGERcQFRDLRWW
DAR
```

Figure 13A:
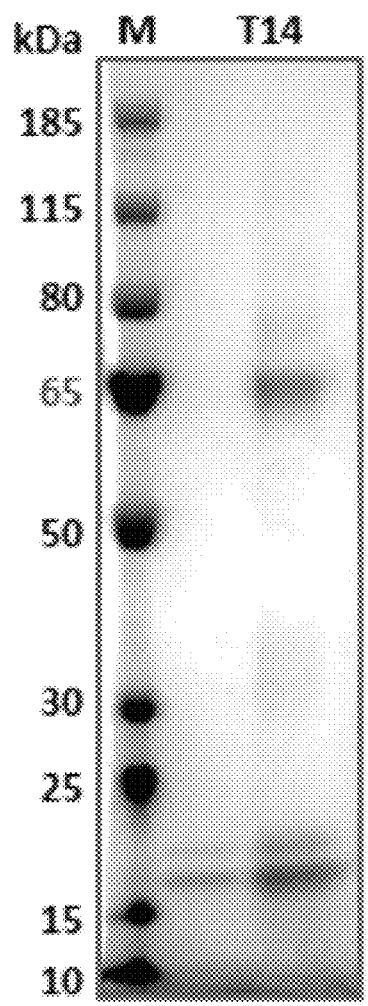
FIGS. 13A-13C show a SDS gel of a synthetic TGFα molecule.
Figure 13B:
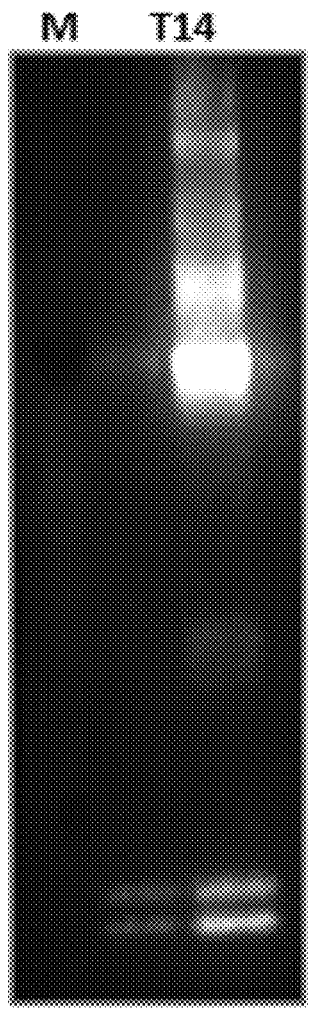
Figure 13C:
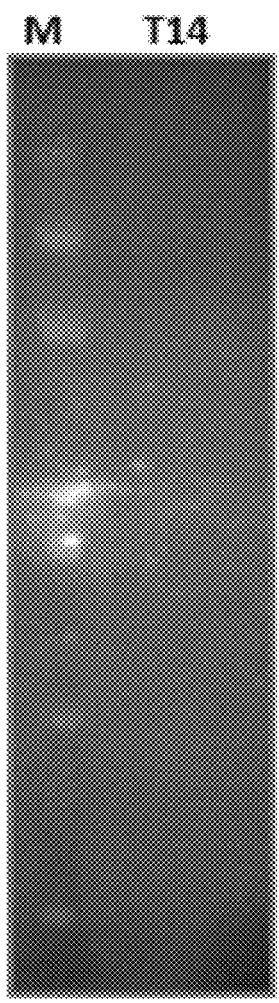

As shown in FIGS. 13A-13C, the TGFα hybrid polypeptide can be expressed, folded and purified in a very similar way to BVN22E. This figure shows an SDS gel of the synthetic TGFα molecule (FIG. 13A) which is recognized by 2 different neutralizing anti-TGFα antibodies (FIG. 13B) but not by either of two different anti-EGF antibodies (FIG. 13C)

Figure 14:
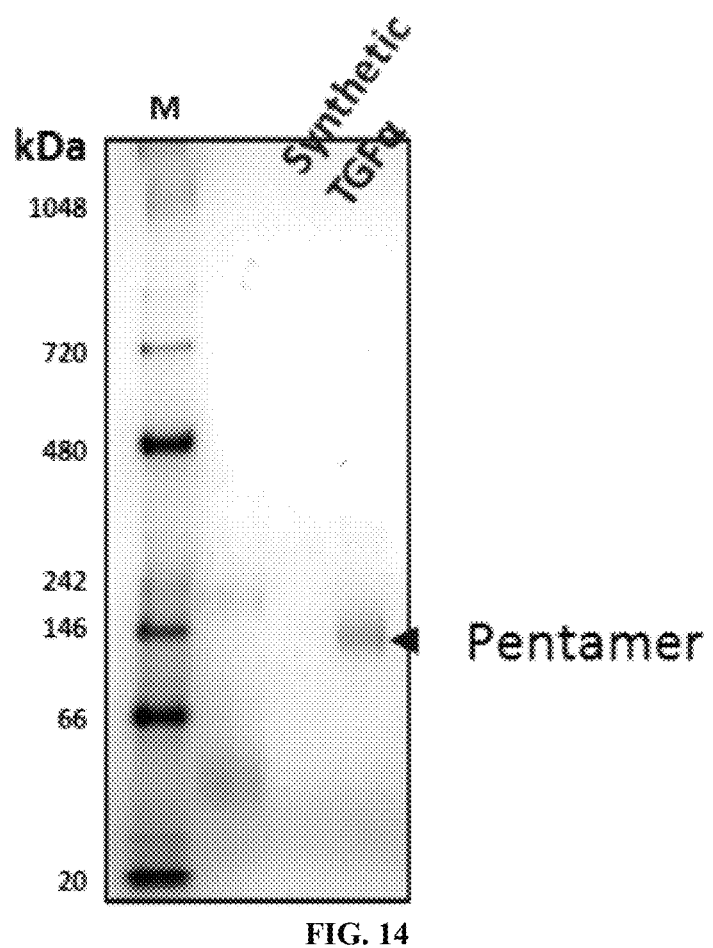
FIG. 14 depicts a Coomassie stained Blue-native gel showing that purification of a synthetic TGFα molecule produces a single pentamer band.

Additionally, the TGFα hybrid polypeptide forms pentamers and some other oligomers that are removed during purification. As shown in FIG. 14, following purification a single pentamer band is visible on Blue-native gels.

Figure 15A:
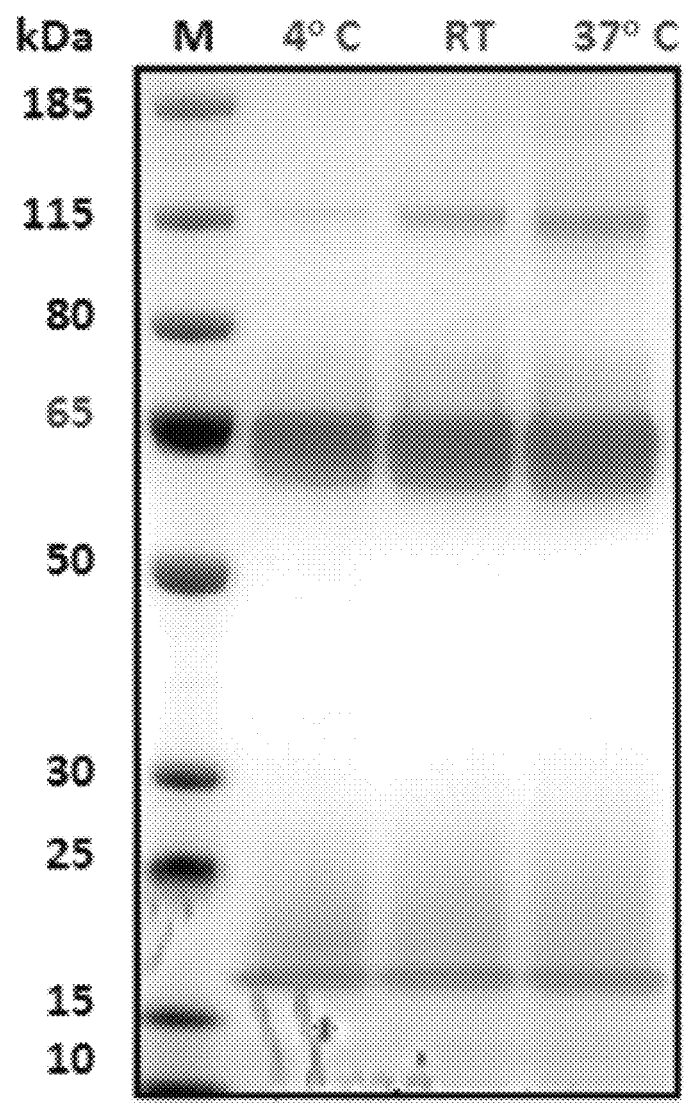
FIGS. 15A-15B show a Coomassie stained SDS gel and an anti-TGFα Western blot, respectively, which show that the synthetic TGFα molecule shows improved stability, remaining as a discrete pentamer band after more than three weeks at elevated temperatures (e.g., room temperature and 37° C.).
Figure 15B:
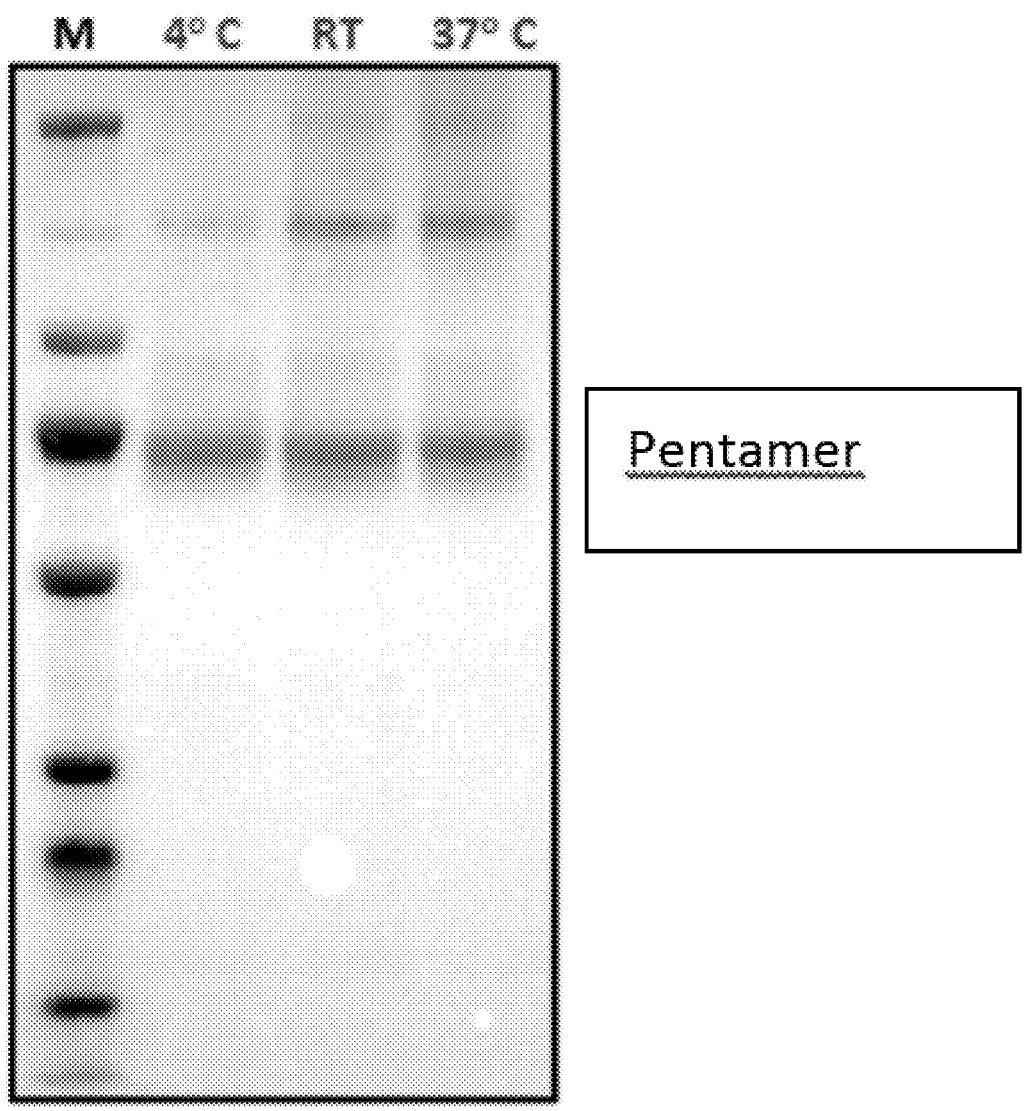

As shown in FIGS. 15A and 15B, the TGFα hybrid polypeptide also shows improved stability, remaining as sharp pentamer after >3 weeks at elevated temperatures in an accelerated stability study.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

We claim:

1. A synthetic protein, comprising:

a synthetic Epidermal Growth Factor (sEGF) growth factor comprising at least one synthetic targeted signaling pathway (sTSP) domain of a human Epidermal Growth Factor (hEGF) TSP (hTSP) domain, wherein the at least one sTSP is 95%, 96%, 97%, 98%, 99% or 100% identical to the amino acid sequence NTENDCPLSHEAYCLHDGVCMYIEALDKY-ACNCVVGYVGERCQFRDLRWWDAR (SEQ ID NO: 33), excluding the following amino acid changes: T2S, E3D, N4S, DSE, E11D, A12G, V38I, F44Y, R48K, F511, and A52L;

at least one linker; and an immunogenic polypeptide, wherein the at least one linker includes a first linker that separates the sTSP from the immunogenic polypeptide.

2. The synthetic protein according to claim 1, wherein the immunogenic polypeptide comprises a cholera toxin B (CT-B) protein.

3. The synthetic protein according to claim 1, wherein the first linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), SGGGGSGGGSSGGG (SEQ ID NO: 29) and GGSGGTSGGGGGSG (SEQ ID NO: 30).

4. The synthetic protein according to claim 3, wherein the first linker is GGSGGTSGGGGGSG (SEQ ID NO: 30).

5. The synthetic protein according to claim 1, wherein the synthetic growth factor comprises a first sTSP domain and a second sTSP domain.

6. The synthetic protein according to claim 5, wherein the at least one linker includes a second linker that separates the first sTSP domain and the second sTSP domain, and the first linker separates the second sTSP domain from the immunogenic polypeptide.

7. The synthetic protein according to claim 6, wherein the second linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29).

8. The synthetic protein according to claim 6, wherein the second linker is GSSG (SEQ ID NO: 14).

9. The synthetic protein according to claim 1, wherein the synthetic protein has the amino acid sequence of SEQ ID NO:2.

10. An immunogenic composition, comprising the synthetic protein of claim 9 and one or more components selected from the group consisting of an adjuvant, a carrier, an excipient, a diluent, and combinations thereof.

11. An immunogenic composition, comprising the synthetic protein of claim 1 and one or more components selected from the group consisting of an adjuvant, a carrier, an excipient, a diluent, and combinations thereof.

12. The immunogenic composition according to claim 11, wherein the immunogenic polypeptide comprises a cholera toxin B (CT-B) protein.

13. The immunogenic composition according to claim 11, wherein the first linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), SSGGGGSGGGSSGGG (SEQ ID NO: 29) and GGSGGTSGGGGGSG (SEQ ID NO: 30).

14. The immunogenic composition according to claim 13, wherein the first linker is GGSGGTSGGGGGSG (SEQ ID NO: 30).

15. The immunogenic composition according to claim 11, wherein the synthetic Epidermal Growth Factor (sEGF) growth factor comprises a first sTSP domain and a second sTSP domain.

16. The immunogenic composition according to claim 15, wherein the at least one linker includes a second linker that separates the first sTSP domain and the second sTSP domain, and the first linker separates the second sTSP domain from the immunogenic polypeptide.

17. The immunogenic composition according to claim 16, wherein the second linker is selected from the group consisting of SSG (SEQ ID NO: 13), GSSG (SEQ ID NO: 14), SSGGG (SEQ ID NO: 15), SGG (SEQ ID NO: 16), GGSGG (SEQ ID NO: 17), GGGGS (SEQ ID NO: 18), SSGGGSGG (SEQ ID NO: 19), SSGGGGSGGG (SEQ ID NO: 20), TSGGGSG (SEQ ID NO: 21), TSGGGGSGG (SEQ ID NO: 22), SSGGGSGGSSG (SEQ ID NO: 23), GGSGGTSGGGSG (SEQ ID NO: 24), SGGTSGGGGSGG (SEQ ID NO: 25), GGSGGTSGGGGSGG (SEQ ID NO: 26), SSGGGGSGGGSSG (SEQ ID NO: 27), SSGGGSGGSSGGG (SEQ ID NO: 28), and SSGGGGSGGGSSGGG (SEQ ID NO: 29).

18. The immunogenic composition according to claim 17, wherein the second linker is GSSG (SEQ ID NO: 14).

19. The immunogenic composition according to claim 11, wherein the synthetic protein has the amino acid sequence of SEQ ID NO:2.

* * * * *